United States Patent [19]

Clark et al.

[11] 4,110,534

[45] Aug. 29, 1978

[54] PROCESS FOR THE PREPARATION OF 3-VINYL AND SUBSTITUTED VINYL CEPHALOSPORINS

[75] Inventors: John Colin Clark, Gerrards Cross, England; James Kennedy, Angus, Scotland; Alan Gibson Long, Greenford; Niall Galbraith Weir, London, both of England

[73] Assignee: Glaxo Laboratories Limited, Greenford, England

[21] Appl. No.: 679,073

[22] Filed: Apr. 21, 1976

Related U.S. Application Data

[60] Division of Ser. No. 486,633, Jul. 8, 1974, which is a continuation of Ser. No. 108,136, Jan. 20, 1971, abandoned.

[30] Foreign Application Priority Data

Jan. 23, 1970 [GB] United Kingdom ............... 3464/70
Jan. 23, 1970 [GB] United Kingdom ............. 21907/70
Jan. 23, 1970 [GB] United Kingdom ............. 28194/70

[51] Int. Cl.$^2$ .................. C07D 501/02; C07D 501/04
[52] U.S. Cl. ...................................... 544/16; 424/246; 542/429; 542/442; 542/427; 542/426
[58] Field of Search ....................... 260/240 G, 243 C; 544/16

[56] References Cited

U.S. PATENT DOCUMENTS 3,853,860  12/1974  Weir ................................ 260/243 C

*Primary Examiner*—Nicholas S. Rizzo
*Attorney, Agent, or Firm*—Bacon & Thomas

[57] ABSTRACT

The invention is concerned with the preparation of $\Delta^3$-4-carboxy cephalosporin antibiotics possessing a 3-vinyl group or substituted 3-vinyl group by means of phosphorous intermediates.

10 Claims, No Drawings

PROCESS FOR THE PREPARATION OF 3-VINYL AND SUBSTITUTED VINYL CEPHALOSPORINS

This is a divisional of application Ser. No. 486,633, filed July 8, 1974, which is in turn a continuation of application Ser. No. 108,136, filed on Jan. 20, 1971, and now abandoned.

This invention is concerned with improvements in or relating to antibiotics. In particular, the invention is concerned with a novel group of $\Delta^3$-4-carboxy cephalosporin antibiotics having certain substituents at position 3 hereinafter defined.

The cephalosporin compounds referred to in this specification are generally named with reference to cepham (see *J. Amer. Chem. Soc.* 1962, 84, 3400). The term "cephem" refers to the basic cepham structure with a single double bond. Where a dotted line bridges the 2-, 3- and 4-positions this indicates that the compound may be a ceph-2-em or ceph-3-em compound.

As is well known in the art, $\Delta^3$-4-carboxy cephalosporin antibiotics are compounds which are generally depicted by the formula

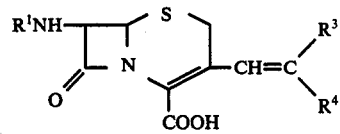

where $R^1$ is a carboxylic acyl group and $R^2$ is the 3-substituent.

The novel $\Delta^3$-4-carboxy cephalosporin antibiotics of the present invention are characterized by having at position 3 a substituent of the formula

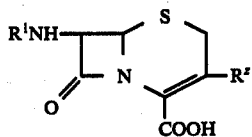

wherein $R^3$ and $R^4$ are each a hydrogen atom or an organic substituting group e.g. a lower alkyl group, cycloalkyl having up to 6 carbon atoms, phenyl, phenyl substituted by halogen, lower alkyl or nitro, lower alkoxycarbonyl, lower alkylcarbonyl, cyano, carboxy, phenylloweralkoxy carbonyl, diphenyl loweralkoxycarbonyl, benzyl or phenylethyl and non toxic derivatives thereof.

$\Delta^3$-4-carboxy cephalosporin antibiotics possessing a 3-vinyl and 3-substituted vinyl substituent are an entirely new class of compounds.

By the term "non-toxic" as applied to the compounds of the invention we mean those derivatives which are physiologically acceptable in the dosage at which they are administered. Such derivatives include salts and esters.

Compounds according to the invention possess antibacterial activity against a range of gram positive and gram negative organisms and are of value in human and veterinary medicine. They may also be of value in the preparation of other 3-substituted cephalosoporin compounds.

The compounds of the invention may be represented by general formula

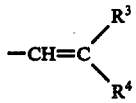

wherein $R^1$ is a carboxylic acyl group, and $R^3$ and $R^4$, which may be the same or different, are each a hydrogen atom or an organic substituting group.

According to a preferred embodiment of the invention, $R^3$ and $R^4$ are each a hydrogen atom i.e. the compound of the formula I possesses a 3-vinyl group.

The groups $R^3$ and/or $R^4$ may be a substituted or unsubstituted aliphatic, cycloaliphatic, (e.g. cyclopentyl or cyclohexyl) araliphatic (e.g. benzyl or phenylethyl) or aromatic (e.g. phenyl or 4-nitrophenyl) group.

A preferred class of compounds of the general formula (I) are those having the group —CH= C($R^5$)$_2$ at the 3-position (wherein the $R^5$ groups, which may be the same or different, are each a hydrogen atom or an alkyl group, preferably a lower alkyl group such as methyl ethyl, iso-propyl, n-propyl etc, or an aryl group) and salts (e.g. alkali metal salts of such compounds).

The group $R^1$ in the above formula may represent a wide variety of acyl groups which may contain 1–20 carbon atoms. Specific acyl groups are illustrated in the accompanying list which is not intended to be exhaustive:

(i) $R^u C_n H_{2n} CN$- where $R^u$ is aryl (carbocyclic or heterocyclic), cycloalkyl, substituted aryl, substituted cycloalkyl, cyclohexadienyl, or a non-aromatic, heterocyclic, or mesoionic group, and $n$ is an integer from 1–4. Examples of this group include phenylacetyl; substituted phenylacetyl e.g. fluorophenylacetyl, nitrophenylacetyl, aminophenylacetyl, acetoxyphenylacetyl, methoxyphenylacetyl, methylphenylacetyl, or hydroxyphenylacetyl; N,N-bis (2-chloroethyl)aminophenylpropionyl; thien-2- and 3-ylacetyl; 4-isoxazolyl and substituted 4-isoxazolylacetyl; pyridylacetyl; tetrazolylacetyl or a sydnoneacetyl group. The substituted 4-isoxazolyl group may be a 3-aryl-5-methyl isoxazol-4-yl group; the aryl group being e.g. phenyl or halophenyl e.g. chloro- or bromo-phenyl. An acyl group of this type is 3-o-chlorophenyl-5methylisoxazol-4-yl-acetyl.

(ii) $C_n H_{2n+1} CO$- where $n$ is an integer from 1–7. The alkyl group may be straight or branched and, if desired, may be interrupted by an oxygen or sulphur atom or substituted by e.g. a cyano group a carboxy group, an alkoxycarbonyl group, a hydroxy group or a carboxycarbonyl group (—CO.COOH). Examples of such groups include cyanoacetyl, hexanoyl, heptanoyl, octanoyl and butylthioacetyl.

(iii) $C_n H_{2n-1} CO$— where $n$ is an integer from 2–7. The alkenyl group may be straight or branched and, if desired, may be interrupted by an oxygen or a sulphur atom. An example of such a group is allylthioacetyl.

(iv)

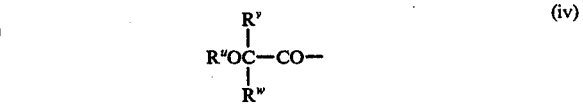

where $R^u$ has the meaning defined under (i) and in addition may be benzyl, and $R^v$ and $R^w$ which may be the same or different each represent hydrogen, phenyl, benzyl, phenethyl or lower alkyl. Examples of such groups include phenoxyacetyl, 2-phenoxy-2-phenylacetyl, benzyloxyacetyl, 2-phenoxypropionyl, 2-phenoxybutyryl, methylthiophenoxyacetyl.

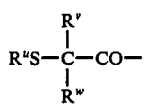
(v)

where $R^u$ has the meaning defined under (i) and, in addition, may be benzyl and $R^v$ and $R^w$ have the meanings defined under (iv). Examples of such groups include S-phenylthioacetyl, S-chlorophenylthioacetyl, S-fluorophenylthioacetyl, pyridylthioacetyl, and S-benzylthioacetyl.

(vi) $R^u Z(CH_2)_m CO$— where $R^u$ has the meaning defined under (i) and, in addition, may be benzyl, Z is an oxygen or sulphur atom and m is an integer from 2–5. An example of such a group is S-benzylthiopropionyl.

(vii) $R^u CO$— where $R^u$ has the meaning defined under (i). Examples of such groups include benzoyl, substituted benzoyl (e.g. aminobenzoyl), 4-isoxazolyl- and substituted 4-isoxazolylcarbonyl, cyclopentanecarbonyl, sydnonecarbonyl, naphthoyl and substituted naphthoyl (e.g. 2-ethoxynaphthoyl), quinoxalinylcarbonyl and substituted quinoxalinylcarbonyl (e.g. 3-carboxy-2-quinoxalinylcarbonyl). Other possible substituents for benzoyl include alkyl, alkoxy, phenyl, phenyl substituted by carboxy, alkylamido, cycloalkylamido, allylamido, phenyl(lower)alkylamido, morpholinocarbonyl, pyrrolidinocarbonyl, piperidinocarbonyl, tetrahydropyridino, furfurylamido or N-alkyl-N-anilino, or derivatives thereof, and such substituents may be in the 2- or 2- and 6- positions. Examples of such substituted benzoyl groups are 2,6-dimethoxybenzoyl, 2-methylamidobenzyl and 2-carboxybenzoyl. Where the group $R^u$ represents a substituted 4-isoxazolyl group, the substituents may be as set out above under (i). Examples of such 4-isoxazolyl groups are 3-phenyl-5-methyl-isoxazol-4-yl carbonyl, 3-o-chlorophenyl-5-methyl-isoxazol-4-yl carbonyl and 3-(2,6-dichlorophenyl)-5-methyl-isoxazol-4-yl carbonyl.

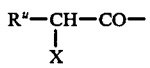
(viii)

where $R^u$ has the meaning defined under (i) and X is amino, substituted amino (e.g. acylamido or a group obtained by reacting the α-aminoacylamido group of the 7-side chain with an aldehyde or ketone e.g. acetone, methylethylketone or ethyl acetoacetate), hydroxy, carboxy, esterified carboxy, azido, triazolyl, tetrazolyl, cyano, halogeno, acyloxy (e.g. formyloxy or lower alkanoyloxy) or etherified hydroxy group. Examples of such acyl groups are α-aminophenylacetyl, and α-carboxyphenylacetyl.

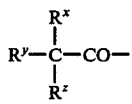
(ix)

where $R^x$, $R^y$ and $R^z$ which may be the same or different may each represent lower alkyl, phenyl or substituted phenyl or $R^x$ represents hydrogen. An example of such an acyl group is triphenylmethylcarbonyl.

(x) $R^u$—NH—CO— where $R^u$ has the meaning defined under (i) and in addition may be hydrogen, lower alkyl or halogen substituted lower alkyl. An example of such a group is $Cl(CH_2)_2 NHCO$.

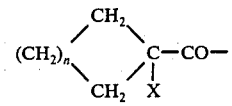
(xi)

where X has the meaning defined under (viii) above and n is an integer of from 1 to 4. An example of such an acyl group is 1-aminocyclohexanecarbonyl.

(xii) Amino acyl, for example $R^w CH(NH_2).(CH_2)_n CO$— where n is an integer from 1–10, or $NH_2.C_n H_{2n} Ar(CH_2)_m CO$, where m is zero or an integer from 1–10, and n is 0, 1 or 2, $R^w$ is a hydrogen atom or an alkyl, aralkyl or carboxy group or a group as defined under $R^u$ above, and Ar is an arylene group, e.g. p-phenylene or 1,4-naphthylene. Examples of such groups are disclosed in British Patent Specification No. 1,054,806. A group of this type is the n-aminophenylacetyl group. Other acyl groups of this type include those, e.g. 5-aminoadipoyl, derived from naturally occurring amino acids, and derivatives thereof e.g. N-benzoyl-5-aminoadipoyl.

(xiii) Substituted glyoxylyl groups of the formula $R^y.CO.CO$— where $R^y$ is an aliphatic, araliphatic or aromatic group, e.g. a thienyl group, a phenyl group, or a mono-, di- or tri- substituted phenyl group, the substituents being, for example, one or more halogen atoms (F, Cl, Br, or I), methoxy groups, methyl groups or amino groups, or a fused benzene ring. Included in this group are also the α-carbonyl derivatives of the above substituted glyoxylyl groups.

(xiv) Formyl.

Where compounds of formula I are primarily intended for use as intermediates important species of the group $R^1$ are:

(xv) Hydrocarbyloxycarbonyl and substituted hydrocarbyloxy groups (wherein the 7-amino group forms part of a urethane), e.g. lower alkoxycarbonyl groups (such as methoxycarbonyl, ethoxycarbonyl and t-butoxycarbonyl groups); halo lower alkoxycarbonyl groups e.g. 2,2,2-trichloroethoxycarbonyl; aralkoxycarbonyl groups such as benzyloxycarbonyl, 4-methoxybenzyloxycarbonyl, diphenylmethoxycarbonyl and 4-nitrobenzyloxycarbonyl groups; and cycloalkoxycarbonyl groups e.g. adamantyloxycarbonyl.

(xvi) Haloformyl e.g. chloroformyl.

A particularly important compound of the general formula (I) is 7β-(D-2-amino-2-phenylacetamido)-3-vinylceph-3-em-4-carboxylic acid of the formula:

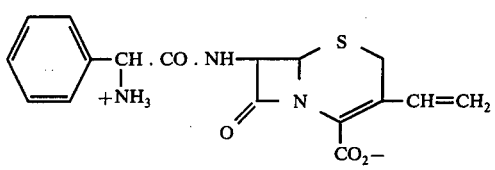
(II)

7β-(D-2-Amino-2-phenylacetamido)-3-vinylceph-3-em-4-carboxylic acid is a broad-spectrum antibiotic being active against gram-positive and gram-negative organisms as evidenced by in vitro tests. It is substantially resistant to degradation in vivo as evidenced by animal tests. A particularly significant property of this compound is that, when given by the oral route, it is well absorbed and gives good blood levels. It has an appreciable level of activity on oral administration. It will be appreciated that the property of absorption by the subject after oral administration is highly desirable.

7β-(D-2-amino-2-phenylacetamido)-3-vinylceph-3-em-4-carboxylic acid and related compounds form the subject of copending application Ser. No. 108,134 of NIALL GALBRAITH WEIR filed on even date herewith).

Salts which may be formed from the compounds according to the invention include (a) inorganic base salts such as alkali metal, e.g. sodium and potassium, alkaline earth e.g. calcium, and organic base salts e.g. procaine and dibenzylethylene diamine salts and (b) acid addition salts e.g. with hydrochloric, hydrobromic, sulphuric, nitric, phosphoric, toluene-p-sulphonic and methanesulphonic acids. The salts may also be in the form of resinates, formed, e.g. with a polystyrene resin containing amino, quaternary amino, or sulphonic acid groups, or a resin containing carboxyl groups, e.g. a polyacrylic acid resin. The resin may if desired be cross-linked, e.g. it may be a copolymer of styrene and divinylbenzene containing the appropriate groups.

Preparation of compounds of general formula (I)

According to a further embodiment of the invention there is provided a process for the preparation of a cephalosporin compound of formula I defined above which comprises (A) reacting a compound of the formula

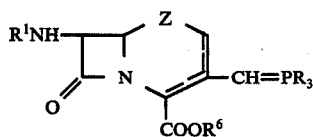

(wherein $R^1$ is a carboxylic acyl group, $R^6$ is hydrogen or a carboxyl-blocking group, Z is >S or >S→0 (α or β-) and R is an organic substituting group), or a Zwitterionic form thereof, with a carbonyl compound of the formula

$R^3.CO.R^4$ (wherein $R^3$ and $R^4$ have the above-defined meanings) or (C) acylating a compound of the formula

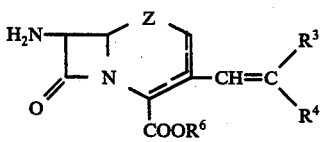

(wherein Z, $R^3$, $R^4$ and $R^6$ have the above defined meanings) with an acylating agent corresponding to the acid $R^1COOH$ whereafter, if necessary, any of the following reactions (D) are carried out;
(i) conversion of a $\Delta^2$ isomer into the desired $\Delta^3$ isomer,
(ii) removal of any groups protecting any amino or carboxyl groups and (iii) reduction of a compound in which Z is >S→0 to form the desired Z= >S An alternative to step (A) comprises
(B) reacting a compound of the formula

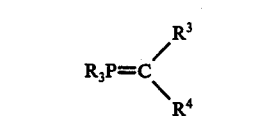

(wherein $R^1$, Z and $R^6$ have the above defined meanings) with a phosphorane ylid of the formula

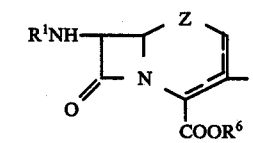

(wherein R, $R^3$ and $R^4$ have the above-defined meaning) This reaction forms the subject of copending application Ser. No. 108,155 of ALAN GIBSON LONG and NIALL GALBRAITH WEIR filed on even date herewith.

For the sake of simplicity the group

is shown below as Q.

Preparation of compounds of general formula I via 3-phosphoranylidene compounds

This may be effected by a series of reactions which may be depicted as

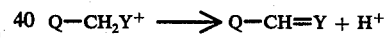

$Q-CH_2X \longrightarrow Q-CH_2Y^+$ $Q-CH_2Y^+ \longrightarrow Q-CH=Y + H^+$

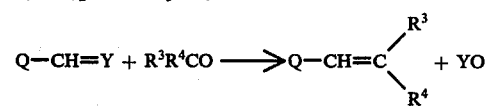

X is halogen i.e. chlorine, bromine or iodine and Y is $PR_3$, R being organic groups. The conversion may also be effected using compounds where Y is $-PO(OR)_2$ although the reaction scheme may be somewhat different.

The R groups may be the same or different and may be alkyl, aralkyl or aryl groups or such groups substituted by, for example, one or more halogen atoms, nitro groups, cyano groups, amino groups, acyl groups, acylamido groups and the like. Examples of R groups include lower alkyl e.g. methyl, ethyl, propyl or butyl; and phenyl or substituted phenyl; and benzyl.

The compounds $QCH_2X$ are 3-halomethylcephalosporins and may be prepared by halogenation of a 7β-acylamido-3-methylceph-3-em-4-carboxylic acid ester 1β-oxide followed, if desired, by reduction of the 1β-oxide group as described in copending application No. 66,128. 3-Halomethylceph-3-em compounds may also be prepared by the method described in Belgian Pat. No. 719,711. The corresponding ceph-2-em compounds may be prepared by the method of Dutch published Patent Application No. 6902013 by reaction of a ceph-2- em-3-methyl compound with N-bromo-succinimide to yield the ceph-2-em-3-bromoethyl compound.

The carboxyl blocking group $R^6$, substituting the 4-carboxyl group, is, preferably, an ester formed with an alcohol or phenol which may readily be split off at a later stage of the reaction.

The group protecting the 4-carboxyl group of formula I may be formed with an alcohol (aliphatic or araliphatic), phenol, silanol, stannanol or acid which may readily be split off at a later stage of the reaction. Suitable esters thus include compounds containing as 4-ester group, a group selected from the following list which is not intended to be an exhaustive list of possible ester groups.

(i) — $COOCR^aR^bR^c$ wherein at least one of $R^a$, $R^b$ and $R^c$ is an electron-donor e.g. p-methoxyphenyl, 2,2,6-trimethylphenyl, 9-anthryl, methoxy, acetoxy, tetrahydrofur-2-yl, tetrahydropyran-2-yl or fur-2-yl. The remaining $R^a$, $R^b$ and $R^c$ groups may be hydrogen or organic substituting groups. Suitable ester groups of this type include p-methoxybenzyloxycarbonyl and 2,4,6-trimethylbenzyloxycarbonyl. (ii) -$COOCR^aR^bR^c$ wherein at least one of $R^a$, $R^b$ and $R^c$ is an electron-attracting group e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining $R^a$, $R^b$ and $R^c$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl. (iii) - $COOCR^aR^bR^c$ wherein at least two of $R^a$, $R^b$ and $R^c$ are hydrocarbon such as alkyl e.g. methyl or ethyl, or aryl e.g. phenyl and the remaining $R^a$, $R^b$ and $R^c$ group, if there is one, is hydrogen. Suitable esters of this type include, t-butyloxycarbonyl, t-amyloxycarbonyl, diphenylmethoxycarbonyl and triphenylmethoxycarbonyl. (iv) — $COOR^d$ wherein $R^d$ is adamantyl, 2-benzyloxyphenyl, 4-methylthiophenyl or tetrahydropyran-2-yl.

Silyl esters may conveniently be prepared from a halosilane or a silazane of the formula $R^4_3SiX$; $R^4_2SiX_2$; $R^4_3Si.NR^4_2$; $R^4_3Si.NH.SiR^4_3$; $R^4_3Si.NH.COR^4$; $R^4_3Si.NH.CO.NH.SiR^4_3$; $R^4NH.CO.NR^4.SiR^4_3$; or $R^4C(OSiR^4_3):NSiR^4_3$ where X is a halogen and the various groups $R^4$, which can be the same or different, represent hydrogen atoms or alkyl, e.g. methyl, ethyl, n-propyl, iso-propyl; aryl, e.g. phenyl; or aralkyl e.g. benzyl groups.

Preferred derivatives of silanols are silyl chlorides such as for example trimethylchlorosilane and dimethyldichlorosilane.

The carboxyl groups may be regenerated from an ester by any of the usual methods; for example, acid- and base-catalysed hydrolysis (especially for silyl and stannyl esters) is generally applicable, as well as enzymically-catalysed hydrolyses: however, aqueous mixtures may be poor solvents for these compounds and they may cause isomerizations, rearrangements, side-reactions, and general destruction, so that special methods may be desirable. Five suitable methods of deesterification are: Reactions with Lewis acids: Suitable Lewis acids for reaction with the esters include trifluoroacetic acid, formic acid, hydrochloric acid in acetic acid, zinc bromide in benzene and aqueous solutions or suspensions of mercuric compounds. The reaction with the Lewis acid may be improved by addition of a nucleophile such as anisole. Reduction: Suitable systems for effecting reduction are zinc/acetic acid, zinc/formic acid, zinc/lower alcohol, zinc/pyridine, palladisedcharcoal and hydrogen, electrolysis, and sodium and liquid ammonia. Attack by nucleophiles: Suitable nucleophiles are those containing a nucleophilic oxygen or sulphur atom for example alcohols, mercaptans and water. Oxidative methods: for example, which involve the use of hydrogen peroxide and acetic acid. Irradiation.

Preparation of phosphonium compounds

The phosphonium compounds $QCH_2Y^+$ may be prepared by reaction of the corresponding 3-halomethyl compound, preferably the 3-bromo- or 3-iodomethyl ceph-3 or 2-em compound, with a phosphorus-containing nucleophile such as a trivalent phosphorus nucleophile e.g. a phosphine, phosphorus acid or derivative thereof.

The reaction may be carried out in a solvent, preferably an inert organic solvent, since this will facilitate working and, if it is found to be necessary to heat the reaction mixture, the presence of a solvent serves to prevent undesired decomposition during heating. Reactions with 3-bromomethyl and 3-iodomethyl compounds proceed readily at normal temperatures although it may be found to be more efficient to work at elevated temperatures. With 3-chloromethyl compounds heating is usually necessary in order to ensure that the reaction times are practical for normal operating criteria. The reaction may be facilitated by the presence of small amounts (e.g. one equivalent or less) of alkali metal bromides or iodides e.g. sodium bromide or sodium iodide.

Suitable inert solvents include acyclic ethers, e.g. diethyl ether, cyclic ethers e.g. dioxan or tetrahydrofuran; esters e.g. ethyl acetate; hydrocarbons e.g. benzene; halogenated hydrocarbons e.g. methylene chloride; dimethylsulphoxide; amides e.g. dimethylformamide, dimethylacetamide, and hexamethylphosphoramide and the like.

The phosphorus compounds thus obtained are novel compounds and the invention thus provides novel ceph-3 or 2-em compounds having the group —$CH_2Y$ at the 3-position wherein Y is -$P^+R_3$ or -$PO(OR)_2$ and the R groups are organic substituting groups (which may be the same or different). The novel compounds may be defined by the following formula:

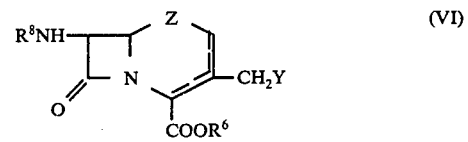

(VI)

wherein $R^8$ is a hydrogen atom or a carboxylic acyl group $R^1$; $R^6$ is a hydrogen atom or an esterifying group; Z is >S, or >SO and Y has the above defined meaning. When Y is a $P^+R_3$ group, the group at the 4-position may be $COO^-$; compounds of this type may cyclise to form compounds containing pentacovalent phosphorus and they also form salts with strong acids e.g. nitric acid trifluoroacetic acid and/or hydrochloric acid.

Preparation of phosphoranylidene compounds

The phosphonium compounds according to the invention may be converted into the corresponding phosphoranylidene compounds by abstraction of an acidic proton (e.g. from the exocyclic methylene group at the 3-position), the conversion being depicted by the following equation:

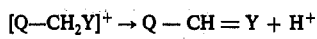

wherein Q has the above-defined meaning.

Formation of the phosphoranylidene compound may be achieved by reacting the phosphonium compound with a base, preferably one stronger than the conjugate base of the phosphonium compound. Suitable bases include alkali metal and alkaline earth metal hydroxides, carbonates and hydrogen carbonates e.g. sodium hydroxide or sodium hydrogen carbonate; disodium hydrogen phosphate; and hydrides e.g. sodium hydride.

Other bases which may be used to generate phosphoranylidene compounds include phosphoranylidenes more basic than the phosphoranylidene compound being produced; the conjugate bases of dimethylsulphoxide, dimethylacetamide and dimethylformamide; tertiary nitrogen bases e.g. pyridine or trialkylamines such as triethylamine; the sodio or lithio derivatives of hexamethyldisilazane, onium and alkali metal alkoxides and fluorides; and alkylene oxides in the presence of halide ion e.g. ethylene oxide or propylene oxide in the presence of, for example, bromide ion.

The use of a base at this stage in conjunction with a ceph-2-em compound may convert the cephalosporin compound to a ceph-3-em compound. This enables a convenient isomerisation to be simultaneously effected.

Formation of the phosphoranylidene compound is generally accompanied by a deepening or generation of colour, for example when starting from a solution of an onium compound the solution yellows or reddens as the phosphoranylidene compound is formed, and a strong $\lambda_{max}$ appears at 388 nm., with dwindling of a weaker band at 275 nm, associated with the onium salt. Compounds with phenyl-phosphorus bonds give rise to a peak in their infrared absorption at about 1450 cm.$^{-1}$.

The phosphoranylidene compounds are novel compounds and constitute a further feature of the invention.

The phosphoranylidene compounds may be coupled with compounds containing carbonyl groups to yield the compounds of general formula (I).

It is not necessary to isolate the phosphoranylidene compound in order to carry out the coupling reaction with the carbonyl compound. The phosphoranylidene compound may be formed in situ from the phosphonium compound and a base as desired above and coupled in situ with the desired carbonyl compound.

The carbonyl compound may, for example, be an aldehyde or ketone e.g. formaldehyde, acetaldehyde, propionaldehyde, butyraldehyde, glycolaldehyde and glyoxylic esters, for example t-butyl glyoxylate. The resulting compounds may exist, where appropriate as trans and cis isomers.

The coupling reaction may be catalysed by a weak organic acid such as benzoic acid.

The reaction with the carbonyl compound may be carried out by vigorously stirring the components together, e.g. at a temperature of from −30° to +100° C. When the reaction is effected at a temperature at which one or more reactants may volatilise a closed system may be used. The reaction may be effected in an inert or relatively inert solvent, for example, a halogenated hydrocarbon, e.g. methylene chloride; a hydrocarbon e.g. benzene; an acyclic or cyclic ether e.g. diethyl ether, tetrahydrofuran or dioxan; dimethylsulphoxide; an amide e.g. dimethylformamide or dimethylacetamide or hexamethylphosphoramide. The course of the reaction may be followed by observing the reduction in colour of the phosphoranylidene compound or the decrease in the $\lambda_{max}$ at 388 nm.

(B) Preparation of compounds of general formula (I) via 3-formyl cephalosporin compounds.

3-Formyl cephalosporin compounds may be caused to react with phosphorane ylids to yield compounds of general formula (I).

The 3-formyl cephalosporin compounds used as starting materials may be defined as having the general formula

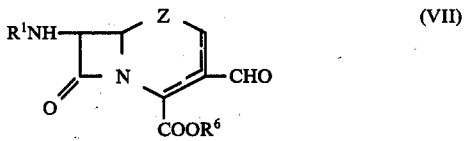

wherein $R^1$, $R^6$ and Z have the above defined meanings.

The 3-formyl cephalosporin compounds may be prepared as described in U.S. Pat. No. 3,351,596; British Pat. No. 1,155,024 or Dutch Patent Application No. 6815631. When it is desired to use a 1-oxide the processes of these Specifications may be adapted to yield the desired 1-oxide. Alternatively, the 1-oxide may be produced directly from the corresponding 3-formyl compound.

Phosphorane ylids which may be used in the reaction with 3-formyl cephalosporins include those having the general formula:

where the $R^7$ groups, which may be the same or different, are each organic groups and $R^3$ and $R^4$, which may be the same or different are each hydrogen atoms or organic groups.

The nature of the groups $R^7$ is not unduly critical since the moiety $=P(R^7)_3$ does not form part of the cephalosporin derivative produced. $R^7$ may, for example, be $C_3$-$C_{10}$ alkyl, $C_5$- or $C_6$-cycloalkyl, aryl e.g. phenyl or substituted phenyl, di(lower alkyl) amino, etc.

The nature of $R^3$ and $R^4$ will depend on the nature of the compound to be produced and the reaction conditions involved. When employing ceph-3-em compounds at least one of $R^3$ and $R^4$ is desirably an electronegative group. When employing ceph-3-em compounds we also prefer that the phosphorane is chosen from those having a pKa (in water: ethanol = 8:2 v/v) of 6.5 - 10 to facilitate the desired reaction.

When it is desired that $R^3$ and/or $R^4$ should be electronegative it may be lower alkoxycarbonyl, aryl-loweralkoxycarbonyl, diaryl loweralkoxycarbonyl, loweralkylcarbonyl, cyano, etc; the aryl moiety may be phenyl or substituted phenyl, e.g. halophenyl or tolyl.

With ceph-2-em compounds, the nature of $R^3$ and $R^4$ is not so critical: they may or may not be electronegative and may be selected from hydrogen, lower alkyl, cycloalkyl, aromatic, e.g. phenyl, etc. groups.

If desired, the ylid may be generated by reaction with a base stronger than the conjugate base of the phosphonium compound. Suitable bases include alkaline earth metal hydroxides, carbonates and hydrogen carbonates e.g. sodium hydrogen carbonate and disodium hydrogen phosphate. Other bases which may be used to generate ylids include the conjugate base of dimethylacetamide and dimethylformamide; tertiary nitrogen bases e.g. pyridine; the sodio or lithio derivatives of hexamethyldisilazane, alkali metal hydrides, alkylene oxides (e.g. ethylene oxide or propylene oxide) which may be potentiated with halide ion, and fluoride ion in an aprotic solvent.

The use of a base at this stage in conjunction with a ceph-2-em compound may convert the cephalosporin compound to a ceph-3-em compound. This enables a convenient isomerisation to be simultaneously effected.

Reaction conditions for (B)

The reaction may be carried out by vigorously stirring the components together, e.g. at a temperature of from −80° to +100° C, preferably from −30° to +30° C. When the reaction is effected at a temperature at which one or more reactants may volatilise, a closed system may be used. The reaction may be effected in an inert or relatively inert solvent, for example, a halogenated hydrocarbon, e.g. methylene chloride; a hydrocarbon e.g. benzene; an acyclic or cyclic ether e.g. diethyl ether, tetrahydrofuran or dioxan; an amide e.g. dimethylformamide or dimethylacetamide or hexamethylphosphoramide. The course of the reaction may be followed by thin layer chromatography and by ultra-violet spectroscopy (in general, the $\lambda_{max}$ shifts to higher wavelengths as the reaction produces chromophoric groups). Disappearance of the 3-formyl group is complete when no fraction on the chromatograms goes red or orange with 2,4-dinitrophenylhydrazone.

Typical products of the process according to this invention are unsaturated esters, e.g.:

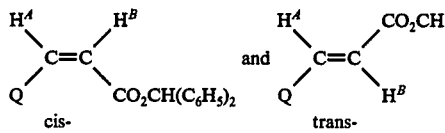

where Q has the above defined meaning. The geometrical isomers may be formed in different proportions, according to the conditions of reaction, and are separable by crystallization and chromatography. The magnetic resonances generally distinguish the isomers, $J_{AB}$ (cis) being ≯13 Hz. and $J_{AB}$ (trans) being 12 to 18 Hz. Further, the methylene protons of the 2-$CH_2$- group in the cis-isomers give a clear AB-quartet, J ca. 18 Hz. whereas this quartet in the trans-isomers collapses, times to a singlet.

N-Deacylation

The product of (A) or (B) may be N-deacylated to yield the corresponding 7β-amino compound.

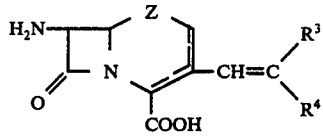

(wherein $R^3$, $R^4$ and Z have the above defined meanings) or a derivative (e.g. ester, salt or salt of ester) thereof. Acid addition salts e.g. with nitric acid or a hydrocarbyl sulphonic acid, may be formed with the free 4-COOH compound or ester thereof. Examples of hydrocarbyl sulphonic acids include alkylbenzene sulphonic acids, e.g. p-toluene sulphonic acid, and lower alkane sulphonic acids, e.g. methane sulphonic acid.

Suitable methods of N-deacylating cephalosporin derivatives having 7β-acylamido groups are described in British Pat. Nos. 1,041,985 and 1,119,806; Belgian Pat. No. 719,712 and in South African Patent Specification Nos. 68/5048 and 68/5327. Another method of N-deacylation which may be used is acid catalysis. For example, N-deformylation of a 7β-formamido group may be effected with a mineral acid at a temperature of minus 15° to +100° C, preferably +15 to 40° C. N-deformylation may be effected with the aid of a Lewis acid in a lower alkanol, preferably under substantially anhydrous conditions.

C. Acylation

Acylation of a compound of formula (IX) (or ester, salt or salt-ester thereof), may be effected with any convenient acylation agent such as for example, an acid halide (e.g. chloride or bromide), an anhydride or mixed anhydride, e.g. with pivalic acid or formed with a haloformate, e.g. a lower alkylhaloformate, or an active ester or azide; alternatively, the acid itself can be used, together with an esterifying agent, e.g. carbonyldiimidazole or a carbodiimide such as N,N′-diethyl-, dipropyl-, or -diisopropylcarbodiimide, or preferably N,N′-dicyclohexylcarbodiimide.

Acylation with an acid halide may be effected in the presence of an acid binding agent, e.g. a tertiary amine such as triethylamine, dimethylformamide, dimethylaniline; an inorganic base such as calcium carbonate or sodium bicarbonate; or an oxirane which binds hydrogen halide liberated in the acylation reaction. The oxirane is preferably a lower-1,2-alkylene oxide e.g. ethylene oxide or propylene oxide.

According to a preferred embodiment of the process according to the invention there is provided a process for the preparation of compounds of the formula

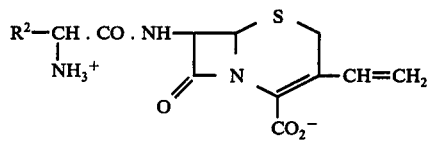

wherein $R^2$ has the above defined meaning, which comprises acylating a compound of the formula

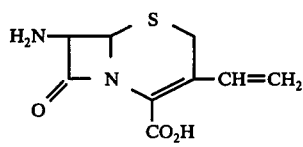

(or an ester, salt or salt-ester thereof) with a compound of the formula

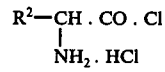

in the presence of an acid-binding agent.

Protection of amino groups

When the 7β-acylamido group contains an amino group it will be necessary to protect this during the various reaction stages. The protecting group is conveniently one which can be removed by hydrolysis without affecting the rest of the molecule, especially the lactam and 7β-amido linkages. The amine protecting group and the esterifying group at the 4-COOH position can be removed using the same reagent. An advantageous procedure is to remove both groups at the last stage in the sequence. Protected amine groups include urethane, arylmethyl (e.g. trityl) amino, arylmethyleneamino, sulphenylamino or enamine types. Such groups can in general be removed by one or more reagents selected from dilute mineral acids e.g. dilute hydrochloric acid, concentrated organic acids, e.g. concentrated acetic acid, trifluoroacetic acid, and liquid hydrogen bromide at very low temperature, e.g. −80° C. A convenient protecting group is the t-butoxycarbonyl group, which is readily removed by hydrolysis with dilute mineral acid, e.g. dilute hydrochloric acid, or preferably with a strong acid (e.g. formic acid, trifluoroacetic acid or liquid HF) e.g. at a temperature of 0°-40° C., preferably at room temperature (15°-25° C).

Another convenient protecting group is the 2,2,2-trichloroethoxycarbonyl group which may be split off by an agent such as zinc/acetic acid, zinc/formic acid, zinc/lower alcohols or zinc/pyridine. The $NH_2$ group may also be protected as $NH_3+$ by using the amino acid halide as its hydrohalide under conditions in which the amino group remains protonated.

Typical protecting groups and their methods of removal are illustrated in the following table:

| Type | Example | Usual Name and Analoques etc. | Usual Method of Removal |
| --- | --- | --- | --- |
| Urethane | 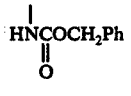 | Benzyloxycarbonyl, p-Methoxy | HBr/AcOH (Neat)<br>$CF_3COOH$ (Neat)<br>Liq. HBr at −80° C |
| Urethane | 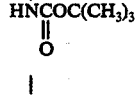 | t-Butoxycarbonyl | Dil. acid (HCl)<br>$CF_3COOH$ (Neat) |
| Urethane | 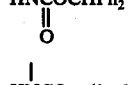 | Diphenylmethoxycarbonyl | $CF_3COOH$ (Neat)<br>Dil. HCl etc. |
| Urethane | 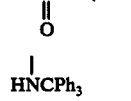 | 1-Adamantyloxycarbonyl | Dil. HCl |
| Arylmethyl | 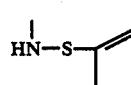 | Trityl | AcOH + $H_2O$<br>Dil. HCl |
| Sulphenyl | 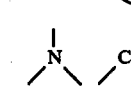 | o-Nitrophenylsulphenyl,<br>p-nitro- | Dil. HCl<br>NaI or<br>$Na_2S_2O_3$<br>pH 2-4 |
| Enamine | 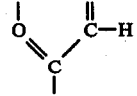 | β-Dicarbonyl<br>R=OEt Ethyl acetoacetate<br>R=$CH_3$ Acetylacetone<br>R=Ph Benzoylacetone<br>R=OMe Methyl acetoacetate<br>R=$C_2H_5$ Propionylacetone<br>and many other β-diketones | Acid labile in<br>varying degree<br>Dil. AcOH or<br>HCl etc. |
| Arylmethylene | 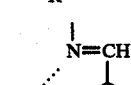 | Anil (similar to β-dicarbonyl)<br>from Salicylaldehyde<br>5-chlorosalicylaldehyde<br>3,5-dichlorosalicylaldehyde<br>2-hydroxy-1-naphthaldehyde<br>3-hydroxy-pyridine-4-aldehyde | Dil. HCl<br>Formic acid |
| Onium Urethane | 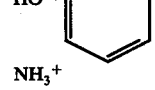 | β,β,β-trichloroethoxy-<br>carbonyl | Base<br>Reducing agents<br>e.g.<br>Zn/acetic acid |

D. Subsequent reactions

Where the resultant compound contains a sulphinyl group at the 1-position this may be reduced by any convenient means. This may, for example, be effected by reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid tetrahydrofuran, dioxan, dimethylformamide or dimethylacetamide. The reaction may be effected at a temperature of −20° to +50° C.

Alternatively, reduction of the 1-sulphinyl group may be effected by phosphorus trichloride or tribromide in solvents such as methylene chloride, dimethylformamide or tetrahydrofuran, preferably at a temperature of −20° C to +50° C.

Where the resultant compound is a ceph-2-em compound, the desired ceph-3-em compound may be obtained by treatment of the former with a base e.g. a base of the type used in the preparation of the phosphoranylidene compounds.

Removal of any groups protecting any amino or carboxyl groups may be effected as desired above.

Administration

The compounds according to the invention may be formulated for administration in any convenient way, by analogy with other antibiotics and the invention therefore includes within its scope a pharmaceutical composition comprising a compound of formula (I) or a non-toxic derivative e.g. salt thereof (as herein defined) adapted for use in human or veterinary medicine. Such compositions may be presented for use in conventional manner with the aid of any necessary pharmaceutical carriers or excipients.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions., syrups, elixirs, etc. or may be presented as a dry product, for reconstitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles which may include edible oils, for example, almond oil, fractionated coconut oil, oily esters, propylene glycol, or ethyl alcohol; preservatives, for example, methyl or propyl p-hydroxybenzoates or sorbic acid. Suppositories will contain conventional suppository bases, e.g. cocoa butter or other glyceride.

Compositions for injection may be presented in unit dose form in ampoules, or in multidose containers with an added preservative. The compositions may take such forms as suspensions, solutions, emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops, etc. Topical applications may be formulated in hydrophobic or hydrophilic bases as ointments, creams, lotions, paints, powders, etc.

For veterinary medicine the composition may, for example, be formulated as an intramammary preparation in either long acting or quick-release bases.

The compositions may contain from 0.1% upwards, e.g. 10-99%, preferably from 10-60% of the active material, depending on the method of administration. Where the compositions comprise dosage units, each unit will preferably contain 50-500 mg. of the active ingredient. The dosage as employed for adult human treatment will preferably range from 100-300 mg. for instance 1500 mg. per day, depending on the route and frequency of administration.

The compounds according to the invention may be administered in combination with other therapeutic agents such as antibiotics, for example, other cephalosporins, the penicillins or tetracyclines.

In order that the invention may be well understood the following Examples are given by way of illustration only.

In the Examples, unless otherwise stated
(1) Ultra-violet (uv) spectra were measured on solutions in ethanol.
(2) Infra-red (ir) spectra were measured on mulls in Nujol.
(3) Optical rotations were determined at 19 to 30° at concentrations in the range 0.5 to 1.5% as solutions in dimethylsulphoxide. Where other solvents were used the same concentration range applied.
(4) Solutions were dried over anhydrous magnesium sulphate.
(5) All grades of Kieselgel were supplied by Merck AG Darmstadt, Germany.
(6) Proton magnetic resonance (PMR) spectra were determined at 60 or 100 MHz. The signs of the coupling constants (J) are not assigned. Signals are assigned as singlets (s), doublets (d), double doublets (dd), triplets (t), quartets (q), double quartets (dq), AB-quartets (AB-q), quintets (qu) and multiplets (m).

System A is descending n-propanol; water = 7:3, on Whatman No. 1 Paper at room temperature. System B is n-butanol:ethanol:water = 4:1:5, equilibrated at room temperature, the upper phase being used as developer in descending manner, in equilibrium with lower phase, on Whatman 3MM paper buffered to pH 6 with 0.05M sodium dihydrogen phosphate.

System C is ethyl acetate: n-butanol: 0.1M-sodium acetate pH 5 = 8:1:8, equilibrated at 38° C, the upper phase being used as developer in descending manner, in equilibrium with lower phase at 38°, on No. 1 Whatman paper buffered to pH 5 with 0.1M sodium acetate.

Light petroleum was the fraction, b.p. 40° to 60°. Methylene chloride was dried on Woelm Grade I basic alumina. Thin-layer chromatography was carried out upwards on Merck silica plates developed with benzene:ethyl acetate = 4:1, or in these conditions.

System D Merck $GF_{254+366}$ plates, with the upper phase of Solvent Mixture B for development. System E On the plates of System D, with benzene:ethyl acetate = 5:1 for development. Unless otherwise stated $R_F$ values are using System E. System F As System E, but with benzene:ethyl acetate = 1:1 as solvent.

These abbreviations are used for the appearances of the spots: s, strong; m, medium; f, faint; v, very.

As far as possible, analytical values for solvates were confirmed by the inspection for the appropriate features in the spectra.

$R_P$ represents the $R_F$ value divided by that of 3-acetoxymethyl-7β-(phenylacetamido) ceph-3-em-4-carboxylic acid.

$R_T$ represents the $R_F$ value divided by that of 3-acetoxymethyl-7β-(2-thineylacetamido)ceph-3-em-4-carboxylic acid.

The conditions for electrophoresis are those described by Cocker et al., J. Chem. Soc. 1965, 5015.

The Examples are divided into the following sections:

A Preparation of cephalosporins having a vinyl or substituted vinyl group at the 3-position via phosphranylidene cephalosporin compounds.

(i) Preparation of compounds of the 3-CH$_2$Y type.

(ii) Preparation of compounds of the 3-CH=Y type from compounds of the 3-CH$_2$Y type.

(iii) Preparation of vinyls from compounds of the 3-CH=Y type.

B Preparation of cephalosporins having a vinyl or substituted vinyl group at the 3-position via 3-formyl cephalosporin compounds

SECTION A (i)

EXAMPLE 1:

[4-Diphenylmethoxycarbonyl-7β-(2-thienylacetamido)-ceph-3-em-3-ylmethyl]-triphenylphosphonium iodide A solution of diphenylmethyl 3-iodomethyl-7β-(2-thienylacetamido)ceph-3-em-4-carboxylate (30 g.,) Rf 0.6 in ethyl acetate (500 ml.) was stirred in the dark at room temperature and treated, over 45 minutes, with a solution of triphenylphosphine (24.9 g., ca. 2 equivs.) in ethyl acetate (150 ml.). The mixture was stirred for a further 60 minutes at 0°, and the precipitated solid collected by filtration. The solid was washed with ethyl acetate and dried in vacuo to give the phosphonium iodide (31.7 g., 74.5%), Rf 0.0, m.p. 142°–146° (decomp.), $[\alpha]_D$ + 10° (tetrahydrofuran), $\lambda_{max}$ 269 nm (ε9,400) and 276 nm (ε8,600) $\nu_{max}$ (CHBr$_3$) 3350 (NH), 1780 (β-lactam), 1710 (CO$_2$R), 1680 and 1505 (CONH), and 1445 (P-C(aryl)) cm$^{-1}$, τ (CDCl$_3$) 4.39 (C$_{(7)}$-H,dd,J 4.5 and 9 Hz), 5.19 (C$_{(6)}$-H, d, J 4.5 Hz) 4.75 and 4.85 (CH$_2$-P, four major signals of two AB-q J$_{P-H}$ 16 Hz), 6.05 and 6.68 (C$_{(2)}$- CH$_2$ two dd, J$_{H-H}$ 18 Hz, J$_{P-H}$ 3-4 Hz). [Found: C, 59.3; H, 4.5; I, 13.4; N, 2.6; P, 3.4; S, 7.3. C$_{45}$H$_{38}$IN$_2$O$_4$PS$_2$ (892.8) requires C, 60.5; H, 4.3; I, 14.2; N, 3.1; P, 3.5; S, 7.2%].

EXAMPLE 2

[4-Diphenylmethoxycarbonyl-7β-(2-thineylacetamido) ceph-3-em-3-ylmethyl]-triphenylphosphonium bromide A solution of diphenylmethyl 3-bromomethyl-7β-(2-thienylacetamido)ceph-3-em-4-carboxylate (300mg.), Rf 0.6 in benzene (5 ml.) was treated with triphenylphosphine (140 mg.) and the total warmed to 50° for 10 minutes. After the mixture had stood at room temperature for a further hour it was diluted with ether and the precipitated solid was collected by filtration. This material was washed thoroughly with ethyl acetate and ether, and on drying in vacuo gave the phosphonium bromide (250 mg.) Rf 0.0 m.p. 135° – 140° C (decomp.) $[\alpha]_D$ + 12° (tetrahydrofuran), $\nu_{max}$(CHBr$_3$) 3410 (NH), 1784 (β-lactam), 1710 (CO$_2$R), 1680 and 1515 (CONH) and 1442 (P-C aryl.) cm.$^{-1}$ τ (CDCl$_3$) 4.38 (C$_{(7)}$-H, dd, J 4.5 and 9 Hz), 5.19 (C$_{(6)}$-H, d, J 4.5 Hz), 4.62 and 4.8 (CH$_2$- P, two d, J$_{P-H}$ 16 Hz), 6.02 and 6.6 (C$_{(2)}$- CH$_2$, two dd, J$_{H-H}$ 18 Hz and J$_{P-H}$ 3-4Hz).

EXAMPLE 3

[4-Diphenylmethoxycarbonyl-7β-(2-thienylacetamido) ceph-3-em-3-ylmethyl]-triphenylphosphonium chloride Triphenylphosphine (123 mg. 0.5 m mole.) and diphenylmethyl 3-chloromethyl-7β-(2-thienylacetamido) ceph-3-em-4-carboxylate (266 mg., 0.5 m mole) were melted together for 1 hour under nitrogen at 114°–130°. The black-red product with triturated with tetrahydrofuran to give a brown solid (A) (150 mg.), m.p. 103°–120° (a 1% solution in tetrahydrofuran containing about 20% dimethylsulphoxide was too opaque for polarimetry), λ$\lambda_{max}$268 nm (ε 10,600), 275 nm (ε 9,700), $\nu_{max}$(CHBr$_3$) 1770, 1707, 1675, 1510, 1430, 1250, and 742 cm$^{-1}$; n.m.r. (CDCl$_3$ and d$_6$ - DMSO at 60 MHz) gave evidence only for aromatic protons and the thienylacetamido-methylene group. A comparison with the physical constants for the analogous phosphonium iodide suggests that this product (A) contained the title compound.

EXAMPLE 4

[4-Diphenylmethoxycarbonyl-7β-(2-thienylacetamido)-ceph-3-em-3-ylmethyl]tri-n-butylphosphonium iodide A solution of diphenylmethyl 3-iodomethyl-7β-(2-thienylacetamido)ceph-3-em-4-carboxylate (4.9 g.) in ethyl acetate (90 ml.) was stirred in the dark at room temperature and treated, over 15 minutes, with a solution of tri-n-butylphosphine (3.1 g., ca. 2 equivs.) in ethyl acetate (50 ml.). The solution was stirred for a further 45 minutes and precipitated into petroleum-ether to give the phosphonium iodide (3.448 g.), m.p. 120°–125° (decomp), $[\alpha]_D$ - 43°(N,N-dimethylformamide), R$_F$ 0.0, inflexion (EtOH) at 259 nm. (ε 7,100), $\nu_{max}$(CHBr$_3$) 3410 (-NH), 1786 (β-lactam), 1708 (ester), and 1686 and 1510 cm.$^{-1}$ (-CONH-), τ (CDCl$_3$) 4.22 (C$_{(7)}$-H, dd, J 5 and 9 Hz.), 4.87 (C$_{(6)}$-H d, J 5 Hz), 5.80 and 6.11 (C$_{(2)}$-CH$_2$, two dd, J$_{H-H}$ 18 Hz., J$_{P-H}$ 3-4 Hz). [Found: C, 55.3; H, 6.0; I, 15.7; N, 3.1; P, 3.7 C$_{39}$H$_{50}$IN$_2$O$_4$PS$_2$ (832.8) requires C, 56.2; H, 6.1; I, 15.1; N, 3.4; P, 3.7%].

EXAMPLE 5

[4-Diphenylmethoxycarbonyl-7β-(2-thienylacetamido)-ceph-3-em-3-ylmethyl] triphenylphosphonium bromide, 1β-oxide A solution of diphenylmethyl 3-bromomethyl-7β-(2-thienylacetamido)ceph-3-em-4-carboxylate 1β-oxide (599 mg., 1 mmole) in methylene chloride (25 ml.) was stirred at room temperature and treated, over 15 minutes, with a solution of triphenylphosphine (787 mg., ca. 3 equivs.) in methylene chloride (5 ml.). The solution was stirred for a further 60 minutes at room temperature, the solvent removed by rotary evaporation, and the residual foam triturated with ethyl acetate to give white crystals of the title compound (752 mg., 87%), R$_F$0.0 m.p. 133° (decomp), $[\alpha]_D$ − 16° (N,N-dimethylformamide) $\nu_{max}$ (CHBr$_3$) 3390 (—NH), 1798 (β-lactam), 1710 (—CO$_2$R), 1690 and 1510 (—CONH—) 1440 (P-C (aryl)) and 1030 cm.$^{-1}$ (S→O), λ$_{max}$ 271 nm. (ε 8,300) and 278 nm. (γ 9,700) τ(CDCl$_3$) 3.96 (C$_{(7)}$-H, dd, J 5 and 10 Hz), 4.40 and 4.56 (CH$_2$-P, two d, J$_{P-H}$ 14 Hz), 4.88 and 6.56 (C$_{(2)}$-CH$_2$, two dd J$_{H-H}$ 19 Hz., J. $_{P-H}$ 3 Hz.), 5.05 (C$_{(6)}$-H, d J 5 Hz.) [Found: C, 61.0; H, 4.4; Br, 8.8;

N, 2.8; P, 3.8. $C_{45}H_{38}BrN_2O_5PS_2$(861.8) requires C, 62.8; H, 4.45; Br, 9.3; N, 3.25; P, 3.6%].

EXAMPLE 6

[4-Diphenylmethoxycarbonyl-7β-(2-thienylacetamido)-ceph-2-em-3-ylmethyl] triphenylphosphonium chloride A solution of diphenylmethyl 3-chloromethyl-7β-(2-thienylacetamido)ceph-2-em-4-carboxylate (2.3 g.) in ethyl acetate (20 ml.) was treated with triphenylphosphine (2.3 g., ca. 2 equivs.) and the mixture refluxed for 5 hours. The solution was cooled and the insoluble product isolated by filtration. This material was precipitated from acetone (containing some chloroform) solution by petroleum-ether to give the phosphonium salt (500 mg.) as an amorphous solid $[\alpha]_D + 68.5°$(CHCl$_3$), $\lambda_{max.}$ (CHCl$_3$) 269.5 and 276.5 nm. ($\epsilon$ 8,880 and 7,620), $\nu_{max.}$ (CHBr$_3$) 3440 (NH), 1780 (β-lactam), 1680 and 1510 (—CONH—), and 1445 (P-C aryl) cm, $^{-1}$, $\tau$(CDCl$_3$) 3.61 (C$_{(2)}$-H), 4.4 (C$_{(7)}$-H, dd, J 4.5 and 9 Hz), 4.75 (C$_{(6)}$-H, not well resolved, 5.04 and 5.18 (CH$_2$-P, part of two AB-q, J$_{P-H}$ 13 Hz.).

EXAMPLE 7

Diethyl[4-diphenylmethoxycarbonyl-7β-(2-thienylacetamido)ceph-3-em-3-ylmethyl]phosphonate A solution of diphenylmethyl 3-iodomethyl-7β-(2-thienylacetamido)ceph-3-em-4-carboxylate (315 mg.) in ethyl acetate (4ml.) was treated with triethylphosphite (0.3 ml.) and the mixture refluxed for 1½ hours. Dilution of the solution with petroleum ether (40°-60° C fraction) gave the phosphonate (270 mg.) as an amorphous solid, $[\alpha]_D + 2.5°$ (CHCl$_3$), inflexions at 234 and 264 nm. ($\epsilon$ 13,960 and 6,850) $\nu_{max.}$(CHBr$_3$) 1775 (β-lactam), 1718 (CO$_2$R), 1675 and 1508 (CONH) cm$^{-1}$, $\tau$ (CDCl$_3$) 4.25 (C$_{(7)}$-H, dd, J 4.5 and 9 Hz.), 5.05 (C$_{(6)}$-H, d, J 4.5 Hz), 6.07 and 8.82 (P-O-C$_2$H$_5$, qu and t, J$_{H-H}$ = J$_{P-H}$ 7.5 Hz.), 6.50 (C$_{(2)}$—CH$_2$), and 6.55 and 6.94 (—CH$_2$—P—, two quartets, J$_{H-H}$ 13 Hz., J$_{P-H}$ 24 Hz.).

EXAMPLE 8

[4-Diphenylmethoxycarbonyl-7β-(2-thienylacetamido)-ceph-3-em-3-ylmethyl] tri-n-butylphosphonium bromide A solution of diphenylmethyl 3-bromomethyl-7β-(2-thienylacetamido)ceph-3-em-4-carboxylate (583 mg.) in ethyl acetate (5 ml.) was treated with a solution of tri-n-butylphosphine (0.3 ml., ca. 2 equivalents) in ethyl acetate (2 ml.). After 10 minutes at room temperature the mixture was diluted with petroleum ether to give the phosphonium salt (690 ml.) as an amorphous solid, m.p. 65° - 70° $[\alpha]_D^{23} - 35°$ (c 1.0 CHCl$_3$), inflexion at 237 nm. ($\epsilon$ 12,460) and 258 nm. ($\epsilon$ 6,550), $\nu_{max}$ 1770 (β-lactam), 1702 (CO$_2$R), 1670 and 1530 (CONH) and 693 (phenyl) cm.$^{-1}$; $\tau$ (CDCl$_3$) 4.22 (C$_{(7)}$-H dd, J 4.5, 9 Hz.), 4.93 (C$_{(6)}$-H, d, J 4.5 Hz.), 5.5 to 6.1 (C$_{(2)}$-CH$_2$ and =C—CH$_2$P+, unresolved m), 7.62 (P+CH$_2$CH$_{CH2}$CH$_3$, m), 8.55 (P+CH$_2$CH$_2$CH$_2$CH$_3$, m) and 9.1 (P+CH$_2$CH$_2$CH$_2$CH$_3$, d, J 6 Hz.).

Treatment of this material in ethanol solution with ethoxycarbonylmethylenetriphenylphosphorane (pKa 8.95) gave no chromophore at 388 nm corresponding to the phosphorane derived from the title compound. However, treatment with carbamoylmethylenetriphenylphosphorane (pKa 11) gave the chromophore at 388 nm, corresponding to the phosphorane (pKa values in 80%-aqueous ethanol determined by S. Fliszar, R. F. Hudson and G. Salvadori, Helv.Chim.Acta., 1963 46,1580).

EXAMPLE 9

[7β-Formamido-4-(2,2,2-trichloroethoxycarbonyl)-ceph-3-em-3-ylmethyl]triphenylphosphonium bromide 1β-oxide A solution of 2,2,2-trichloroethyl 3-bromomethyl-7β-formamidoceph-3-em-4-carboxylate 1β-oxide [334 mg. prepared as described in Preparation A 3(a) and (b)(i) and Example B3(i) of copending Application No. (Ceph 118/131/132/143)] in tetrahydrofuran (6 ml.) was treated with a solution of triphenylphosphine (390 mg. ca. 2 equivalents) in tetrahydrofuran (3 ml.). After 30 miniutes at room temperature the solvent was removed in vacuo. The residue was washed thoroughly with ether (to remove triphenylphosphine) to give the phosphonium bromide (514 mg.) as an amorphous solid, m.p. 159°-161° (decomp.), $[\alpha]_D + 11.3°$ (CHCl$_3$), $\lambda_{max}$ (CHCl$_3$) 270 nm. ($\epsilon$ 9,780) 277 nm. ($\gamma$ 10,370) and 290 nm. ($\epsilon$ 8,530), $\nu_{max}$(CHBr$_3$) 3360 (NH), 1790 (β-lactam), 1720 (CO$_2$R), 2730, 1680, and 1500 (HCONH), 1435 (P-aryl) and 1020cm$^{-1}$ (SO),$\tau$(DMSO-d$_6$) 1.5 (NH, d, J 9 Hz.), 1.82 (HCONH), 4.02 (C-7 H, dd, J 4.5 and 9 Hz.), 4.69 (C-6 H, d, J 4.5 Hz), 4.79 (CH$_2$-P, two broad s, J$_{P-H}$ 17 Hz), 5.19 and 5.44 (CH$_2$CCl$_3$, AB-q, J 12 Hz) and 6.04 (C-2 CH$_2$ broad [degenerate AB-q]).

EXAMPLE 10

(4-t-Butoxycarbonyl-7β-formamidoceph-3-em-3-ylmethyl)-triphenylphosphonium bromide 1β-oxide A solution of t-butyl 3-bromomethyl-7β-formamidoceph-3-em-4-carboxylate 1β-oxide [786 mg. prepared as described in Preparation A4(a), (b)(i) and (c) and Example B4(i) of copending Application No. (ceph 118/131/132/143)] in tetrahydrofuran (10 ml.) was treated with a solution of triphenylphosphine (1.05 g., ca 2 equivalents) in tetrahydrofuran (5 ml.). After 1 hour at room temperature the precipitated solid was collected by filtration and washed with ether to give the phosphonium bromide (800 mg.) as an amorphous solid, m.p. 169°-171° (decomp.), $[\alpha]_D + 18.1°$ (CHCl$_3$), $\lambda_{max.}$ (CHCl$_3$) 270 nm. ($\epsilon$ 10,100) and 277 nm. ($\epsilon$ 10,540) and inflexion at 290 nm. ($\epsilon$ 8,850), $\nu_{max}$(CHBr$_3$) 3360 (NH), 1790 (β-lactam), 1700 (CO$_2$R), 2740, 1698, and 1502 (HCONH), 1440 (P-aryl) and 1029 cm.$^{-1}$ (SO), $\tau$ (DMSO-d$_6$) 1.54 (NH, d, J 9 Hz.), 1.8 (HCONH), 4.03 (C$_{(7)}$-H, dd, J 4.5,9 Hz.), 4.70 (C$_{(6)}$-H, d J 4.5 Hz.), 4.72 and 4.88 (CH$_2$-P, centres of two AB-q, J$_{H-H}$ ca. 15 Hz.), 6.15 (C$_{(2)}$, broad s), and 8.71 (t-butyl).

EXAMPLE 11

[7β-Phenylacetamido-4-(2,2,2-trichloroethoxycarbonyl)-ceph-3-em-3-ylmethyl]-triphenylphosphonium bromide 1β-oxide A solution of triphenylphosphine (52 mg., 2 equiv.) in methylene chloride (0.5 ml.) was added to a solution of 2,2,2-trichloroethyl 3-bromomethyl-7β-phenylacetamidoceph-3-em-4- carboxylate 1β-oxide [56 mg., 0.1 mmole prepared as described in Preparation A2(i) and Example B2(i) of copending Application No. (ceph 118/131/132/143)], in methylene chloride (0.5 ml.). After 30 minutes has elapsed, TLC (methylene chloride -acetone; 4:1) showed that no starting bromo-ester remained and that a new product, R$_F$ 0.0, had resulted. The solvent was evaporated and the residue foam was triturated with ethyl acetate to give the title phosphonium salt, m.p. 150°–154° (dec.), $\lambda_{max.}$ 268 nm ($E_{1cm.}^{1\%}$ 101) and 275 ($E_{1cm.}^{1\%}$ 1010) $\nu_{max.}$ (CHBr$_3$) 3400 (NH), 1803 (azetidin-2-one), 1732 (CO$_2$R), 1692 and 1510 (CONH) and 1034 cm.$^{-1}$ (SO).

EXAMPLE 12

[4-t-Butoxycarbonyl-7β-phenoxyacetamidoceph-3-em-3-yl-methyl]-triphenylphosphonium Bromide A solution of triphenylphosphine (1.95 g, 2 equiv.) in ethyl acetate (6 ml) was added to a solution of t-butyl 3-bromomethyl-7β-phenoxyacetamidoceph-3-em-4-carboxylate (1.80 g, 3.72 mmole) in ethyl acetate (4 ml.). The mixture was stirred for 1 hour, and the precipitated solid was filtered off, washed with ether and dried to give the title phosphonium salt (2.42 g, 87.5%), m.p. 144° to 146°, $[\alpha]_D^{22}$ +31° (C 0.95; Me$_2$SO), $\lambda_{max.}$ (EtOH) 268 nm (ε 11,300) and 275 nm (ε 10,400), $\nu_{max.}$ (Nujol) 3400 (NH), 1778 (azetidin-2-one), 1692 and 1520 (CONH), 1690 (CO$_2$R) and 1430 cm$^{-1}$ (P$^+$-C$_6$H$_5$), τ (Me$_2$SO-d$_6$) 0.89 (1H, d, j 8 Hz; NH), 2.66 and 2.99 (2H and 3H, 2 m; C$_6$H$_5$O), 4.29 (1H, centres of two AB-quartets, $J_{H-H}$ 15 Hz, $J_{P-H}$ 16 Hz; C$_3$-CH$_2$P$^+$), 5.33 (2H, s; C$_6$H$_5$OCH$_2$), 8.76 (9H, s; CO$_2$C(CH$_3$)$_3$).

EXAMPLE 13

[4-t-Butoxycarbonyl-7β-phenoxyacetamidoceph-3-em-3-ylmethyl]-triphenylphosphonium Bromide, 1β-oxide A solution of t-butyl 3-bromomethyl-7β-phenoxyacetamidoceph-3-em-4-carboxylate, 1β-oxide (500 mg, 1 mmole) and triphenylphosphine (525 mg, 2 equiv.) in a mixture of methylene chloride (4 ml) and tetrahydrofuran (3 ml) was stirred at ca. 25° for 1 hour. The precipitated solid was filtered off, ashed with ether and dried to give the title phosphonium salt, 1β-oxide (631 mg, 83%), m.p. 192°, $[\alpha]_D^{24.5}$ + 9.7° (C 1.03; Me$_2$SO), $\lambda_{max.}$ (EtOH) 269.5 nm (ε 10,000) and 276 nm (ε 10,800), $\nu_{max.}$ (CHBr$_3$) 3375 (NH), 1794 (azetidin-2-one), 1702 (CO$_2$R), 1690 and 1518 (CONH), 1440 (P$^+$-C$_6$H$_5$) and 1030 cm$^{-1}$ (S→O), τ (Me$_2$SO-d$_6$) 1.81 (1H, d, J 9.5 Hz; NH) 2.66 and 2.99 (2H and 3H, 2m; C$_6$H$_5$O), 3.97 (1H,dd, J 9.5 and 5 Hz; C$_7$-H), 4.75 and 4.91 (2H, centres of 2 AB -quartets, $J_{H-H}$ 15 Hz, $J_{P-H}$ ca15 Hz; C$_3$-CH$_2$P), 4.75 (1H,d, J 5Hz; C$_6$-H), 6.16 (2H, broad s; C$_2$-H$_2$), 8.76 (9H, s; CO$_2$C(CH$_3$)$_3$) (Found: C, 59.6; H, 5.1; Br, 11.7; N, 3.2. C$_{38}$H$_{38}$BrN$_2$O$_6$PS (761.7) requires C, 59.9; H, 5.0; Br, 10.5; N, 3.7%).

EXAMPLE 14

(a)
2,2,2-Trichloroethyl-3-Bromomethyl-7β-phenylacetamidoceph-3-em-4-carboxylate A solution of 2,2,2-trichloroethyl 3-bromomethyl-7β-phenylacetamidoceph-3-em-4-carboxylate, 1β-oxide (560 mg, 1 mmole) in dry methylene chloride (25 ml) was cooled to below −20° and a solution of phosphorus tribromide (0.14 ml, 1.5 equiv.) in methylene chloride (ca. 1.3 ml), was added over a period of 15 minutes. The mixture was kept at −20° for a further 15 minutes, and then washed with 4%-sodium hydrogen carbonate solution and water (2 × 10 ml. of each), dried (MgSO$_4$), and evaporated to give the title ester as a pale-yellow foam (419 mg, 77%), $[\alpha]_D$ − 33.6° (C 1.06; CHCl$_3$), $\lambda_{max.}$ (EtOH) 278 nm (ε 7,850), $\nu_{max.}$ (CHBr$_3$) 3430 (NH), 1790 (azetidin-2-one), 1740 (CO$_2$R) and 1682 and 1508 cm$^{-1}$ (CONH), τ (CDCl$_3$) 2.69 (5H, s; C$_6$H$_5$), 3.60 (1H,d, J 10 Hz; NH), 4.16 (1H,dd, J 10 and 5 Hz; C$_7$H), 4.98 and 5.22 (2H, AB-q, J 12 Hz; CH$_2$CCl$_3$), 5.00 (1 H,d, J 5 Hz; C$_6$-H), 5.60 (2H, s, C$_3$-CH$_2$Br), 6.23 and 6.60 (2H, AB-q, J 18 Hz; C$_2$-H$_2$), 6.38 (2H, s; C$_6$H$_5$CH$_2$).

(b)
[7β-Phenylacetamido-4-(2,2,2-trichloroethoxycarbonyl)ceph-3-em-3-ylmethyl]-triphenylphosphonium Bromide A solution of triphenylphosphine (4.98 g, 2 equiv.) in ethyl acetate (30 ml) was added over a period of 15 minutes to a stirred solution of 2,2,2-trichloroethyl 3-bromomethyl-7β-phenylacetamidoceph-3-em-4-carboxylate (5.2 g, ca. 9.5 mmole) in ethyl acetate. The mixture was stirred in the absence of light for 2 hours when the precipitated solid was filtered off, washed with ethyl acetate and dried to give the title phosphonium salt (6.17 g, 81%), $\lambda_{max.}$ (EtOH) 268.5 nm (ε 10,450) and 275.5 nm (ε 10,050), $\nu_{max.}$ (CHBr$_3$) 3412 (NH), 1784 (azetidin-2-one), 1722 (CO$_2$R), 1678 and 1498 (CONH) and 1440 cm$^{-1}$ (P$^+$-C$_6$H$_5$).

EXAMPLE 15

(a) t-Butyl 3-Bromomethyl-7β-formamidoceph-3-em-b 4-carboxylate

A solution of t-butyl 3-bromomethyl-7β-formamidoceph-3-em-4-carboxylate, 1β-oxide (3.95 g, 10 mmole) in dry methylene chloride (85 ml) was cooled to −20° and a solution of phosphorus tribromide (1.43 ml, 15 mmole) in dry methylene chloride (9 ml) was added. The mixture was kept at −20° for 17 minutes, when 5% sodium hydrogen carbonate solution was added until the mixture was alkaline. The organic layer was washed with water, dried (MgSO$_4$), and evaporated to give the title ester as a cream foam (3.45 g, 91%), $[\alpha]_D^{22}$ + 19.3° (C 0.91; CHCl$_3$), $\lambda_{max.}$ (EtOH) 270.5 nm (68 5,300), $\nu_{max.}$ (CHBr$_3$) 3420 (NH), 1790 (azetidin-2-one), 1720 (CO$_2$R) and 1700 and 1505 cm$^{-1}$ (CONH), τ (CDCl$_3$) 1.76 (1H, s; CHO), 3.25 (1H,d,J 9Hz; NH), 4.15 (1H,dd,J 9 and 5 Hz; C$_7$-H), 5.02 (1H,d, J 5 Hz; C$_6$-H), 5.61 (2H, s; C$_3$-CH$_2$Br), 6.30 and 6.54 (2H, AB-q, J 18 Hz; C$_2$-H$_2$), 8.44 (9H,s; CO$_2$C(CH$_3$)$_3$).

(b)
[4-t-Butoxycarbonyl-7β-formamidoceph-3-em-3-ylmethyl]-triphenylphosphonium Bromide (i) A solution of t-butyl 3-bromomethyl-7β-formamidoceph-3-em-4-carboxylate (340 mg, 0.9 mmole) in ethyl acetate (5ml) was treated with a solution of triphenylphosphine (520 mg. 2 mmole) in ethyl acetate (5 ml). The mixture was warmed to 50° for a few minutes and then stored at 23° for 1½ hours. The precipitated solid was filtered off, washed with ether, and dried to give the title phosphonium salt (270 mg, 47%), $\lambda_{max.}$ (EtOH) 269 nm (ε 9,350) and 275.5.nm (ε 9,200), $\nu_{max.}$ (CHBr$_3$) 3430 (NH), 1790 (azetidin-2-one), 1706 (CO$_2$R), 1700 and 1510 (CONH) and 1445 cm$^{-1}$ (P$^{30}$-C$_6$H$_5$), τ (Me$_2$SO-d$_6$) 0.85 (1H,d, J 8.5 Hz; NH), 1.84 (1H, s; CHO), 4.27 (1H, dd, J 8.5 and 5 Hz; C$_7$-H), 4.68 (1H, d, J 5Hz; C$_6$-H), 4.79 and 4.95 (2H, centres of two AB-quartets, $J_{H-H}$ 14 Hz, $J_{P-H}$ 16 Hz; C$_3$-CH$_2$P$^{30}$), 8.77 (9H, s; CO$_2$C(CH$_3$)$_3$).

(ii) A solution of [4-t-butoxycarbonyl-7β-formamidocpeh-3-em-3-ylmethyl]-triphenylphosphonium bromide 1β-oxide (327.5 mg. 0.5 mmole) in dry methylene chloride (3 ml) was cooled to −20° and treated with a 10% -solution of phosphorus tribromide in dry methylene chloride (0.71 ml, 1.5 equiv.). The mixture was kept at −20° for 20 minutes, when gradual addition of light petroleum (b.p. 40 to 60°) precipitated an oil which solidified on trituration. The solid was filtered off, washed with light petroleum and dried to give the title phosphonium salt (317 mg, 99%). The p.m.r. spectrum (Me$_2$SO-d$_6$) of the product was not as well resolved as that obtained in (i) above, but supported the assigned structure.

EXAMPLE 16

(a) 2,2,2-Trichloroethyl 3-Bromomethyl-7β-formamidoceph-3-em-4-carboxylate

A stirred solution of 2,2,2-trichloroethyl 3-bromomethyl-7β-formamidoceph-3-em-4-carboxylate, 1β-oxide (5.77 g, 12.3 mmole) in a mixture of dry methylene chloride (400 ml) and dry tetrahydrofuran (50 ml) was cooled to −20° and treated with a solution of phosphorus tribromide (1.77 ml, 1.5 equiv.) in dry methylene chloride (9 ml.). the reaction mixture was stirred at −20° for 35 minutes when an excess of saturated aqueous sodium hydrogen carbonate solution was assed. The organic phase was washed with water, dried (MgSO$_4$), and evaporated to give the title ester as a cream foam (5.87 g, 100%), [α]$_D$ − 23.3° (C 1.10; tetrahydrofuran), λ$_{max.}$ (EtOH) 277.5 nm (ε 6,800), ν$_{max.}$ (CHBr$_3$) 3450 (NH), 1790 (azetidin-2-one), 1740 (CO$_2$R) and 1700 and 1503 cm$^{-1}$(CONH), τ (CDCl$_3$) 0.03 (1H,d, J 8 Hz; NH), 1.87 (1H, s; CHO), 4.16 (1H,dd,J 8 and 5 Hz; C$_7$-H), 4.75 (1H,d, J 5Hz; C$_6$-H), 4.80 and 5.00 (2H, AB-q, J 13 Hz; CH$_2$CCl$_3$), 5.47 (2H, centre of an AB-q; C$_3$-CH$_2$Br), 6.14 and 6.39 (2H,AB-q, J 17 Hz; C$_2$-H$_2$).

(b) [7β-Formamido-4-(2,2,2-trichloroethoxycarbonyl)-ceph-3-em-3-ylmethyl]-triphenylphosphonium Bromide A solution of triphenylphosphine (1.06 g, 2 equiv.) in ethyl acetate (5 ml) was added to a stirred solution of 2,2,2-trichloroethyl 3-bromomethyl-7β-formamidoceph-3-em-4-carboxylate (0.91 g, 2 mmole) in ethyl acetate (5 ml). The mixture was stirred at ca. 20° for 45 minutes and then warmed to 45° for 10 minutes. The precipitated solid was filtered off, washed with ethyl acetate and ether, and dried to give the title phosphonium salt (1.06 g, 74%), m.p. 151° to 153° (dec.), [α]$_D$ + 92° (C 1.0; CHCl$_3$), λ$_{max.}$ (EtOH) 268.5 nm (ε 9,000) and 275 nm (ε 9,000), ν$_{max.}$ (CHBr$_3$) 3430 (NH), 1795 (azetidin-2-one), 1730 (CO$_2$R), 1700 (CONH) and 1445 cm$^{-1}$ (P$^+$-C$_6$H$_5$), 0.91 (1H,d, J9 Hz; NH), 4.25 (1H,dd, J 9 and 5 hz; C$_7$-H), 4.67 (1H,d, J 5 Hz; C$_6$-H), 4.77 and 4.93 (2H, centers of two collapsed AB-quarters, J$_{P.H}$ 16 Hz; C$_3$-CH$_2$P$^+$), 5.25 and 5.45 (2H, AB-q, J 12 Hz; CH$_2$CCl$_3$) (Found: C, 46.9; H, 3.7; N, 3.7; P, 3.7; S, 3.9%; total halogen content, 3.9 equiv./mole compound. C$_{29}$H$_{25}$BrCl$_3$N$_2$O$_4$PS (714.9) requires C, 48.7; H, 3.5; N, 3.9; P, 4.3; S, 4.5%; total halogen content 4 equiv./mole compound).

EXAMPLE 17

(a) 2,2,2Trichloroethyl 3-Bromomethyl-7β-phenoxyacetamidoceph-3-em-4-carboxylate.

A stirred solution of 2,2,2-trichloroethyl 3-bromomethyl-7β-phenoxyacetamidoceph-3-em-4-carboxylate 1β-oxide (5.73 g, 9.96 mmole) in dry methylene chloride (100 ml) was cooled to −50° and treated with phosphorus tribromide (1.42 ml, 1.48 equiv.). The reaction mixture was kept at −50° for 1 hour and then allowed to warm to 0° over a period of 30 minutes. An excess of 3% -sodium hydrogen carbonate solution was added, the mixture was stirred for 5 minutes, and the organic phase was washed with water (50 ml), dried (MgSO$_4$) and evaporated to a foam (6.3 g). Chromatography on Kieselgel G (Merck; 200 g (with 25% -ethylacetate in benzene as eluant gave the title ester as a pale-yellow foam (2.77 g, 50%), [α]$_D^{24}$ − 2.7° (C 1.03; Me$_2$SO), λ$_{max}$(EtOH) 269 nm (ε 8,700) and 275.5 nm (ε 9,050), ν$_{max.}$(CHBr$_3$), 3410 (NH), 1780 (azetidin-2-one), 1742 (CO$_2$R) and 1690 and 1512 cm$^{-1}$(CONH), τ (Me$_2$SO-d$_6$) 0.84 (1H,d, J 8 Hz; NH), 2.72 and 3.04 (2H and 3H, 2 m; C$_6$H$_5$O), 4.21 (1H,dd, J 8 and 5 Hz; C$_6$-H), 4.74 (1H,d, J 5 Hz; C$_6$-H), 4.79 and 5.00 (2H, AB-q, J 12 Hz; CH$_2$CCl$_3$), 5.39 (2H, s; C$_6$H$_5$OCH$_2$), 5.41 and 5.56 (2H, AB-q, J 11 Hz; C$_3$-CH$_2$Br), 6.15 and 6.39 (2H, AB-q, J 18 Hz; C$_2$-H$_2$).

(b) [7β-Phenoxyacetamido-4-(2,2,2-trichloroethoxycarbonyl) ceph-3-em-3-ylmethyl]-triphenylphosphonium Bromide A solution of 2,2,2-trichloroethyl 3-bromomethyl-7β-phenoxyacetamidoceph-3-em-4-carboxylate (ca. 7 mmole) in ethyl acetate (25 ml) was stirred at 25° in the absence of light while a solution of triphenylphosphine (3.67g, 2 equiv.) in ethyl acetate (40 ml) was added over 10 mnites. The reaction mixture was stirred at 25° for 3½ hours and the precipitated solid was filtered off washed with ethyl acetate and dried, (5.62 g), and redissolved in chloroform (40 ml). The filtered solution was diluted with a mixture of ether (20 ml) and light petroleum (b.p. 40 to 60°; 10ml) and stirred for 30 minutes, and the precipitated solid was filtered off and dried to give the title phosphonium salt (5.47 g, 95%), m.p. 125° to 135°, [α]$_D^{23}$+4.4° (C 1.06; (Me$_2$SO), λ$_{max.}$(EtOH) 268 nm (ε 9,250) and 275 nm (ε 8,850), ν$_{max.}$ (CHBr$_3$) 3430 (NH), 1794 (azetidin-2-one), 1730 (CO$_2$R), 1693 and 1520 and (CONH) and 1442 cm$^{-1}$ (P$^+$-C$_6$H$_5$).

EXAMPLE 18

(a) Diphenylmethyl 3-Bromomethyl-7β-phenoxyacetamidoceph-3-em-4-carboxylate, 1β-Oxide Peracetic acid (37.6%; 2.4 ml. 11.63 mmole) was added over a period of 20 minutes to a stirred solution of diphenyl methyl 3methyl-7β-phenoxyacetamidoceph-3-em-4-carboxylate (6.0 g, 11.65 mmole) in 1,2-dichloroethane (200 ml.). The mixture was stirred for a further 30 minutes, washed with water and 3%-sodium hydrogen carbonate solution (50 ml of each) dried, and concentrated to ca. 100 ml. The solution was made up to 300 ml with 1,2-dichloroethane and part (250 ml) was stirred and cooled to −9°, and 1,3-dibromo-5,5-dimethylhydantoin (2.08 g, 7.28 mmole) was added. The stirred, cooled mixture was irradiated with a 125-watt medium-pressure mercury-arc, with a Pyrex-filter, for 1 hour at −9° in an atmosphere of nitrogen. The reaction mixture was filtered and washed with 3% -sodium hydrogen carbonate solution (2 × 100 ml) and water (50 ml.). The aqueous washings were back-washed with 1,2-dichloroethane (50 ml) and the combined organic phases were dried (MgSO$_4$) and concentrated to low volume, whereupon a solid separated. This solid was filtered off, washed with ether, and dried to give the title ester 1β-oxide (2.87 g, 48.5%), m.p. 157° to 160°, $[\alpha]_D^{25} - \sqcup°$ (c 0.94;Me$_2$SO), $\lambda_{max.}$(EtOH) 268.5 ($\epsilon$ 9,250) and 274.5 nm ($\epsilon$ 9,950), part of which was recrystallised from methanol to give a white solid, m.p. 165° to 167° (dec.), $[\alpha]_D^{25} - 51°$ (C 0.80; Me$_2$SO), $\lambda_{max.}$ (EtOH) 269.5 nm ($\epsilon$ 9,700) and 275.5 nm ($\epsilon$ 10,500), $\nu_{max.}$ (CHBr$_3$) 3390 (NH), 1800 (azetidin-2-one), 1725 (CO$_2$R), 1690 and 1515 (CONH), and 1050 cm$^{-1}$ (S→O), $\tau$ (Me$_2$SO-d$_6$) 0.81 (1H,d, J 10 Hz; NH), 2.3 to 2.8 and 2.98 (12H and 4H; 2 m; (C$_6$H$_5$)$_2$CH and C$_6$H$_5$O), 3.84 (1H,dd,J 10 and 5 Hz; C$_7$-H), 4.91 (1H,d,J 5 Hz; C$_6$-H), 5.30 (2H, s; C$_6$H$_5$OCH$_2$), 5.43 and 5.58 (2H,AB-q, J 10 Hz; C$_3$-CH$_2$Br), 5.94 and 6.19 (2H, AB-q, J 19 Hz; C$_2$-H$_2$) (Found : C, 56.9, 56.5; H, 4.3, 4.2; Br, 11.85, 12.2; N, 4.1, 4.4; S, 5.3. C$_{29}$H$_{25}$BrN$_2$O$_6$S (609.5) requires C, 57.15; H, 4.1; Br, 13.1; N, 4.6; S, 5.3%).

(b) Diphenylmethyl 3-Bromomethyl-7β-phenoxyacetamidoceph-3-em-4-carboxylate

A solution of diphenylmethyl 3-bromomethyl-7β-phenoxyacetamidoceph-3-em-4-carboxylate, 1β-oxide (1.83 g, 3 mmole) in dry methylene chloride (25 ml) was cooled to $-25°$, and phosphorus tribromide (0.43 ml, 1.5 equiv.) was added over 5 minutes, the temperature of the mixture being kept below $-20°$ during the addition. The reaction mixture was stirred at $-20°$ for 2 hours, diluted with methylene chloride (75 ml), washed with 3%-sodium hydrogen carbonate solution (2 × 50 ml), and water (50 ml), dried, and evaporated to give the title ester as a pale-orange foam (1.515 g,85%), $\lambda_{max.}$ (EtOH) 268.5 nm ($\epsilon$ 6,950), $\tau$ (CDCl$_3$) 2.4 to 2.8 and 2.98 (12H and 5H, 2m; (C$_6$H$_5$)$_2$CH, C$_6$H$_5$O and NH), 4.08 (1H, dd, J 9 and 5 Hz; C$_7$-H), 4.98 (1H,d, J 5 Hz; C$_6$-H), 5.45 (2H, S; C$_6$H$_5$OCH$_2$), 5.71 (2H, s; C$_3$-CH$_2$Br), 6.32 and 6.56 (2H, AB-q, J 18 Hz; C$_2$-H$_2$).

(c) [4-Diphenylmethoxycabonyl-7β-phenoxyacetamidoceph-3-em-3-ylmethyl]-triphenylphosphonium Bromide A solution of triphenylphosphine (0.99 g, 1.5 equiv.) in ethyl acetate (10 ml) was added to a stirred solution of diphenylmethyl 3-bromomethyl-7β-phenoxyacetamidoceph-3-em-4-carboxylate (ca. 1.49 g, 2.515 mmole) in ethyl acetate (25 ml). The mixture was stirred in the absence of light for 16 hours, and the precipitated solid was filtered off, washed with ethyl acetate and dried to give the title phosphonium salt (1.585 g, 74%), $\lambda_{max.}$ (EtoH) 268.5 nm ($\epsilon$ 10,700) and 275.5 nm($\epsilon$ 9,850), $\nu_{max.}$(CHBr$_3$), 3415 (NH), 1788 (azetidin-2-one), 1710 (CO$_2$R), 1692 and 1620 (CONH) and 1440 cm$^{-1}$ (P$^+$-C$_6$H$_5$).

EXAMPLE 19

(a) 7β-Formamido-3-methylceph-3-em-4-carboxylic Acid

7β-Amino-3-methylceph-3-em-4-carboxylic acid (20 g, 93.3 mmole) was added to a mixture of acetic anhydride (30 ml) and formic acid (98 to 100%; 160 ml), previously cooled to 0°. After 30 minutes, when solution had been obtained, the solvents were removed in vacuo and ethyl acetate (200 ml) was added to the residual oil. Some insoluble gelatinous material was removed by filtration and the filtrate was evaporated to give the title acid as a pale yellow foam, $\lambda_{max.}$ (pH 6 phosphate) 260.5 nm (E$_{1cm}^{1\%}$ 287).

(b) Diphenylmethyl 7β-Formamido-3-methylceph-3-em-4-carboxylate

A solution of diphenyldiazomethane in ether (prepared from benzophenone hydrazone [21 g, 41.8 mmole]) was added to a solution of 7β-formamido-3-methylceph-3-em-4-carboxylic acid (9.7 g, 40.2 mmole) in tetrahydrofuran (150 ml) and the mixture was stirred overnight in the absence of light. The solvents were removed in vacuo and the residual oil was dissolved in methylene chloride (200 ml). The solution was washed with 3%-sodium hydrogen carbonate solution (2 × 100 ml), dried, and evaporated to a yellow oil which was triturated with ethyl acetate-ether to give the title ester as a white crystalline solid (8.15 g, 49.5%), m.p. 136 to 140°, $[\alpha]_D^{23} + 38°$ (c 0.94; Me$_2$SO), $\lambda_{max.}$(EtOH) 258 nm ($\epsilon$ 6,800), $\nu_{max.}$(Nujol) 3330 (NH), 1771 (azetidin-2-one), 1707 (CO$_2$R) and 1655 and 1523 cm$^{-1}$(CONH), $\tau$ (Me$_2$SO-d$_6$) 1.91 (1H, d, J 9.5 Hz; NH), 1.89 (1H, s; CHO), 2.4 to 2.8 (10H, m; (C$_6$H$_5$)$_2$CH), 3.07 (1H, s; (C$_6$H$_5$)$_2$CH), 3.19 (1H,dd, J 9.5 and 5 Hz; C$_7$-H), 4.83 (1H,d, 5 Hz; C$_6$-H), 6.33 and 6.57 (2H, AB-q, 18 Hz; C$_2$-H$_2$), 7.95 (3H, S; C$_3$-CH$_2$) (Found: C, 64.55; H, 4.9; N, 6.7; S, 7.7. C$_{22}$H$_{20}$N$_2$O$_4$S (408.5) requires C, 64.7; H, 4.9; N, 6.9; S, 7.85%).

(c) Diphenylmethyl 3-Bromomethyl-7β-Formamidoceph-3-em-4-carboxylate 1β-Oxide

A solution of diphenylmethyl 7β-formamido-3-methylceph-3-em-4-carboxylate (6 g, 14.7 mmole) in 1,2-dichloroethane (200 ml) was cooled in an ice-bath and treated with peracetic acid (1 equiv.). The reaction mixture was washed with water (100 ml), 3%-sodium hydrogen carbonate solution (50 ml), dried, and diluted to 400 ml with 1,2-dichloroethane. Part (350 ml) was cooled to 0° and stirred, and a solution of sodium acetate (4.84 g, 59 mmole) in water (25 ml), adjusted to pH 7 by the addition of acetic acid, and 1,3-dibromo-5,5-dimethylhydantoin (2.76 g, 9.65 mmole) were added. The stirred, cooled mixture was irradiated with a 125-watt medium pressure mercury-arc with a Pyrex-filter for 40 minutes at 0° to +3° in an atmosphere of nitrogen. The reaction mixture was washed with 2.5% aqueous sodium metabisulphite solution (200 ml) and water (1 × 150 and 1 × 100 ml). The aqueous washings were backwashed with 1,2-dichloroethane (100 ml) and the combined organic phases were dried (MgSO$_4$) and evaporated. Trituration of the residue with a mixture of ethyl acetate and ether gave the title ester 1β-oxide as a beige solid (3.52 g, 54%), m.p. 155.5 to 157° (dec.), $[\alpha]_D^{23} - 18.5°$ (c 0.96; Me$_2$SO), $\lambda_{max.}$ (EtOH) 279.5 nm ($\epsilon$ 10,100). Part (0.44 g) of the product was crystallised from acetone (25 ml) and ether (10 ml) to give material (0.21 g), m.p. 169.5° to 170° (dec.), $[\alpha]_D^{23} - 14.4°$ (c 0.95; Me$_2$SO), $\lambda_{max.}$ (EtOH) 278.5 nm, $\nu_{max.}$ (Nujol) 3280 (NH), 1772 (azetidin-2-one), 1710 (CO$_2$R), 1664 and 1510 cm$^{-1}$(CONH), and 1020 cm$^{-1}$(S→O), $\tau$ (Me$_2$SO-d$_6$) 0.74 (1H,d, J 10 Hz; NH), 0.79 (1H, s; CHO), 2.3 to 2.7 (10 H, m; (C$_6$H$_5$)$_2$CH), 2.98 (1H, s; (C$_6$H$_5$)$_2$CH), 3.91 (1H,dd, J 10 and 4.5 Hz; C$_7$-H), 4.91 (1H,d, J 4.5 Hz; C$_6$-H), 5.35 and 5.58 (2H, AB-q, J 10 Hz; C$_3$-CH$_2$Br), 5.95 and 6.20 (2H, AB-q, J 19 Hz; C$_2$-H$_2$) (Found: C, 51.4; 50.8; H, 3.95, 3.8; Br, 15.9; N, 5.2, 5.1; S, 6.4. C$_{22}$H$_{21}$BrN$_2$O$_5$S (503.4) requires C, 52.5; H, 3.8; Br, 15.9; N, 5.6; S, 6.4%).

(d) Diphenylmethyl 3-Bromomethyl-7β-formamidoceph-3-em-4-carboxylate

A stirred suspension of diphenylmethyl 3-bromomethyl-7β-formamidoceph-3-em-4-carboxylate, 1β-oxide (2.01 g, 4 mmole) in dry methylene chloride (30 ml) was cooled to −20° and a solution of phosphorus tribromide (0.57 ml, 1.5 equiv.) in dry methylene chloride (10 ml) was added over a period of 10 minutes, the temperature of the mixture being kept at −20°. The mixture was stirred at −20° for 45 minutes, and the organic phase was washed with 4%-sodium hydrogen carbonate solution (2 × 50 ml) and water (50 ml), dried (MgSO$_4$), and evaporated to give the title ester as a pale orange foam (1.84 g, 94.5%), $\lambda_{max.}$ (EtOH) 269 nm (ε 7200), τ (CDCl$_3$) 1.78 (1H, s; CHO), 2.4 to 2.8 (10H, m; (C$_6$H$_5$)$_2$CH), 3.00 (1H, s;(C$_6$H$_5$)$_2$CH), 3.43 (1H, d, J 9 Hz; NH), 4.10 (1H, dd, J 9 and 5 Hz; C$_7$-H), 4.99 (1H,d, J 5 Hz; C$_6$-H), 5.70 (2H,s; C$_3$-CH$_2$Br), 6.25 and 6.62 (2H, AB-q, J 18 Hz; C$_2$-H$_2$).

(e) [4-Diphenylmethoxycarbonyl-7β-formamidoceph-3-em-3-ylmethyl]-triphenylphosphonium Bromide A solution of triphenylphosphine (1.47 g, 1.5 equiv.) in ethyl acetate (10 ml) was added to a stirred solution of diphenylmethyl 3-bromomethyl-7β-formamidoceph-3-em-4-carboxylate (1.82 g, 3.725 mmole) in ethyl acetate (50 ml). The mixture was stirred overnight at ca. 20° out of direct light, and the precipitated solid was filtered off, washed with ethyl acetate and dried to give the title phosphonium salt (2.41 g, 86%), $\lambda_{max.}$ (EtOH) 268.5 nm (ε 8,700) and 275.5 nm (ε 8,150), $\nu_{max.}$ (CHBr$_3$) 3440 (NH),(1788 azetidin-2-one), 1710 (CO$_2$R), 1680 and 1500 (CONH) and 1443 cm$^{-1}$(P$^+$-C$_6$H$_5$), τ (CDCl$_3$) 1.45 (1H,d, J 9 Hz; NH), 1.73 (1H,s; CHO), 3.57 (1H, s; (C$_6$H$_5$)$_2$CH), 4.32 (1H,dd, J 9 and 5 Hz; C$_7$-H), 4.62 and 4.78 (2H, centres of 2 AB-quartets, $J_{P-H}$ 16 Hz, $J_{H-H}$ 15 Hz; C$_3$-CH$_2$P$^+$), 5.12 (1H,d, J 5 Hz; C$_6$-H), 6.06 and 6.60 (2H, broadened AB-q, J 18 Hz; C$_2$-H$_2$).

EXAMPLE 20

(a) Diphenylmethyl 3-(Dimethoxyphosphinylmethyl)-7β-(2-thienylacetamido)ceph-3-em-4-carboxylate A solution of diphenylmethyl 3-iodomethyl-7β-(2-thienylacetamido)-ceph-3-em-4-carboxylate (1.26 g.) in ethyl acetate (15 ml.) was treated with trimethylphosphite (1.0 ml.), and the mixture was refluxed for 1.25 hours. The solution was run into petroleum ether (b.p. 40° to 60°) to give the phosphonate (1.2 g., 98%) as an amorphous solid, m.p. ca. 65°, [α]$_D$− 3.3° (CHCl$_3$), inflexions at 235 and 260 nm. (ε 13,050 and 7,040), $\lambda_{max.}$(CHBr$_3$) 3380 (NH), 1780 (β-lactam), 1720 (CO$_2$R), 1680 and 1510 (CONH), 1250 (P=O), and 1030 cm$^{-1}$ (P-O-C), τ (DMSO-d$_6$) 0.86 (NH, d, J 9 Hz.), 4.20 (C$_{(7)}$-H, dd, J 4.5 and 9 Hz.), 4.81 (C$_{(6)}$-H, d, J 4.5 Hz.), 6.19 (CH$_2$CONH) 6.32 and 6.35 (C$_{(2)}$-CH$_2$, parts of an AB-q J not measurable, and 6.57 and 6.52 (POCH$_3$) (Found: C, 56.7; H, 4.9; N, 4.3; P 5.2; S, 10.7. C$_{29}$H$_{29}$N$_2$O$_7$PS$_2$ requires C, 56.9; H, 4.8; N, 4.6; P, 5.05; S, 10.5%).

(b) 3-(Dimethoxyphosphinylmethyl)-7β-(2-thienyl acetamido)ceph-3-em-4-carboxylic Acid A solution of diphenylmethyl 3-(dimethoxyphosphinylmethyl)-7β-(2-thienylacetamido) ceph-3-4-carboxylate (750 mg.) in anisole (0.75 ml.) and trifluoroacetic acid (3.0 ml.) was stored at 21° for 5 minutes. The solvents were removed in vacuo and the residue triturated with ether to give the acid (490 mg., 89%) as an amorphous solid, m.p. 150° to 154° (decomp.), [α]$_D$+ 131° (MeOH), $\lambda_{max.}$ (0.1M pH6 phosphate buffer) 261.5 nm (ε 8,350), $\nu_{max.}$ 3200 (NH), 1780 (β-lactam), 1705 (CO$_2$H), 1645 (CONH) and 1240 cm$^{-1}$ (P=O), τ (DMSO-d$_6$) 0.95 (NH, d, J 9 Hz.), 2.68 and 3.08 (thienyl), 4.40 (C$_{(7)}$-H, dd, J 4.5 and 9 Hz.), 4.91 (C$_{(6)}$-H, d, J 4.5 Hz), 6.25 (CH$_2$CONH), 6.32 and 6.40 (POCH$_3$) and 6.3 to 7.0 (C$_{(2)}$-CH$_2$ and CH$_2$P, complex) (Found: C, 43.9; H, 4.4; N, 6.4; P, 6.55; S, 13.5. C$_{16}$H$_{19}$N$_2$O$_7$PS$_2$ requires C, 43.0; H, 4.3; N, 6.3; P, 6.95; S, 14.3%). R$_f$ 0.08 (system C).

EXAMPLE 21

(a) t-Butyl 7β-(D-2-t-Butoxycarbonylamino-2-phenylacetamido)-3-chloromethylceph-3-em-4-carboxylate A solution of t-butyl 7β-(D-2-t-butoxycarbonylamino-2-phenylacetamido)-3-hydroxymethylceph-3-em-4-carboxylate (17.5 g, 0.034 moles) in pure tetrahydrofuran (135 ml.) with pyridine (10.9 ml., 0.135 moles) was added, over a 40 minute period, to a vigorously-stirred solution of thionyl chloride (4.85 ml., 0.068 moles) in pure tetrahydrofuran (100 ml.) at −25°. After a total of 55 minutes stirring the mixture was poured into N-hydrochloric acid containing sodium chloride. The aqueous phase was extracted with ethyl acetate (2 × 300 ml.), and the extracts were combined and washed with water, aqueous sodium bicarbonate solution, and further amounts of water, and then dried, and evaporated in vacuo. A solution of the residue in ethyl acetate was run into petroleum ether (b.p. 40° to 60°) to give the crude chloromethyl derivative (12 g.). Evaporation of the petroleum solution gave a purer sample (2.57 g.). The crude sample was extracted with ether and the ether solution was filtered and run into petroleum ether to give a second purer sample. The purest samples were combined to give the chloromethyl derivative (14.07 g., 77.5%) as an amorphous solid, m.p. 106° to 110° (decomp.), [α] - 24.2° (CHCl$_3$), $\lambda_{max.}$ 265 nm. (ε 6,800), $\nu_{max}$ (CHBr$_3$) 3410 (NH), 1780 (β-lactam), 1716 (CO$_2$R), 1706 and 1510 (NHCO$_2$R) and 1590 and 1495 cm.$^{-1}$ (CONH), τ (CDCl$_3$) 2.63 (Ph), 3.07 (CONH, d, J 9 Hz), 4.19 (C$_{(7)}$-H, dd, J 4.5 and 9 Hz.), 4.29 (NHCH, d, J 7 Hz.), 4.78 (NHCH, d, J 7 Hz.), 5.11 (C$_{(6)}$-H, d, J 4.5 Hz.), 5.59 (CH$_2$C 1, s), 6.42 and 6.69 (C$_{(2)}$-CH$_2$, AB-q, $J_{AB}$ 18 Hz.), and 8.44 and 8.59 (t Butyls) (Found: C, 56.2; H, 6.2; N, 7.7. C$_{25}$H$_{32}$CIN$_3$O$_6$S requires C, 55.8; H, 6.0; N, 7.8%).

(b) [7β-(D-2-t-Butoxycarbonylamino-2-phenylacetamido)-4-t-butoxycarbonylceph-3-em-3-ylmethyl]triphenylphosphonium iodide A solution of t-butyl 7β-(D-2-t-butoxycarbonylamino-2-phenylacetamido)-3-chloromethylceph-3-em-4-carboxylate (2.5 g.) in acetone (20 ml.) was treated with a solution of sodium iodide (2.43 g., ca. 4 equiv.) in acetone (20 ml.). The mixture was stored in the dark for 2 hours, then poured into brine and the insoluble material extracted into ethyl acetate. The organic phase was washed with water and dilute aqueous sodium thiosulphite solution, and with further amounts of water, and dried and evaporated in vacuo. The residue, in ethyl acetate, was run into petroleum ether (b.p. 40° to 60°) to give the crude iodomethyl compound (2.48 g.) as an amorphous solid, m.p. 114° to 125° (decomp.). [α] - 75.9° (CHCl₃), λ_max. 285 nm. (ε 7,550).

A solution of the iodomethyl derivative (1.55 g.) in ethyl acetate (10 ml.) was treated with a solution of triphenylphosphine (1.3 g.) in ethyl acetate (9 ml.) and the mixture stored in the dark for 1½ hours. The solution was run into petroleum ether (b.p. 40° to 60°)to give the phosphonium salt (1.8 g.) as an amorphous solid, m.p. 172° to 188° (decomp.), [α] - 2.4° (CHCl₃), λ_max. 269 nm. (ε 10,250) and 275.5 nm, (ε 9,900), ν_max. (CHBr₃) 3420 (NH), 1780 (β-lactam), 1700 and 1500 (CONH and NHCO₂R), and 1440 cm.⁻¹ (P-C aryl), τ (DMSO-d₆; spectrum not well resolved) 0.81 (NH, d, J ca. 9 Hz.), 2.13 (P-Ph), 2.61 (PhCH), 4.3 to 5.2 (NHCH,C₍₇₎-H, C₍₆₎-H, CH₂P, complex), and 8.6 and 8.79 (t.Butyl).

SECTION A (ii)

EXAMPLE 1

Diphenylmethyl 7β-(2-thienylacetamido)-3-(triphenylphosphoranylidene-methyl) ceph-3-em-4-carboxylate A solution of [4-diphenylmethoxycarbonyl-7β-(2-thienylacetamido) ceph-3-em-3-ylmethyl] triphenylphosphonium iodide (25 g.) in acetone (300 ml.) with water (40 ml.) was cooled to 0° and taken to pH 11 with 2N-sodium hydroxide. The mixture, containing a precipitated yellow solid, was diluted with acetone (200 ml.) and water (50 ml.), and filtered. The collected solid was washed with acetone and ether, and dried in vacuo to give diphenylmethyl 7β-(2-thienylactamido)-3-(triphenylphosphoranylidenemethyl) ceph-3-em-4-carboxylate (17 g., 78.5%) as a yellow crystalline solid, m.p. 133°-138° (Decomp), [α]_D − 35° (CHCl₃), λ_max (CHCl₃) 388 nm. (ε 18,500), 278 nm (ε 6,240) and 267 nm (ε 6,940), ν_max (CHBr₃) 3360 (NH), 1746 (β-lactam), 1670 (CO₂R), 1642 and 1500 (CONH), and 1438 (P-C aryl) cm⁻¹; τ (CDCl₃) 4.82 (C₍₇₎-H, dd, J 4.5, 9Hz), 4.95 (C₍₆₎-H, d, J 4.5 Hz), 7.11 and 7.55 (C₍₂₎-CH₂, two dd. J_H-H 14 Hz., J_P-H 1-2 Hz) and 4.5 (CH= P$\left<\right.$, d, J_P-H 22 Hz). [Found: C, 66.6; H, 4.7; N, 2.9; P, 3.9; S, 7.8. C₄₅H₃₇N₂O₄S₂P (764.8) requires C, 70.6; H, 4.8; N, 3.6; P, 4.0; S, 8.4%].

EXAMPLE 2

Diphenylmethyl 7β-(2-thienylacetamido)-3-(triphenylphosphoranylidene methyl) ceph-3-em-4-carboxylate A solution of [4-diphenylmethoxycarbonyl-7β-(2-thienylacetamido) ceph-3-em-3-ylmethyl] triphenylphosphonium bromide (26.4 mg.) in chloroform (5 ml.) was treated with ethoxycarbonylmethylenediphenylphosphorane (11 mg., ca 1 equiv.) in chloroform (5 ml.) and the solvent immediately removed in vacuo. The residue was treated with 10% aqueous acetone (5 ml.). The insoluble yellow crystalline material isolated by filtration and dried in vacuo to give the title compound (17 mg.), λ_max (CHCl₃) 388 nm (ε 19,200).

EXAMPLE 3

Diphenylmethyl 7β-(2-Thienylacetamido)-3-(triphenylphosphoranylidenemethyl) ceph-3-em-4-carboxylate.

A solution of (4-diphenylmethoxycarbonyl-7β-(2-thienylacetamido)ceph-2-em-3-ylmethyl) triphenylphosphonium chloride (200 mg.) in acetone (6 ml.) was treated with saturated aqueous sodium bicarbonate solution (1 ml.) and water (1 ml.) and a few drops of 2N-aqueous sodium hydroxide. A yellow solid came out of solution. The mixture was diluted with water and filtered and the collected solid was washed with water and acetone and ether to give (after drying in vacuo) the ylid (135 mg., 70.5%) as a yellow crystalline solid, m.p. 198° to 199° (decomp.), [α] −67° (CHCl₃) (falling to −31° (CHCl₃) after 30 minutes at 23°), λ_max. (CHCl₃) 388 nm. (ε 20,100) and 266.5 nm. (ε7,650). The ultraviolet, infrared and p.m.r. spectra were identical with those of sample described in Example A (ii) 1; there was no evidence for the presence of any Δ²-isomers.

SECTION A (iii)

EXAMPLE 1

(a) Diphenylmethyl 7β-(2-thienylacetamido)-3-vinyl ceph-3-em-4-carboxylate.

A solution of diphenylmethyl 7β-(2-thienylacetamido)-3-(triphenylphosphoranylidenemethyl) ceph-3-em-4-carboxylate (2.55 g.) Rf 0.0, in methylene dichloride (150 ml.) was treated, at 10°, with 40% formaldehyde solution (20 ml.). The mixture was stirred vigorously at 10° until the orange colour characteristic of the starting material had disappeared (ca 30 minutes). The methylene chloride solution was dried and evaporated in vacuo. The residue was triturated with ethyl acetate and the insoluble crystalline material collected by filtration. The filtrate, on treatment with ether, gave a further crop of crystalline material. The combined solids (1.25 g., 72.5%) were crystallized from methanol to give pure diphenylmethyl 7β-(3-thienylacetamido)-3-vinylceph-3-em-4-carboxylate (780 mg.), Rf 0.5, as small needles, m.p. 176° to 177° (dec) [α]_D − 132.8°(CHCl₃), λ_max 296 nm (ε 13,620) ν_max (CHBr₃) 3420 (NH), 1788 (β-lactam), 1720 (CO₂R), and 1680 and 1510 (CONH) cm⁻¹; τ (CDCl₃) 4.21 (C₍₇₎-H, dd, J 4.5 and 9 Hz, 5.06 (C₍₆₎-H, d, J 4.5 Hz), 6.36 and 6.58 (C₍₂₎-CH₂, AB-q, J_AB 18 Hz), and 3.2 (dd), 4.65 (d) and 4.8 (d) (—CH = CH₂). ABX system, J_AX 16 Hz., J_BX 12 Hz., J_AB 0 Hz). [Found: C, 64.9; H, 4.8; N, 5.3; S, 12.4. C₂₈H₂₄N₂O₄S₂ (516.5) requires C, 65.1; H, 4.7; N, 5.4; S, 12.4%].

(b)

7β-(2-Thienylacetamido)-3-vinylceph-3-em-4-carboxylic acid

A solution of diphenylmethyl 7β-(2-thienylacetamido)-3-vinylceph-3-em-4-carboxylate (700 mg.) in trifluoroacetic acid (2.8 ml.) with anisole (0.7 ml.) was kept at room temperature for 4 minutes. The solvent was removed in vacuo, and the residue partitioned between ethyl acetate and 2N-sodium bicarbonate solution. The bicarbonate solution on acidification (to pH 2) with 2N-hydrochloric acid gave the acid (430 mg. 90%). Precipitation of this material from ethyl acetate solution by petroleum-ether gave pure 7β-(2-thienylacetamido)-3-vinylceph-3-em-4-carboxylic acid (350 mg.) as an amorphous solid, [α]_D − 37.7°(tetrahydrofuran) λ_max (0.1M phosphate buffer; pH 6) 288 nm. (ε 15,440), ν_max (CHBr₃) 3390 (NH), 1775 (β-lactam), 1730 (CO₂H) and 1690 and 1572 cm⁻¹; (CONH and CO₂H), τ (D₂O with sodium bicarbonate) 4.45 (C₍₇₎-H, d, J 4.5 Hz), 4.95 (C₍₆₎-H, d, J 4.5 Hz), 6.36 and 6.58 (C₍₂₎-CH₂, AB-q J_AB 18 Hz). and 3.28 (dd), 4.65 (d), and 4.8 (d) (CH=CH₂, ABX-system, J_AX 16 Hz., J_BX 12 Hz., J_AB 0

Hz), Rf 0.48 (System C) and $R_F$ 0.41 (System B but using Whatman No. 1 paper). [Found: C, 51.4; H, 3.9; N, 7.5; S, 17.5. $C_{15}H_{14}N_2O_4S_2$ (350.4) requires C, 51.4; H, 4.0; N, 8.0; S, 18.3%].

EXAMPLE 2

(a) (i) Diphenylmethyl 3-(prop-1-enyl)-7β-(2-thienylacetamido)ceph-3-em-4-carboxylate Diphenylmethyl 7β-(2-thienylacetamido)-3-(triphenylphosphoranylidenemethyl)ceph-3-em-4-carboxylate (1.528 g., 2 m mole.), Rf 0.0, prepared as in Example A(ii)1 was dissolved in dry methylene chloride (50 ml.), and acetaldehyde (50 ml., 885 m mole.) was added. The solution was stirred at 25° for 3 hours, the solvent and residual acetaldehyde removed by rotatary evaporation, and the residue dissolved in methylene chloride (50 ml.). The resulting solution was washed successively with N-hydrochloric acid (2 × 50 ml.), 2N-aqueous sodium bicarbonate (2 × 50 ml.), water (2 × 50 ml.), brine (50 ml.), dried and evaporated to a pale yellow oil. This material was purified by chromatography on Kieselgel (0.05 - 0.2mm). Combination of similar fractions (as judged by tlc) gave the title compound as a pale yellow solid (100 mg, 10%) Rf 0.58, m.p. 124°-127° (decomp.), $[\alpha]_D$ −20° (THF), $\lambda_{max}$ 287 nm ($\epsilon$ 7,600), $\lambda_{inf}$ 237 nm ($\epsilon$ 13,400), $\nu_{max}$ (CHBr$_3$) 3360 (—NH), 1780 (β-lactam), 1715 and 1230 (ester). 1685 and 1520 (—CONH—) cm$^{-1}$; the p.m.r. spectrum indicated that the compound was mainly the cis-isomer (with 5–10% trans), with signals at τ 3.96 (—CH=CHCH$_3$, d, J 12 Hz), 4.24 (C$_{(7)}$H, dd, J 5 and 9 Hz), 4.51 (=CH(CH$_3$), dd, J 12 and 7 Hz), 5.02 (C$_{(6)}$-H, d, J 5 Hz), 6.6 and 6.8 (C$_{(2)}$-CH$_2$, AB-q, J$_{AB}$18 Hz) and 8.61 (CH = CHCH$_3$, methyl dd, J 7 and ca 0.5 Hz).

(a) (ii) Diphenylmethyl 3-(prop-1-enyl)-7β-(2-thienylacetamido)ceph-3-em-4-carboxylate A mixture of [4-diphenylmethoxycarbonyl-7β-(2-thienylacetamido)ceph-3-em-3-ylmethyl] triphenylphosphonium iodide (890 mg), Rf 0.0 acetaldehyde (8 ml.), and ethylene oxide (2 ml) were kept in a sealed tube at 53° for 22 hours. The solvents were removed and the residue, in the ethyl acetate solution, filtered through a column of 0.05 - 0.2 mm Kieselgel (180 g.). The material obtained on evaporation of the ethyl acetate was further purified by preparative tlc on Kieselgel PF$_{254 + 366}$ to give diphenylmethyl 3-(prop-1-enyl)-7β-(2-thienylacetamido) ceph-3-em-4-carboxylate (150 mg), Rf 0.58, as needles, m.p. 114°-122° (decomp.), $\lambda_{max}$ 293 nm ($\epsilon$ 11,330), $\nu_{max}$ 3400 (NH), 1780 (β-lactam), 1720 (—CO$_2$R), and 1680 and 1520 (—CONH—) cm$^{-1}$; the p.m.r. spectrum (CDCl$_3$) indicated that the compound was a mixture of cis- and trans-isomers and had signals at τ 6.57 (C$_{(2)}$-CH$_2$, singlet) and 8.27 (-CH=CH-CH$_3$, methyl dd, J 7 and ca 1 Hz) for the trans-isomer and at τ 6.57 and 6.85 (C$_{(2)}$-CH$_2$, AB-q J$_{AB}$ 18 Hz) and 8.61 (CH=CH-CH$_3$, methyl dd, J 7 and ca 0.5 Hz) for the cis-isomer.

(b) 7β-(2-Thienylacetamido)-3-(prop-1-enyl)ceph-3-em-4-carboxylic acid, cis and trans-isomers.

A solution of diphenylmethyl 7β-(2-thienylacetamido)-3-(prop-1-enyl)ceph-3-em-4-carboxylate (165 mg., 0.311 mmole) in trifluoroacetic acid (1.0 ml.) and anisole (0.5 ml.) was stirred for 5 minutes at room temperature. The solvents were removed in vacuo, and the residue partitioned between ethyl acetate and the 2N-sodium bicarbonate solution. Acidification (to pH 2) of the bicarbonate solution gave the acid (85 mg 75%). Precipitation of this material from ethyl acetate solution by petroleum-ether gave pure 7β-(2-thienylacetamido)-3-(prop-1-enyl)ceph-3-em-4-carboxylic acid (52 mg.) as a white solid, $[\alpha]_D$ + 40° (dioxan), $\lambda\lambda_{max}$, (0.1M-phosphate buffer; pH 6) 285 nm. ($\epsilon$ 10,100), 236 nm. ($\epsilon$ 11,900), $\nu_{max}$ (CHBr$_3$) 3380 (—NH), 1775 (β-lactam), 1690 to 1680 (CO$_2$H), 1680 and 1520 cm.$^{-1}$ (CONH); the p.m.r. spectrum (D$_2$) with sodium bicarbonate) indicated that the compound was mainly the cis-isomer (with 20–30% trans) with signals at τ 4.07 (-CH=CH.CH$_3$, d, J 12 Hz.), 4.29 (=CH.CH$_3$, dd, J 12 and 6 Hz.), 4.43 (C$_{(7)}$H, d, J 5 Hz.), 4.90 (C$_{(6)}$H, d, J 5 Hz.), 6.49 and 6.75 (C$_{(2)-CH2}$, AB-q,J$_{AB}$ 18 Hz.) and 8.39 (=CH.CH$_3$, methyl d, J 6 Hz.) for the cis-isomer and at τ 6.47 (C$_{(2)}$—CH$_2$, s) and 8.20 (=CH.CH$_3$, methyl d, J 6.5 Hz.) for the trans-isomer, R$_F$ 0.40 (System C) and R$_F$ 0.54 (System B, but using Whatman No. I. paper).

EXAMPLE 3

Diphenylmethyl 7β-(2-thienylacetamido)-3-(pent-1-enyl) ceph-3-em-4-carboxylate, cis-isomer.

A solution of diphenylmethyl 7β-(2-thienylacetamido)-3-triphenylphosphoranylidenemethyl)ceph-3-em-4-carboxylate (1.528 g., 2 mmole) in freshly distilled n-butyraldehyde (50 ml.) was heated to reflux for 18 hours. The excess n-butyraldehyde was distilled off, the residue extracted with ethyl acetate (2 × 50 ml.), and the combined extract washed with 2N-hydrochloric acid (100 ml.), 2N-sodium bicarbonate (100 ml.), water (2 × 100 ml.), brine (100 ml.), dried and evaporated to a pale-yellow oil (2.48 g.). Precipitation of this material from ethyl acetate solution by petroleum-ether gave an oily solid, which was further purified by chromatography on Kieselgel (0.05 - 0.2mm). Combination of fractions, R$_F$ 0.6 (t.l.c.) gave a white solid (30 mg., 4%), $[\alpha]_D$ + 158° (tetrahydrofuran), $\nu_{max}$ (CHBr$_3$) 3380 (—NH), 1770 (β-lactam), 1730 (—CO$_2$R), 1715 (shoulder, —CO$_2$R) and 1680 and 1520 cm$^{-1}$ (—CONH—), $\lambda_{max}$. 272 nm. ($\epsilon$7,900), inflexion at 237 nm. ($\epsilon$ 14,000); the p.m.r. spectrum (CDCl$_3$) indicated that the material was mainly diphenylmethyl 7β-(2-thienylacetamido)-3-(pent-1-enyl)ceph-3-em-4-carboxylate, cis-isomer, with signals at τ 3.60 (-CH = CHCH$_2$CH$_2$CH$_3$, d, J 12 Hz.), 3.98 (C$_{(2)}$-H, s), 4.46 (C$_{(7)}$-H, dd, J 4.5 and 9 Hz.), 4.51 (—CH=CH.CH$_2$CH$_2$CH$_3$, unresolved m), 4.79 (C$_{(6)}$-H, J 4.5 Hz.), 5.11 (C$_{(4)}$-H, d, J ca. 2 Hz.) and 8.34 (m), 8.76 (m) and 9.16 (m), (-CH$_2$CH$_2$CH$_3$) mixed with ca. 20% of the title compound with signals at τ 4.23 (C$_{(7)}$-H, dd, J 5 and 9 Hz.), 5.03 (C$_{(6)}$-H, d, J 5 Hz.) and 6.57 and 6.81 (C$_{(2)}$-CH$_2$, AB-q J$_{AB}$ 18 Hz.).

EXAMPLE 4

Diphenylmethyl 7β-(2-thienylacetamido)-3-(pent-1-enyl) ceph-3-em-4-carboxylate A solution of diphenylmethyl 7β-(2-thienylacetamido)-3-(triphenylphosphoranylidenemethyl)ceph-3-em-4-carboxylate (250 mg.) and n-butyraldehyde (10 ml.) in dry methylene chloride (10 ml.) was heated to reflux for 24 hours. The solvent was evaporated in vacuo and the residue dissolved in ethyl acetate. Addition of petroleum-ether to this solution yielded an oily solid, which was purified by preparative TLC on Kieselgel PF$_{254+366}$ to give a white solid (18 mg., 10%), R$_F$ 0.6 (t.1.c.), λ$_{max.}$ 292 nm (ε7,200), inflexion at 237 nm. (ε 12,400); the p.m.r. spectrum (CDCl$_3$) indicated that this material consisted of the title compound mixed with another, unidentified material, and had signals at τ 3.99 (—CH=CH.CH$_2$CH$_2$CH$_3$, d, J 13 Hz., i.e. cis-isomer), 4.23 (dd, J 4.5 and 9 Hz.), 4.50 (dd, J 4.5 and 9 Hz.), 4.64 (=CH.CH$_2$CH$_2$CH$_3$, unresolved m), 5.55 (d, J 4.5 Hz.) 6.31 and 6.90 (AB-q J$_{AB}$ 18 Hz.) and 8.34 (m), 8.76 (m) and 9.23 (m), (-CH$_2$CH$_2$CH$_3$).

EXAMPLE 5

(a) Diphenylmethyl 3-(but-1-enyl)-7β-(2-thienylacetamido)-ceph-3-em-4-carboxylate, cis- and trans-isomers Diphenylmethyl 3-(triphenylphosphoranylidenemethyl)-7β-(2-thienylacetamido)ceph-3-em-4-carboxylate (1.528 g., 2 mmole) was dissolved in a mixture of freshly distilled propionaldehyde (25 ml., 350 mmole) and dry methylene chloride (25 ml.). The solution was stirred at 25° or 16 hours, the solvent and residual propionaldehyde removed by rotary evaporation, and the residue dissolved in methylene chloride (200 ml.). The resulting solution was washed successively with N-hydrochloric acid (200 ml.), 2N-aqueous sodium bicarbonate (200 ml.), water (200 ml.), brine (100 ml.), dried and evaporated to a yellow foam. This material was purified by column cchromatography on Kieselgel. Combination of similar fractions (as judged by TLC) gave the title compound as pale yellow crystals (110 mg., 10%), R$_F$ 0.70, m.p. 156°-158° (decomp.), [α]$_D$ − 10° (THF), λ$_{max.}$ 289 nm. (ε8,700) inflexion at 235 nm. (ε 14.600), νmax. (CHBr$_3$) (—NH) 1782 (β-lactam), 1720 and 1230 (ester) 1684 and 1510 (-CONH-) cm.$^{-1}$; the p.m.r. spectrum indicated that the compound was mainly the cis-isomer (with ca. 15% trans), with signals at τ 3.98 (—CH=CH.CH$_2$CH$_3$, d, J = 11 Hz.), 4.23 (C$_{(7)}$H, dd, J 5 and 9 Hz.), 4.61 (=CH.CH$_2$CH$_3$, complex m), 5.04 (C$_{(6)}$H, d, J 5 Hz.), 6.6 and 6.83 (C$_{(2)}$-CH$_2$, AB-q,J$_{AB}$ 18 Hz.), 8.22 (-CH$_2$CH$_3$, complex m), 9.18 (—CH$_2$CH$_3$, methyl t, J 8 Hz.), [Found: C, 66.25; H, 5.2; N, 5.1; S, 11.6; C$_{30}$H$_{28}$N$_2$O$_4$S$_2$ (544.7) requires C, 66.15; H, 5.2; N, 5.1; S, 11.8%].

(b) 7β-(2-Thienylacetamido)-3-(but-1-enyl)ceph-3-em-4-carboxylic acid, cis-isomer A solution of diphenylmethyl 7β(2-thienylacetamido)-3-(but-1-enyl)ceph-3-em-4-carboxylate (460 mg., 0.845 mmole) in trifluoroacetic acid (2.0 ml.) and anisole (0.5 ml.) was stirred for 5 minutes at room temperature. The solvents were removed in vacuo, and the residue partitioned between ethyl acetate and 2N-sodium bicarbonate solution. Acidification (to pH 2) of the bicarbonate solution gave the acid (293 mg. 92%). Trituration of this material with ethyl acetate gave pure 7β-(2-thienylacetamido)-3-(but-1-enyl)ceph-3-em-4-carboxyklic acid (127 mg.) as a crystalline solid, m.p. 165°-170° (decomp.), [α]$_D$ + 41° (dioxan), λλ$_{max.}$ (0.1M-phosphate buffer; pH 6) 280.5 nm. (ε 9,900), 234.5 nm. (ε 12,800), ν$_{max.}$ 3430 (—NH), 1775 (β-lactam), 1700 (—CO$_2$H), and 1655 and 1525 cm$^{-1}$ (—CONH—); the p.m.r. spectrum indicated that the compound was the cis-isomer, with signals at τ (D$_2$O with sodium bicarbonate) 4.07 (—CH=CH.CH$_2$CH$_3$, d, J 11.5 Hz.), 4.41 (C$_{(7)}$-H, d, J 4.5 Hz.), 4.47 (—CH=CH.CH$_2$CH$_3$, dt, J 11.5 and 7.5 Hz.), 4.97 (C$_{(6)}$-H, d, J 4.5 Hz.), 6.50 and 6.81 (C$_{(2)}$—CH$_2$, AB-q J$_{AB}$ 18 Hz.), 7.99 (—CH$_2$CH$_3$, unresolved m), 9.06 (—CH$_2$CH$_3$, t, J 7.5 Hz.), R$_F$ 0.82(System C) and R$_F$0.67 (System B, but using Whatman No. 1 paper) [Found: C, 52.8; H, 4.75; N, 7.1; S, 16.6. C$_{17}$H$_{18}$N$_2$O$_4$S$_2$. ½H$_2$O (387.5) requires C, 52.7; H, 4.9; N, 7.2; S, 16.55%].

EXAMPLE 6

Diphenylmethyl 3-(prop-1-enyl)-7β-(2-thienylacetamido) ceph-3-em-4-carboxylate, cis- and trans-isomers

[4-Diphenylmethoxycarbonyl-7β-(2-thienylacetamido) ceph-3-em-3-ylmethyl] tri-n-butylphosphonium iodide (1.4 g., 1.7 mmole) was dissolved in dry methylene chloride (200 ml.), and acetaldehyde (6 ml., 106 mmole) added. The solution was stirred at 0°, in the dark, under dry nitrogen and treated, over 15 minutes, with 0.1N-sodium hydroxide (385 ml. ca. 23 equiv.). The solution was stirred for a further 2 hours at room temperature, added to a mixture of 2N-hydrochloric acid (30 ml.) and water (250 ml.), and the organic phase separated, washed successively with saturated sodium bicarbonate (2 × 150 ml.), water (2 × 200 ml.), brine (2 × 200 ml.), dried and evaporated to an oil. This material was purified by chromatography on 0.05 - 0.2 mm. Kieselgel with benzene:ethyl acetate = 8:1 as eluent. Combination of fractions, R$_F$0.58, gave the title compound as a pale yellow solid (147 mg., 16%) m.p. 110°-115° (decomp.), ε$_{max.}$ 285 nm. (ε 7,400), λ$_{inf.}$ 235 nm. (ε 13,600) ν$_{max.}$ (CHBr$_3$) 3400 (—NH), 1780 (β-lactam), 1720 (—CO$_2$R), 1680 and 1520 (—CONH—) cm$^{-1}$; the p.m.r. spectrum (CDCl$_3$) indicated that the compound was a mixture of cis- and trans-isomers (∼7:3) with signals at τ 3.96 (—CH=CH.CH$_3$, d, J 12 Hz.), 4.24 (C$_{(7)}$—H, dd, J 5 and 9 Hz.), 4.51 (=CH.CH$_3$, dd, J 12 and 7 Hz.), 5.02 (C$_{(6)}$—H, d, J 5 Hz.), 5.02 (C$_{(6)}$—H, d, J 5 Hz.), 6.57 and 6.85 (C$_{(2)}$—CH$_2$, AB-q,J$_{AB}$ 18 Hz.) and 8.61 (—CH=CH.CH$_3$, methyl dd, J 7 and ca. 0.5 Hz.) for the cis-isomer and at τ 3.95 (-CH=CH. CH$_3$, d, J 16 Hz.), 4.28 (C$_{(7)}$-H, dd, J 4.5 and 9 Hz.), 4.47 (=CH.CH$_3$dd, J 16 and 7 Hz.) 5.06 (C$_{(6)}$—H, d, J 4.5 Hz.), 6.57 (C$_{(2)}$—CH$_2$, s) and 8.27 (—CH=CH.CH$_3$, methyl dd, J 7 and ca. 1 Hz.).

EXAMPLE 7

Diphenylmethyl 7β-(2-thienylacetamido)-3-vinyl-ceph-3-em-4-carboxylate, 1β-oxide A solution of (4-diphenylmethoxycarbonyl-7β-(2-thienylacetamido)ceph-3-em-3-ylmethyl)-triphenylphosphonium bromide, 1β-oxide (862 mg., 1 mmole) in methylene chloride (100 ml.) was stirred at room temperature with 40% formaldehyde solution (2.0 ml., 27 mmole) and treated, over 30 minutes, with 0.1N-sodium hydroxide solution (230 ml., 23 equivs.). The mixture was stirred for a further 3 hours at room temperature, and added to 2N-aqueous hyorochloric acid (13 ml.) in water (150 ml.). The organic phase was separated, washed successively with 2N-sodium bicarbonate solution (2 × 100 ml.), water (3 × 150 ml.), and brine (2 × 200 ml.), dried and evaporated to an oil. This oil was dissolved in ethyl acetate (3 ml.), benzene (10 ml.) was added and the white precipitate (64 mg., 12%) collected by filtration. Comparison with an authentic sample indicated this to be a mixture of the title compound, R$_F$ 0.58 and an unidentified component, $R_F$ 0.69; $\lambda_{max.}$ (CHCl$_3$) 300 nm. ($\epsilon$ 7,000).

EXAMPLE 8

Diphenylmethyl 7β-(2-thienylacetamido)-3-(prop-1-enyl)ceph-3-em-4-carbonxylate, 1β-oxide A solution of [4-diphenylmethoxycarbonyl-7β-(2-thienylacetamido)ceph-3-em-3-ylmethyl] triphenylphosphonium bromide, 1β-oxide (862 mg. 1 mmole) and acetaldehyde (3.0 ml., 53 mmole) in methylene chloride (100 ml.) was stirred at room temperature and treated, over 30 minutes, with 0.1N-sodium hydroxide solution (230 ml., ca. 23 equivs.). The two-phase mixture was stirred for a further 60 minutes at room temperature and poured into 2N-hydroxyloric acid (20 ml.) and water (100 ml.). The organic phase was separated, washed successively with saturated sodium bicarbonate (3 × 100 ml.), water (3 × 75 ml.), and brine (2 × 100 ml.), dried and evaporated to a yellow gum. This material was purified by chromatography over 0.05-0.2 mm. Kieselgel with benzene:ethyl acetate = 8:1 as eluent. Combination of similar fractions (as judged by TLC) gave the title compound (55 mg., 10%), $R_F$ 0.22, as a white solid, m.p. 172°-173.5° (decomp.), $[\alpha]_D - 97.5°$ (N,N-dimethylformamide), $\nu_{max}$(CHBr$_3$) 3350 (—NH), 1790 (α-lactam), 1715 (CO$_2$R), 1675 and 1520 (CONH) and 1040 cm$^{-1}$ (S→O), $\lambda_{max.}$ (CHCl$_3$) 301 nm. ($\epsilon$ 8,100); the p.m.r. spectrum (CDCl$_3$) indicated that the compound was the cis-isomer and had signals at $\tau$ 4.01 (—CH=CH.CH$_3$, d, J 12 Hz.), 4.01 (C$_{(7)}$-H, dd, J 4 and 9 Hz.), 4.50 (=CH.CH$_3$, dd, J 12 and 7 Hz.), 5.56 (C$_{(6)}$-H, d, J 4 Hz.), 6.32 and 6.90 (C$_{(2)}$-CH$_2$, AB-q,J$_{AB}$ 18 Hz.) and 8.59 (CH=CH.CH$_3$, methyl dd, J 7 and ca. 0.5 Hz.) [Found C, 62.4; H, 4.9; N, 4.5; S, 10.6. C$_{29}$H$_{24}$N$_2$O$_5$S$_2$ (546.6) requires C, 63.8; H, 4.8; N, 5.1; S, 11.7%].

EXAMPLE 9

Diphenylmethyl 7β-(2-thienylacetamido)-3-vinylceph-3-em-4-carboxylate

A solution of [4-diphenylmethoxycarbonyl-7β-(2-thienylacetamido)ceph-3-em-3-ylmethyl] triphenylphosphonium iodide (430 mg.), $R_F$ 0.0, in methylene chloride (10 ml.) was shaken with 5%-sodium bicarbonate solution (10 ml.) for five minutes. The separated organic layer was treated with 40%-formaldehyde solution (2 ml.) and 5% aqueous sodium bicarbonate solution (5 ml.) and the mixture stirred vigorously at room temperature until the chromophore of the starting material at 388 nm. had disappeared (ca. 30 minutes). The organic layer was separated and washed with 0.5N-hydrochloric acid and water, then dried and evaporated in vacuo. The residue was crystallised from methanol to give diphenylmethyl 7(2-thienylacetamido)-3-vinylceph-3-em-4-carboxylate (90 mg. 36%), $R_F$ 0.5, as needles, $\lambda_{max.}$ 296 nm. ($\epsilon$ 13,200), identified by infrared spectroscopy with material described previously.

EXAMPLE 10

(a) Diphenylmethyl 7β-amino-3-vinylceph-3-em-4-carboxylate

A suspension of phosphorus pentachloride (4.71 g., 22.5 mmole) in methylene dichloride (35 ml.) was warmed uuntil most of the phosphorus pentachloride had dissolved. A solution of pyridine in methylene dichloride (18.2 ml., as a 10% v:v solution, ca22.5 mmole pyridine) was added, and the white suspension was warmed to 23° for 10 minutes, then cooled to 0°. A solution of diphenylmethyl 7β-(2-thienylacetamido)-3-vinylceph-3-em-4-carboxylate (5.16 g., 10 mmole) in methylene dichloride (70 ml.), cooled to 0°, was added and the mixture stirred for 20 minutes. The solution was run into a vigorously stirred mixture of methanol (10 ml.) in methylene dichloride (50 ml.) and the resulting solution washed with aqueous sodium bicarbonate and water, and dried and evaporated in vacuo. The residual gum, in a small volume of chloroform, was run onto a column (7 × 4 cm.) of Kieselgel (0.02 to 0.5 mm.), and the column eluted with chloroform (2 × 100 ml.), then chloroform:ethyl acetate = 1:1 (3 × 100 ml.). The first chloroform fraction and the last chloroform : ethyl acetate fraction were discarded and the other fractions combined and evaporated in vacuo. The residue was triturated with ether to give the amine (2.7 g., 69%) as small needles, m.p 157°-160° (decomp), $[\alpha]_D - 155.4°$ (CHCl$_3$), $\lambda_{max.}$ 296.5 nm. ($\epsilon$, 12,400), $\nu_{max.\ (CHBr3)}$ 3460 and 3390 (NH), 1780 (β-lactam), 1730 (CO$_2$R) and 910 cm.$^{-1}$ (CH=CH$_2$), $\tau$ (CDCl$_3$) 2.65 (Ph), 3.02 (CH Ph$_2$), 33.09 (CH=CH$_2$, dd, J 11 and 18 Hz.), 4.64 and 4.82 (CH=CH$_2$, two d, J 18 and 11 Hz. resp.), 5.09 (C$_{(7)}$-H, d, J 5 Hz.), 5.32 (C$_{(6)}$-H, d, J 5 Hz.), 6.35 (C$_{(2)}$-CH$_2$, AB-q J 18 Hz), and 8.21 (NH$_2$); (DMSO-d$_6$) 2.60 (Ph), 3.03 (CH Ph$_2$), 3.28 (CH = CH$_2$, dd J 11 and 17 Hz.), 4.40 and 4.76 (CH=CH$_2$, two d, J 17 and 11 Hz. resp.), 4.91 (C$_{(7)}$-H, d, J 5 Hz.), 5.12 (C$_{(6)}$-H, d, J 5 Hz), 6.09 and 6.45 (C$_{(2)}$-CH$_2$, AB-q J 18 Hz.) and 7.62 (NH$_2$) (Found: C, 66.2; H, 5.1; N, 6.8; S, 8.1. C$_{22}$H$_{20}$N$_2$O$_3$S requires C, 67..3; , H, 5.15; N, 7.15; S, 8.2%).

(b) Diphenylmethyl 7β-(D-2-t-butoxycarbonylamino-2-phenylacetamido)-3-vinylceph-3-em-4-carboxylate A solution of diphenylmethyl 7β-amino-3-vinylceph-3-em-4-carboxylate (1.57 g., 4 mmole) in methylene dichloride (25 ml.) with dicylohexylcarbodiimide (907 mg., 4.4 mmole) was treated slowly (over 10 minutes) with a solution of D-2-t-butoxycarbonylamino-2-phenylacetic acid (1.1 g., 4.4 mmole) in N,N-dimethylformamide (10 ml.). The mixture was stirred at 23° for 30 minutes and dicyclohexylurea removed by filtration. The filtrate was wahsed with water and dried and evaporated in vacuo to give a pale yellow solid. This material was crystallised from methanol, and the isolated material washed with ether, to give the crude title compound (2.2 g.) (contaminated with dicyclohexlurea). The crude compound in benzene ethyl acetate (2:5) was filtered through a short column of Kieselgel 0.02 - 0.5 mm., 10 cm. × 2.5 cm.). Evaporation of the solvent in vacuo and washing with crystalline residue with ether gave the pure title compound (1.6 g., 64%) as small needles m.p. 200°-202°, $[\alpha]_D - 129°$ (CHCl$_3$), $\lambda_{max}$ 294.5 nm. ($\epsilon$ 14,400), $\nu_{max.}$ 3395 (NH), 1780 (β-lactam), 1712 (CO$_2$R), 1690 and 1500 (CONH) and 912 cm.$^{-1}$ (CH=CH$_2$), $\tau$(CDCl$_3$) 3.05 (CHPh$_2$), 3.03 (CH=CH$_2$, dd, J 17 and 11 Hz). 3.08 (NH, d, J 9 Hz) 4.23 (C$_{(7)}$-H, dd, J 9 and 4.5 Hz), 4.28 (CH-NH, d, J 7 Hz), 4.65 and 4.79 (CH=CH$_2$, two d, J 17 and 11 Hz resp.), 4.77 (CH-NH, d, J 7 Hz), 5.10 (C$_{(6)}$-H, d, J 4.5 Hz), 6.46 and 6.70 (C$_{(2)}$—CH, AB-q, J 18 Hz) 8.58 (C[CH$_3$]$_3$). (Found: C, 66.6; H, 5.6; N, 6.4; S, 5.1. C$_{35}$H$_{35}$N$_3$O$_6$S requires C, 67.2; H, 5.65; N, 6.7; S, 5.1%).

(c) 7β-(D-2-Amino-2-phenylacetamido)-3-vinylceph-3-em-4-carboxylic acid

A solution of diphenylmethyl 7β-(D-2-t-butoxycarbonylamino-2-phenylacetamido)-3-vinylceph-3-em-4-carboxylate (1.4 g.) in anisole (1.4 ml.) was treated, at 23°, with trifluoroacetic acid (5.6 ml.). After 4 minutes the solvents were removed in vacuo and the residue partitioned between ethyl acetate and water containing trifluoroacetic acid (ca 0.25 ml.). The aqueous phase was separated and the ethyl acetate washed thoroughly with more dilute aqueous trifluoroacetic acid (6 × 30 ml.). Traces of ethyl acetate were removed from the aqueous solution in vacuo and after ca 30 minutes at room temperature material (221 mg.) which had crystallised out was isolated by filtration. The aqueous solution was freeze dried and the residue taken up in a small volume of water (ca 20 ml.) and a second crop (350 mg.) of crystalline material was isolated by filtration. The crystalline material was combined to give the title compound (571 mg.) as small prisms m.p. 190° (decomp.), $[\alpha]_D - 96.2°$ (5% $NaHCO_3$), $\lambda_{max}$ (0.2 m pH 7 phosphate buffer) 287.5 nm. ($\epsilon$ 11,360), $\nu_{max}$ ca 3540 ($H_2O$), 2600 ($NH_3$), 1750 (β-lactam), 1690 and 1530 (—CONH—), 1570 (—$CO_2$) and 920 cm.$^{-1}$ (C=$CH_2$), τ ($CF_3CO_2H$) 2.2 (—$N^+H_3$), 2.42 (phenyl), 2.63 (CH=$CH_2$, dd, J 17 and 11 Hz), 4.22 ($C_{(7)}$-H, partially obscured dd), 4.24 and 4.36 (CH=$CH_2$, two d, J 17 and 11 resp.), 4.46 (CH-$NH_3$, ill resolved q), 4.78 ($C_{(6)}$-H, d, J 4.5 Hz) and 6.37 ($C_{(2)}$-$CH_2$), (Found: C 51.7; H, 5.2; N, 11.0; S, 8.1. $C_{17}H_{17}N_3O_4S$. $2H_2O$ requires C, 51.6; H, 5.35; N, 10.65; S, 8.1%). Rf. 0.15 (System B)

EXAMPLE 11

(a) t-Butyl 7β-Phenoxyacetamido-3-vinylceph-3-em-4-carboxylate

A solution of [4-t-butoxycarbonyl-7β-phenoxyacetamidoceph-3-em-3-ylmethyl]-triphenylphosphonium bromide (1.49 g, 2 mmole) in methylene chloride (30 ml) was treated successively with 40% formaldehyde solution (9 ml) and 3%-aqueous sodium hydrogen carbonate solution (30 ml.). The two-phase mixture was stirred at ca. 25° for 30 minutes, when the aqueous phase was separated and extracted with methylene chloride (30 ml.). The combined organic phases were washed with 2N-hydrochloric acid, water and brine (30 ml of each), dried ($MgSO_4$), and evaporated. The residue was chromatographed on Kieselgel G (Merck; 50 g) using 2.5, 10 and then 20% acetone in methylene chloride as eluants. Appropriate fractions were combined and evaporated to a foam (0.595 g) which was crystallised from ethanol to give the title ester (0.352 g, 42.5%), m.p. 98.5° to 100°, $[\alpha]_D^{22}$ − 47° (C 1.08; $Me_2SO$), $\lambda_{max}$(MeOH) 292 nm ($\epsilon$ 14,650) with inflexions at 270 and 277 nm ($\epsilon$ 10,000 and 12,200), $\nu_{max}$ (Nujol) 3350 (NH), 1778 (azetidin-2-one), 1708 ($CO_2R$), 1678 and 1522 (CONH) and 911 cm$^{-1}$(=$CH_2$), τ ($Me_2SO$-$d_6$) 0.84 (1H, d, J 8Hz; NH), 2.66 and 2.99 (2H and 3H, 2 m; $C_6H_5O$), 3.17 (1H, dd, J 11 and 18 Hz; CH=$CH_2$), 4.24 (1H, dd, J 8 and 5 Hz; $C_7$-H), 4.36 (1H, d, J 18 Hz) and 4.65 (1H, d, J 11 Hz) (CH=$CH_2$), 4.79 (1H, d, J 5Hz; $C_6$-H), 5.36 (2H, s; $C_6H_5OCH_2$), 6.09 and 6.44 (2 H, AB-q, J 18 Hz; $C_2$-$H_2$), 8.48 (9H, s; $CO_2C(CH_3)_3$) (Found: C, 60.1, 60.4; H, 5.8, 5.8; N, 6.3, 6.5; S, 7.7. $C_{21}H_{24}N_2O_5S$ (416.5) requires C, 60.6; H, 5.8; N, 6.7; S, 7.7%).

(b) 7β-Phenoxyacetamido-3-vinylceph-3-em-4-carboxylic Acid t-Butyl 7β-phenoxyacetamido-3-vinylceph-3-em-4-carboxylate (1.67 g, 4 mmole) was dissolved in trifluoroacetic acid (16 ml), and anisole (5 ml) was added at once. The solution was kept at ca. 25° for 10 minutes, when the solvents were removed in vacuo. The residue was distributed between ethyl acetate (75 ml) and 3%-aqueous sodium hydrogen carbonate solution (75 ml). The organic phase was re-extracted with bicarbonate solution (50 ml) and the combined aqueous extracts were acidified to pH 2 with concentrated hydrochloric acid, and extracted with ethyl acetate (3 × 50 ml). The combined ethyl acetate extracts were washed with water (100 ml) dried ($MgSO_4$), and evaporated to a pale-orange foam (1.495 g). Crystallisation from ethanol (ca. 10 ml) with slight warming, followed by refrigeration at −16° for 2 hours gave the title acid as a white fluffy solid (1.05 g, 73%), m.p. 95° to 97°, $[\alpha]_D^{24}$ −26.8° (C 1.01; $Me_2SO$), $\lambda_{max}$ (EtOH) 290.5 nm ($\epsilon$ 14,300), inflexions at 271 and 278.5 nm ($\epsilon$ 10,400 and 12,300), $\nu_{max}$ (Nujol) 3300 (NH), 1770 (azetidin-2-one), ca. 2600 and 1710 ($CO_2H$), 1670 and 1530 (CONH) and 917 cm$^{-1}$ (=$CH_2$); τ ($Me_2SO$-$d_6$) 0.83 (1H, d, J 8.5 Hz; NH), 2.66 and 2.99 (2H and 3H, 2 m; $C_6H_5O$), 3.00 (1H, partly obscured dd, J 11 and 18 Hz; CH=$CH_2$), 4.23 (1H, dd, J 8.5 and 4.5 Hz; $C_7$-H), 4.36 (1H, d, J 18 Hz) and 4.65 (1H, d, J 11 Hz) (CH=$CH_2$), 4.81 (1H, d, J 4.5 Hz; $C_6$-H), 5.36 (2H, s; $C_6H_5OCH_2$), 6.09 and 6.41 (2H, AB-q, J 18 Hz; $C_2$-$H_2$), 6.50 and 8.91 (0.2 mole ethanol) (Found: C, 54.45; H, 4.6; N, 7.2; S, 8.2, 8.3. $C_{17}H_{16}N_2O_5S$ (360.4) requires C, 56.65; H, 4.5; N, 7.8; S, 8.9%), $R_F$(System A) 1.67.

EXAMPLE 12 t-Butyl 7β-Phenoxyacetamido-3-vinylceph-3-em-4-carboxylate

A solution of t-butyl 3-bromomethyl-7β-phenoxyacetamidoceph-3-em-4-carboxylate, 1β-oxide (24.97 g, 50.5 mmole) and triphenylphosphine (16.4 g, 1.25 equiv.) in dry methylene chloride (300 ml) was stirred at ca. 20° for 16 hours and then cooled to −20°. A solution of phosphorus tribromide (7.34 ml, 1.5 equiv.) in dry methylene chloride (100 ml) was added with stirring over a period of 30 minutes with the reaction temperature being maintained at −20°; the mixture was then stirred at this temperature for a further hour. 40%-Formaldehyde solution (190 ml) and saturated aqueous sodium hydrogen carbonate solution (750 ml) were added in one portion, and the two-phase mixture was stirred vigorously while its temperature was allowed to reach 20° and then held at this temperature for a further hour. The organic phase was washed with water, dried ($MgSO_4$), and evaporated, and the residue was chromatographed on Kieselgel G (Merck, 0.05 to 0.2 mm, 800 g), eluting with benzene-ethyl acetate (15:1) and (10:1) (2 liters of each). Appropriate fractions were combined and evaporated to give the title ester as a pale-yellow foam (13.53 g, 63%), $[\alpha]_D$ − 44° (C 1.00; $Me_2SO$), $\lambda_{max}$ (EtOH) 292.5 nm ($\epsilon$ 15,300), inflexions at 269.5 and 276.5 nm ($\epsilon$ 10,000 and 12,400), having a p.m.r. spectrum ($Me_2SO$-$d_6$) similar to that described in Example A (iii) 11(a)

EXAMPLE 13

(a) t-Butyl 7β-Amino-3-vinylceph-3-em-4-carboxylate Hydrogen p-Toluene-sulphonate A solution of t-butyl 7β-phenoxyacetamido-3-vinylceph-3-em-4-carboxylate (833 mg, 2 mmole) in dry methylene chloride (10 ml) was maintained at 0° while dry pyridine (237 mg, 1.5 equiv.) and phosphorus pentachloride (625 mg) were added. The suspension was allowed to warm to 23° over a period of 15 minutes (by which time all the solid had dissolved) and then stirred at this temperature for 1¾ hours. The orange solution was added dropwise to stirred, dry methanol (5 ml) previously cooled to −20°; the temperature of the methanol solution was kept at ca. −20° throughout the addition. The solvents were removed in vacuo and the residual oil was partitioned between water (5 ml) and ethyl acetate (10 ml.) The aqueous phase was washed with ethyl acetate (5 ml) and the combined organic phases were back-washed with 0.5 N-hydrochloric acid (5 ml). The aqueous phase and acid washings were combined and treated with a solution of p-toluenesulphonic acid monohydrate (380 mg, 2 mmole) in water (2 ml), when refrigeration at 5° for 30 minutes failed to give any solid. Ethyl acetate (5 ml) was added and the pH of the mixture was adjusted to 4.9 with 2N-sodium hydroxide solution. The aqueous phase was reextracted with ethyl acetate (5 ml). and the combined ethyl acetate extract was washed with water (10 ml), dried (MgSO$_4$) and evaporated to low volume. Addition of a solution of p-toluenesulphonic acid monohydrate (380 mg, 2 mmole) in ethyl acetate (15 ml) caused the separation of a white solid. The mixture was refrigerated for 1 hour when the solid was filtered off, washed with ethyl acetate and dried to give the title p-toluenesulphonate (467 mg, 51%), m.p. >200°, $[\alpha]_D^{22}$ − 80° (C 1.03; MeOH), $\lambda_{max}$ (MeOH) 293.5 nm ($\epsilon$ 14,350). Crystallisation from warm ethanol-ether gave a feathery solid. $[\alpha]_D^{23}$ − 82° (C 1.01; MeOH), $\lambda_{max}$ (MeOH) 222 and 295 to 296 nm ($\epsilon$ 15,700 and 15,300), $\nu_{max}$ (Nujol) ca., 2600 (NH$_3^+$), 1770 (azetidin-2-one), 1716 (CO$_2$R), 1142 (SO$_3^-$) and 906 cm$^{-1}$ (=CH$_2$), $\tau$ (Me$_2$SO-d$_6$) 2.45 (2H, d, J 8 Hz; CH=C-SO$_3^-$), 2.84 (2H, d, J 8 Hz; CH=C—CH$_3$), 3.11 (1H, dd, J 11.5 and 17.5 Hz; CH=CH$_2$), 4.28 (1H, d, J17.5 Hz) and 4.58 (1H, d, J 11.5 Hz) (CH=CH$_2$), 4.69 and 4.78 (1H and 1H, 2 d, J 5 Hz; C$_7$-H and C$_6$-H), 6.01 and 6.33 (2H, AB-q, J 18 Hz; C$_2$-H$_2$), 6.71 (3H, s; CH$_3$C$_6$H$_4$), 8.51 (9H, s; CO$_2$C(CH$_3$)$_3$) (Found: C, 52.3, 52.5; H, 5.9, 5.9; N, 5.8, 6.1; S, 14.2. C$_{20}$H$_{26}$N$_2$O$_6$S$_2$ (454.6) requires C, 52.8; H, 5.8; N, 6.2; S, 14.1%).

(b) ACYLATION OF t-BUTYL 7β-AMINO-3-VINYLCEPH-3-EM-4-CARBOXYLATE with (i) p-Nitrophenylacetic Acid A suspension of t-butyl 7β-amino-3-vinylceph-3-em-4-carboxylate hydrogen p-toluenesulphonate (1.14 g, 2.5 mmole) in methylene chloride (25 ml) was shaken with 4%-aqueous sodium hydrogen carbonate solution (10 ml) until the organic phase cleared. The aqueous phase was reextracted with methylene chloride (10 ml), and the combined organic phases were washed with water (10 ml) and dried (MgSO$_4$). The solution of t-butyl 7β-amino-3-vinylceph-3-em-4-carboxylate so obtained was stirred and treated with a solution of dicyclohexylcarbodiimide (515 mg, 1 equiv.) in dry methylene chloride (10 ml). A solution of p-nitrophenylacetic acid (453 mg, 1 equiv.) in methylene chloride (15 ml) was added over a period of 5 minutes and the mixture was stirred at 30° for 2 hours. The precipitated N,N'-dicyclohexylurea was filtered off, and the filtrate was washed with 3%-sodium hydrogen carbonate solution (50 ml), water (50 ml), 2N-hydrochloric acid (25 ml) and water (25 ml), dried (MgSO$_4$) and evaporated to an orange gelatinous solid. This solid was triturated with ethyl acetate (150 ml), the insoluble dicyclohexylurea was removed by filtration, and the filtrate was evaporated to give t-butyl 7β-(p-nitrophenylacetmido)-3-vinylceph-3-em-4-carboxylate (1.02 g, 92%) (see Table 1)

Similar acylations to that described in (i) were carried out with (ii) Phenylacetic Acid
(iii) S-Benzylthioacetic Acid
(iv) Phenylglyoxylic Acid
(v) p-Triphenylmethylaminophenylacetic Acid
(vi) S-Phenylthioacetic Acid
(vii) Cyanoacetic Acid
(viii) D(−)-α-Formyloxy-α-phenylacetic Acid
(ix) D(−)-α-Dichloroacetoxy-α-phenylacetic Acid
(x) Bromoacetic Acid
(xi) Phenylmalonic Acid Mono-t-Butyl Ester and these examples are summarised in Table 1. The infrared spectra (in bromoform) and p.m.r. spectra (in deuterochloroform) of the products from Example 13b(i) to (xi) were consistent with their being the appropriate t-butyl 7β-acylamido-3-vinylceph-3-em-4-carboxylate esters containing 5 to 20% by weight of N,N'-dicyclohexylurea and/or the appropriate N-acyl-N,N'-dicyclohexylurea.

Notes to Table 1

* Inflexion
+ Acid wash omitted
Δ NaHCO$_3$ wash replaced by wash with 0.2M pH 7 phosphate buffer (50 ml)
≠ NaHCO$_3$ and 2N-HCl washes both omitted.

Table 1

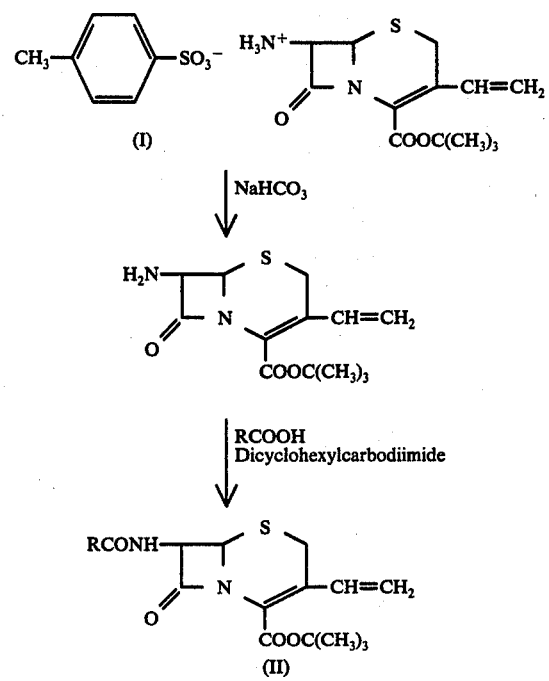

| Example | R. | Mmole of (I) and RCO₂H | % Wt. Yield of (II) | $\lambda_{max}$ nm | $E^{1\%}_{1cm}$ |
|---|---|---|---|---|---|
| 13b (i) | p-nitrobenzyl | 2.5 | 92 | 281 to 282 | 432 |
| 13b (ii) | benzyl | 3.5 | 88 | 293 | 232 |
| 13b (iii) | benzylthiomethyl | 3 | 70 | 294.5 | 317 |
| 13b (iv) | benzoyl | 3 | 90 | { 257.5 | 335 |
|  |  |  |  | 288 | 330 |
| 13b (v) | p-triphenylmethyl- | 3.5 | 90 | { 251 | 184 |
|  | aminobenzyl + |  |  | 276* | 144 |
| 13b (vi) | phenylthiomethyl | 3.5 | 90 | { 247 | 219 |
|  |  |  |  | 293 | 329 |
| 13b (vii) | cyanomethyl | 3.5 | 97 | 293 | 409 |
| 13b (viii) | D-α-formyloxybenzyl Δ | 1 | 92 | 293.5 | 284 |
| 13b (ix) | D-α-dichloroacetoxy benzyl ≠ | 2.66 | 103 | 293.5 | 233 |
| 13b (x) | bromomethyl | 5 | 100 | 294 | 335 |
| 13b (xi) | DL-α-t-butyloxy carbonylbenzyl | 3 | 89 | 293.5 | 264 |

EXAMPLE 13b (ix) cont t-Butyl 7β-(D-α-Hydroxy-α-phenylacetamido)-3-vinylceph-3-em-4-carboxylate

A solution of t-butyl 7β-(D-α-dichloroacetoxy-α-phenylacetamido)-3-vinylceph-3-em-4-carboxylate (1.42 g., 2.7 mmole) in methylene chloride (30 ml.) was stirred vigorously for 5 hours with 4% aqueous sodium hydrogen carbonate solution (30 ml.). The organic phase was washed with water (25 ml), dried (MgSO₄) and evaporated to an orange foam which was chromatographed on Kieselgel G (Merck, 0.05 to 0.2 mm; 50 g) with benzene-ethyl acetate (19:1; 300 ml.) and (9:1; 200 ml.) as eluant. The appropriate fractions were combined and evaporated to give the title ester as a pale-orange crystalline solid (485 mg., 43%), $\lambda_{max.}$ (EtOH) 294 nm (ε 13,750), τ (CDCl₃) 2.62 (5H, s; C₆H₅), 2.86 (1H, d, J 9 Hz; NH), 2.94 (1H, dd, J 11 and 18 Hz; CH═CH₂), 4.25 (1H, dd, J 9 and 5 Hz; C₇-H), 4.59 (1H, d, J 18 Hz) and 4.70 (1H, J 11 Hz) (CH═CH₂), 4.87 (1H, s; CHOH), 5.04 (1H, d, 5 Hz; C₆-H), 6.35 and 6.59 (2H, AB-q, J 18 Hz; C₂H₂), 8.47 (9H, s; CO₂C(CH₃)₃).

EXAMPLE 13b (x) cont t-Butyl 7β-(5-Methyl-1,3,4-thiadiazol-2-ylthioacetamido)-3-vinylceph-3-em-4-carboxylate A solution of 2-mercapto-5-methyl-1,3,4-thiadoazole (575 mg., 0.9 equiv.) in dioxan (10 ml.) was added to a solution of t-butyl 7β-bromoacetamido-3-vinylceph-3-em-4-carboxylate (1.95 g., 4.83 mmole) in dioxan (40 ml.), and the mixture was stirred while triethylamine (0.68 ml., 1 equiv.) was added. A precipitate formed at once. The suspension was stirred for 30 minutes, additional portions (40 mg., 0.06 equiv.) of the thiol being added after 10 and 20 minutes. The solvent was removed in vacuo and the residue was partitioned between ethyl acetate (50 ml.) and 2N-hydrochloric acid. The organic phase was washed with 4% sodium hydrogen carbonate solution and water (20 mg of each), dried (MgSO₄) and evaporated to give the title ester (2.08 g, 95%, $\lambda_{max.}$ (EtOH) 287 nm ($E^{1\%}_{1cm}$ 323), $\nu_{max.}$ (CHBr₃)

3390 and 3260 (NH), 1773 (azetidin-2-one), 1710 (CO$_2$R) and 1680 and 1516 cm$^{-1}$ (CONH), τ (CDCl$_3$) 1.81 (1H, d, J 9 Hz; NH), 2.91 (1H, dd, J 11 and 18 Hz; CH=CH$_2$), 4.18 (1H, dd, J 9 and 5 Hz; C$_7$-H), 4.59 (1H, d, J 18 Hz) and 4.70 (1H,d, J 11 Hz) (CH=CH$_2$), 5.02 (1H, d, J 5 Hz; C$_6$-H), 5.95 (2H, s; SCH$_2$), 6.34 and 6.59 (2H, AB-q, J 18 Hz; C$_2$-H$_2$), 7.28 (3H, s; CH$_3$-C=C), 8.47 (9H, s; CO$_2$C(CH$_3$)$_3$).

(c) DE-ESTERIFICATION OF t-BUTYL 7β-ACYLAMIDO-3-VINYLCEPH-3-EM-4-CARBOXYLATE ESTERS

The t-butyl esters listed below were treated with trifluoroacetic acid and anisole as in Example A(iii) 11(b) to give the corresponding 7β-acylamido-3-vinylceph-3-em-4-carboxylic acids. The physical properties of the products are summarised in Tables 2, 3 and 4.

(1) t-Butyl 7β-(p-Nitrophenylacetamido)-3-vinylceph-3-em-4-carboxylate (Example 13 (b)(i) cont).

(2) t-Butyl 7β-Phenylacetamido-3-vinylceph-3-em-4-carboxylate (Example 13 (b)(ii) cont).

(3) t-Butyl 7β-Benzylthioacetamido-3-vinylceph-3-em-4-carboxylate (Example 13 (b)(iii) cont).

(4) t-Butyl 7β-Phenylglyoxamido-3-vinylceph-3-em-4-carboxylate (Example 13 (b)(iv) cont).

(5) t-Butyl 7β-Phenylthioacetamido-3-vinylceph-3-em-4-carboxylate (Example 13 (b)(vi) cont).

(6) t-Butyl 7β-Cyanoacetamido-3-vinylceph-3-em-4-carboxylate (Example 13 (b)(vii) cont).

(7) t-Butyl 7β-(D-2-Formyloxy-2-phenylacetamido)-3-vinylceph-3-em-4-carboxylate (Example 13 (b)(viii) cont).

(8) t-Butyl 7β-(D-2-Hydroxy-2-phenylacetamido)-3-vinylceph-3-em-4-carboxylate (Example 13 (b)(ix) cont).

(9) t-Butyl 7β-(5-Methyl-1,3,4-thiadiazol-2-ylthioacetamido)-3-vinylceph-3-em-4-carboxylate (Example 13 (b)(x) cont).

Table 2

[Structure II: RCONH-β-lactam-S-CH=CH$_2$ with COOC(CH$_3$)$_3$]

CF$_3$COOH (TFA)
Anisole (An)

[Structure III: RCONH-β-lactam-S-CH=CH$_2$ with COOH]

| | | |
|---|---|---|
| In Example 13 (c)(1) | R is | p-nitrobenzyl |
| " (2) | R is | benzyl |
| " (3) | R is | benzylthiomethyl |
| " (4) | R is | benzoyl |
| " (5) | R is | phenylthiomethyl |
| " (6) | R is | cyanomethyl |
| " 0.19(7) | R is | screaking-for-myloxybenzyl |
| " (8) | R is | D-α-hydroxybenzyl |
| " (9) | R is | 5-methyl-1,3,4-thiadiazol-2-ylthiomethyl |

| Example | Mmole of II | ml of TFA An | % Yield of cryst.III | M.p. | λ$_{max}$ nm(ε) | [α]$_D$ | R$_f$ (system C) |
|---|---|---|---|---|---|---|---|
| 13(c)(1) | 2.45 | 12 3 | 63 | 210–217° | 280(18,650) | +14.3° | 1.56 |
| 13(c)(2) | 3.02 | 14 3.5 | 27 | 164–168° | 289.5(13,800) | −7.1° | 1.33 |
| 13(c)(3) | 2.93 | 12 3 | 60 | 85–86° | 292(14,400) | −52.3° | |
| 13(c)(4) | 2.65 | 12 3 | 41 | 152–162° | 258(14,300) 284(13,250) | −15.9° | 2.42 |
| 13(c)(5) | 3.10 | 14 3.5 | 77 | 96–98° | 251(9,650) 291(14,900) | −18.2° | 1.69 |
| 13(c)(6) | 3.32 | 14 3.5 | 72 | 201–209° | 290(15,800) | −21.4° | 0.21 |
| 13(c)(7) | 2.52 | 12 3 | 61 | 124–129° | 291(11,900) | −46.7° | 1.76* |
| 13(c)(8) | 1.10 | 5 1 | 77 | — | 290(11,300) | −60.8° | 0.84 |
| 13(c)(9) | 4.51 | 16 4 | 95 | 138–139° | 282.5(14,400) | −21.6° | 0.19 |

*With straking from R$_f$ 1.76 to R$_f$ 0.84

Table 3

Infrared spectra of $$\text{RCONH} \begin{array}{c} \text{S} \\ \diagup \\ \text{N} \end{array} \text{CH}=\text{CH}_2 \quad \text{(III)}$$
$$\text{O} \quad \text{COOH}$$

as Nujol mulls quoted in cm$^{-1}$

| Example | NH | azetidin-2-one | CO$_2$H | CONH | R |
|---|---|---|---|---|---|
| 13(c)(1) | 3275 | 1780 | 1710 | 1664 and 1531 | 1514 and 1341 (NO$_2$) |
| 13(c)(2) | 3260 | 1770 | 1700 | 1650 and 1530 | |
| 13(c)(3) | 3302 | 1780 | 1730 | 1658 and 1540 | |
| 13(c)(4) | 3270 | 1754 | 1720 | 1660 | 1680 (C$_6$H$_5$CO) |
| 13(c)(5) | 3252 | 1760 | 1711 | 1642 and 1520 | |
| 13(c)(6) | 3300 | 1770 | 1728 | 1668 and 1557 | 2294 (C≡N) |
| 13(c)(7) | 3315 | 1778 | 1710 | 1680 and 1540 | 1728 (OCHO) |
| 13(c)(8) | ca. 3300 | 1760 | 1695 | 1695 and 1505 | |
| 13(c)(9) | 3261 | 1750 | 1745 | 1697 and 1524 | |

Table 4

P.M.R. spectra in Me$_2$SO-d$_6$ solution of $$\text{RCONH} \begin{array}{c} \text{S} \\ \diagup \\ \text{N} \end{array} \text{CH}=\text{CH}_2 \quad \text{(III)}$$
$$\text{O} \quad \text{COOH}$$

quoted as τ values (coupling constants (J) in Hz shown in brackets)

| Example | CH=CH$_2$ dd | CH=CH$_2$ 2 doublets |
|---|---|---|
| 13(c)(1) | 3.05 (11 and 17) | 4.40(17), 4.67 (11) |
| 13(c)(2) | 3.05 (11 and 18) | 4.40(18), 4.68 (11.5) |
| 13(c)(3) | 3.04 (11 and 17) | 4.39(17), 4.67 (11) |
| 13(c)(4) | 3.00 (11.5 and 18) | 4.36(18), 4.65 (11.5) |
| 13(c)(5) | 3.05 (11 and 18) | 4.40(18), 4.68 (11) |
| 13(c)(6) | 3.02 (11 and 18) | 4.37(18), 4.65 (11) |
| 13(c)(7) | 3.08 (11 and 18) | 4.38(18), 4.70 (11) |
| 13(c)(8) | 3.04 (11 and 18) | 4.40(18), 4.67 (11) |
| 13(c)(9) | 3.02 (11 and 17.5) | 4.37(17.5), 4.65 (11) |

EXAMPLE 13 (b)(xi) cont

7β-(DL-α-Carboxy-α-phenylacetamido)-3-vinylceph-3-em-4-carboxylic Acid

A solution of t-butyl 7β-(DL-α-t-butoxycarbonyl-α-phenylacetamido)-3-vinylceph-3-em-4-carboxylate (1.31 g., 2.62 mmole) in anisole (6 ml.) and trifluoroacetic acid (24 ml.) was stirred at 25° for 15 minutes. The solvents were removed in vacuo to give an orange solid which was partitioned between ethyl acetate (100 ml.) and 4%-sodium hydrogen carbonate solution (100 ml.). The aqueous phase was washed with ethyl acetate (50 ml.), acidified to pH 2.0 with concentrated hydrochloric acid, and extracted with ethyl acetate (3 × 50 ml.). The combined extracts were washed with water (100 ml.), dried (MgSO$_4$), and evaporated to a pale-yellow solid (0.83 g.), which was triturated with ether (10 ml.) containing a few drops of acetone to give the title acid (0.545 g., 53.5%), m.p. 165°–167° (decomp), [α]$_D$ −24.8°, λ$_{max.}$ (EtOH) 291.5 nm (ε 13,800), ν$_{max.}$ (Nujol) 3280 (NH), 1762 (azetidin-2-one), 1692 (CO$_2$H) and 1680 and 1530 cm$^{-1}$ (CONH). The p.m.r. spectrum of the product in Me$_2$SO-d$_6$ showed it to be a mixture of two diastereoisomers τ 4.82 (C$_6$-H), 5.12 (C$_6$H$_5$CHCO$_2$H), and 4.92 (C$_6$-H), 5.10 (C$_6$H$_5$CHCO$_2$H) in a ratio of ca. 2:1. Addition of D$_2$O exchanged the α-proton and gave a 1:1-mixture of the two diastereoisomers.

EXAMPLE 14

2,2,2-Trichloroethyl 7β-Phenylacetamido-3-vinylceph-3-em-4-carboxylate.

40%-Formaldehyde solution (3 ml.) and 4%-sodium hydrogen carbonate solution (6 ml.) were added to a solution of [7β-Phenylacetamido-4-(2,2,2-trichloroethoxycarbonyl)ceph-3-em-3-ylmethyl]-triphenylphosphonium bromide (403 mg., 0.5 mmole) in methylene chloride (10 ml.), and the two phase mixture was stirred vigorously for 25 minutes. The organic phase was washed with 2N-hydrochloric acid and water (10 ml of each), dried (MgSO$_4$), and evaporated to an orange oil which was crystallised from ethanol (ca. 2 ml.) to give the title ester (22 mg., 9%), λ$_{max.}$ (EtOH) 297 nm (ε 14,100).

EXAMPLE 15

2,2,2-Trichloroethyl 7β-phenylacetamido-3-vinylceph-3-em-4-carboxylate

[7β-Phenylacetamido-4-(2,2,2-trichloroethoxycarbonyl) ceph-3-em-3-ylmethyl]-triphenylphosphonium bromide (403 mg, 0.5 mmole) was dissolved in N,N-dimethylformamide (10 ml.) and 40%-formaldehyde solution (3 ml.) was added. The solution was stirred vigorously while a solution of disodium hydrogen phosphate (400 mg.) in water (5 ml.) was added dropwise. A white crystalline solid, subsequently identified as the title ester, separated before the addition was complete. The reaction mixture was diluted with chloroform (5 ml.) and water (10 ml.), whereupon the solid dissolved. The aqueous phase was re-extracted with chloroform (25 ml.), and the combined organic phases were washed with 2N-hydrochloric acid (50 ml.) and water (4 × 25 ml.), dried (MgSO$_4$), and evaporated to give the title ester as a pale-yellow solid (128 mg., 54%), λ$_{max.}$ (EtOH) 297 nm (ε13,700). Crystallisation by trituration with ethanol (2 ml.) gave a white solid (75 mg., 31.5%), m.p. 163 to 165°, [α]$_D^{23}$ - 54° (C 1.15; Me$_2$SO), λ$_{max.}$ (EtOH) 297 nm (ε 13,550), ν$_{max.}$ (CHBr$_3$) 3410 (NH), 1772 (azetidin-2-one), 1730 (CO$_2$R), 1674 and 1500 (CONH) and 912 cm$^{-1}$ (=CH$_2$), τ (CDCl$_3$) 2.68 (5H, s; C$_6$H$_5$), 2.84 (1H, dd, J 11 and 18 Hz; CH=CH$_2$), 3.61 (1H, d, J 8 Hz; NH), 4.13 (1H, dd, J 8 and 5 Hz; C$_7$-H), 4.48 (1H, d, J 18 Hz) and 4.60 (1H, d, J 11 Hz) (CH=CH$_2$), 4.98 (1H, d, J 5 Hz; C$_6$-H), 4.99 and 5.25 (2H, AB-q, J 12 Hz; CH$_2$CCl$_3$), 6.30 and 6.53 (2H, AB-q J 18 Hz; C$_2$-H$_2$), 6.37 (2H, s; C$_6$H$_5$CH$_2$) (Found: C, 46.8, 47.1; H, 3.6, 3.6; Cl, 21.8; N, 5.5, 5.5; S, 6.5. C$_{19}$H$_{17}$Cl$_3$N$_2$O$_4$S (475.8) requires C, 48.0; H, 3.6; Cl, 22.4; N, 5.9; S, 6.7%).

EXAMPLE 16

(a) 2,2,2-Trichloroethyl 7β-Formamido-3-vinylceph-3-em-4-carboxylate

40%-Aqueous formaldehyde solution (4 ml.) and 4%-aqueous sodium hydrogen carbonate solution (6 ml.) were added to a vigorously stirred solution of [7β-formamido-4-(2,2,2-trichloroethoxycarbonyl)ceph-3-em-3-ylmethyl]-triphenylphosphonium bromide (357 mg., 0.5 mmole) in methylene chloride (20 ml.). The two-phase mixture was stirred for 45 minutes, and the organic phase was washed with 2N-hydrochloric acid and water (20 ml. of each), dried (MgSO$_4$), and evaporated to an oil (0.35 g). This was subjected to preparative-layer chromatography on Kieselgel G (Merck PF$_{254+366}$) using 20% acetone in methylene chloride as eluant to give the title ester as a cream foam (84 mg., 43.5%), λ$_{max.}$ (EtOH) 297.5 nm (ε 10,700), τ (CDCl$_3$) 1.69 (1H, s; CHO), 2.81 (1H, dd, J 11.5 and 18 Hz; CH=CH$_2$), 3.24 (1H, d, J 9 Hz; NH), 4.05 (1H, dd, J 9 and 4.5 Hz; C$_7$-H), 4.43 (1H, d, J 18 Hz) and 4.55 (1H, d, J 11.5 Hz) (CH=CH$_2$), 4.90 (1H, d, J 4.5 Hz; C$_6$-H), 4.94 and 5.20 (2H, AB-q, J 12 Hz; CH$_2$CCl$_3$), 6.22 and 6.45 (2H, AB-q, J 18 Hz; C$_2$-H$_2$).

(b) 2,2,2-Trichloroethyl 7β-Amino-3-vinylceph-3-em-4-carboxylate Hydrochloride 2,2,2-Trichloroethyl 7β-formamido-3-vinylceph-3-em-4-carboxylate (0.88 g., 2.3 mmole) was treated with dry methanol (5 ml.), when some solid crystallised. The suspension was cooled to ca. 5° and stirred while phosphorus oxychloride (0.53 ml.) was added dropwise. The reaction mixture was kept at ca. 5° for 30 minutes and diluted with ether (20 ml.); no solid separated. The solvents were evaporated and the residual oil was treated with ether (ca. 10 ml.) to give a white solid. The solid was filtered off, washed with ether, and dried to give the title hydrochloride (0.765 g., 85%), λ$_{max.}$ (MeOH) 295 nm (ε 10,150), ν$_{max.}$ (Nujol), ca. 2590 (N$^+$H$_3$), 1788 (azetidin-2-one), 1730 (CO$_2$R), and 946 cm$^{-1}$ (=CH$_2$), τ (Me$_2$SO-d$_6$), 2.86 (1H, dd, J 11 and 17.5 Hz; CH=CH$_2$), 4.13 (1H, d, J 17.5 Hz) and 4.45 (1H, d, J 11 Hz) (CH=CH$_2$), 4.64 (1H, d, J 5 Hz; C$_7$-H), 4.78 (1H, d, J 5 Hz; C$_6$-H), 4.81 and 4.98 (2H, AB-q, J 12 Hz; CH$_2$CCl$_3$), 5.92 and 6.24 (2H, AB-q, J 17 Hz; C$_2$-H$_2$), 6.31 (ca 1H, d, J$_{P-H}$ 11 Hz; ca. 0.1 M trimethyl phosphate) (Found: P, 0.78%).

EXAMPLE 17

2,2,2-Trichloroethyl 7β-Phenoxyacetamido-3-vinylceph-3-em-4-carboxylate.

40%-Aqueous formaldehyde (24 ml.) and 3%-sodium hydrogen carbonate solution (80 ml.) were added to a solution of [7β-phenoxyacetamido-4-(2,2,2-trichloroethoxycarbonyl) ceph-3-em-3-ylmethyl]-triphenylphosphonium bromide (4.93 g, 6 mmole) in methylene chloride (40 ml.). The two-phase mixture was stirred vigorously for 2 hours and the organic phase was washed with water (100 ml.), dried (MgSO$_4$), and evaporated to an orange foam. This foam was chromatographed on Kieselgel G (Merck; 150 g) with methylene chloride and 0.5%-acetone in methylene chloride as eluants. The appropriate fractions were combined and evaporated to a colourless oil which crystallised on addition of ether. The solvent was removed to give the title ester as a white solid (0.50 g, 17%), m.p. 136° to 140° (decomp), [α]$_D^{23}$ − 33° (c 1.01; Me$_2$SO), λ$_{max.}$ (EtOH), 296 nm (ε 12,100), ν$_{max.}$ (Nujol) 3300 (NH), 1764 (azetidin-2-one), 1716 (CO$_2$R), 1668 and 1509 (CONH) and 920 cm$^{-1}$ (=CH$_2$), τ (Me$_2$SO-d$_6$) 0.81 (1H, d, J 8 Hz; NH), 2.67 and 2.99 (2H and 3H, 2m; C$_6$H$_5$O), 3.01 (1H, dd, J 11 and 18 Hz; CH=CH$_2$), 4.19 (1H, dd, J 8 and 5 Hz; C$_7$-H), 4.24 (1H, d, J 18 Hz) and 4.55 (1H, d, J 11 Hz) (CH=CH$_2$), 4.71 (1H, d, J 5 Hz; C$_6$-H), 4.79 and 5.01 (2H, AB-q, J 12 Hz; CH$_2$CCl$_3$), 5.36 (2H, s; C$_6$H$_5$OCH$_2$), 5.98 and 6.34 (2H, AB-q, J 18 Hz; C$_2$-H$_2$).

EXAMPLE 18

Diphenylmethyl 7β-Phenoxyacetamido-3-vinylceph-3-em-4-carboxylate

40%-Aqueous formaldehyde solution (6 ml.) and 3%-sodium hydrogen carbonate solution (18 ml.) were added to a vigorously stirred solution of [4-diphenylmethoxycarbonyl-7β-phenoxyacetamidoceph-3-em-3-ylmethyl]-triphenylphosphonium bromide (1.28g., 1.5 mmole) in methylene chloride (12 ml.). The two phase mixture was stirred for 30 minutes and the organic phase was washed with 2N-hydrochloric acid and water (10 ml of each), dried (MgSO$_4$), and evaporated to an orange oil. This oil was chromatographed on Kieselgel G (Merck; 75 g) with benzene and 5%-ethyl acetate in benzene and eluants. The appropriate fractions were combined and evaporated to a white gel (306 mg.), which was triturated with ether (20 ml.) to give the title ester (193 mg., 24%), m.p. 130° to 132°, [α]$_D^{23}$ − 81° (c 1.18; Me$_2$SO), λ$_{max.}$ (EtOH) 294 nm (ε 14,200), ν$_{max.}$ (CHBr$_3$) 3420 (NH), 1785 (azetidin-2-one), 1722 (CO$_2$R), 1692 and 1522 (CONH) and 910 cm$^{-1}$ (=CH$_2$), τ (CDCl$_3$) 2.3 to 2.8 and 3.0 (12H and 4H, 2 m; (C$_6$H$_5$)$_2$CH, C$_6$H$_5$O and NH), 2.98 (1H, dd, J 12 and 18 Hz; CH=CH$_2$), 3.01 (1H, s; (C$_6$H$_5$)$_2$CH), 4.11 (1H, dd, J 9 and 5 Hz; C$_7$-H), 4.59 (1H, d, J 18 Hz) and 4.74 (1H, d, J 12 Hz) (CH=CH$_2$), 4.98 (1H, d, J 5 Hz; C$_6$-H), 6.47 (2H, s; C$_6$H$_5$OCH$_2$), 6.35 and 6.58 (2H, AB-q, J 18 Hz; C$_2$-H$_2$).

EXAMPLE 19

Diphenylmethyl 7β-Formamido-3-vinylceph-3-em-4-carboxylate

40%-Aqueous formaldehyde solution (10 ml.) and 3%-sodium hydrogen carbonate solution (30 ml.) were added to a vigorously stirred solution of [4-diphenylmethoxycarbonyl-7β-formamidoceph-3-em-3-ylmethyl]-triphenylphosphonium bromide (1.875 g., 2.5 mmole) in methylene chloride (20 ml.). The two-phase mixture was stirred for 25 minutes and the organic phase was washed with 2N-hydrochloric acid and water (20 ml of each), dried (MgSO$_4$), and evaporated to an orange foam (1.68 g.). This foam was chromatographed on Kieselgel G (Merck, 75 g.) with 10- and 17%-acetone in methylene chloride as eluants. The appropriate fractions were combined and evaporated to give the title ester as a pale-yellow crystalline solid (334 mg., 32%), m.p. 148° to 152° (decomp), [α]$_D^{23}$ − 66° (c 1.19; Me$_2$SO), λ$_{max.}$ (EtOH) 295 nm (ε 9,350), ν$_{max.}$ (CHBr$_3$), (NH), 1787 (azetidin-2-one), 1725 (CO$_2$R), and 1696 and 1500 cm$^{-1}$ (CONH), τ (CDCl$_3$) 1.78 (1H, s; CHO), 2.4 to 2.8 (10 H, m; (C$_6$H$_5$)$_2$CH), 2.96 (1H, dd, J 11 and 18

Hz; CH=CH$_2$), 3.01 (1H, s; (C$_6$H$_5$)$_2$CH), 3.29 (1H, d, J 9 Hz; NH), 4.12 (1H, dd, J 9 and 5 Hz; C$_7$-H), 4.55 (1H, d, J 18 Hz) and 4.72 (1H, d, J 11 Hz) (CH=CH$_2$), 5.02 (1H, d, J 5 Hz; C$_6$-H), 6.34 and 6.57 (2H, AB-q, J 18 Hz; C$_2$-H$_2$).

EXAMPLE 20 t-Butyl 7β-(D-2-t-Butoxycarbonylamino-2-phenylacetmido)-3-vinylceph-3-em-4-carboxylate A solution of [7β-(D-2-t-butoxycarbonylamino-2-phenylacetamido)-4-t-butoxycarbonylceph-3-em-3-ylmethyl] triphenylphosphonium iodide (1.565 g.) in methylene dichloride (40 ml.) was treated with 2½%- aqueous sodium bicarbonate solution (40 ml.) and 40%- aqueous formaldehyde solution (4 ml.), and the mixture was stirred vigorously for 25 minutes. The organic phase was separated and washed with 1N-hydrochloric acid and water, and dried and evaporated in vacuo. The residual foam (1.5 g.) was purified by chromatography on 0.05-0.2 mm. Kieselgel with benzene:ethyl acetate = 5:1, 4:1, and 3:1 as successive eluents. Combination of similar fractions (as judged by t.l.c.) gave the vinyl compound (350 mg.) as an amorphous solid, m.p. 114° to 128° (decomp.), [α]$_D$ −92.8° (CHCl$_3$), λ$_{max.}$ 293.5 nm. (ε 13,920), ν$_{max.}$ (CHBr$_3$) 3440 (NH), 1780 (β-lactam), 1720 (CO$_2$R), 1710 and 1500 (NHCO$_2$R), 1695 and 1510 (CONH) and 904 cm.$^{-1}$ (= CH$_2$), τ (CDCl$_3$) 2.96 (dd) and 4.62 (d) and 4.74 (d) (CH=CH$_2$, ABX-system, J$_{AX}$ 17 Hz., J$_{BX}$ 11 Hz., J$_{AB}$ 0 Hz.), 3.11 (NH, d, J 9 Hz), 4.21 (C$_{(7)}$-H, dd, J 4.5 and 9 Hz.), 4.3 (CHNH, d, J 7 Hz.), 4.78 (CHNH, d, J 7 Hz.), 5.1 (C$_{(6)}$-H, d, J 4.5 Hz.), 6.43 and 6.65 (C$_{(2)}$-CH$_2$, AB-q, J$_{AB}$ 18 Hz.) and 8.48 and 8.6 (t-butyl).

EXAMPLE 21

Diphenylmethyl 3-(Prop-1-enyl)-7β-(2-thienylacetamido)ceph-3-em-4-carboxylate

A solution of acetaldehyde (20 ml., 354 mmole) and benzoic acid (73 mg., 0.6 mmole) in dry methylene chloride (50 ml.) as stirred at 23° and treated, over 30 minutes, with diphenylmethyl 3-(triphenylphosphoranylidenemethyl)-7β-(2-thienylacetamido)ceph-3-em-4-carboxylate (1.528 g., 2 mmoles). After stirring for a further 4 hours, the solvent was removed in vacuo, the residue was extracted with ethyl acetate (50 ml.) and the insoluble material was filtered off; the filtrate was washed with saturated sodium bicarbonate (50 ml.), water (50 ml.) and brine (50 ml.), and dried and evaporated to a foam (1.58 g.). This material was purified by chromatography on 0.05-0.2mm. Kieselgel with benzene: ethyl acetate = 10:1 as eluent. Combination of similar fractions (as judged by t.l.c.) gave pale-yellow crystals of the title compound (178 mg., 17%), R$_f$ 0.58, m.p. 144° to 148° (decomp.), [α]$_D$ −25.9° (CHCl$_3$), λ$_{max.}$ 286.5 nm. (ε 7,900), with an inflexion at 237 nm. (ε 13,200); the p.m.r. spectrum indicated that the compound was mainly the cis-isomer (with 5–10% trans) with signals at τ 3.96 (—CH=CHCH$_3$, d, J 12 Hz.), 4.51 (=CHCH$_3$, dd, J 12 and 7 Hz.) and 8.61 (CH=CHCH$_3$, methyl dd, J 7 and 0.5 Hz.) [Found: C, 65.2; H, 5.0; N, 5.2; S, 11.9; C$_{29}$H$_{26}$N$_2$O$_4$S$_2$ (530.7) requires C, 65.6; H, 4.9; N, 5.3; S, 12.1%].

EXAMPLE 22

Diphenylmethyl 3-(2,2,2-Trichloroethoxycarbonylvinyl)-7β-(2-thienylacetamido)ceph-3-em-4-carboxylate A suspension of 2,2,2-trichloroethyl glyoxylate monohydrate (435 mg., 1.86 mmole) in dry methylene chloride (25 ml.) was stirred at 23° and treated, over 10 minutes, with diphenylmethyl 3-(triphenylphosphoranylidenemethyl)-7β-(2-thienylacetamido)ceph-3-em-4-carboxylate (765 mg., 1 mmole). After stirring for 45 minutes, the solvent was removed in vacuo and the residue was extracted with ethyl acetate (50 ml.); the insoluble material was filtered off and the filtrate was washed well with water (2 × 50 ml.) and brine (50 ml.), dried, and evaporated to an oil (1.07 g.). This material was purified by chromatography on 0.05–0.2mm. Kieselgel, with benzene; ethyl acetate = 10:1 as eluent. Combination of similar fractions (as judged by t.l.c.) gave the title compound (325 mg., 47%), as an amorphous white solid, m.p. 70° to 81° (decomp.), [α] −72.2° (CHCl$_3$), λ$_{max.}$ 313 nm (ε 9,300) with an inflexion at 237 nm. (ε 14,900), ν$_{max.}$ (CHBr$_3$) 3415 (NH), 1789 (β-lactam), 1728 (—CO$_2$R), and 1682 and 1510 cm.$^{-1}$ (CONH); the p.m.r. spectrum (CDCl$_3$) indicated that this compound was mainly the cis-isomer, with signals at τ 3.50 (NH, d, J 9 Hz.); 4.08 and ca. 2.60 (CH=CH, two d, J$_{AB}$ 12 Hz.); 4.09 (C$_{(7)}$-H, dd, J 5, 9 Hz.); 4.93 (C$_{(6)}$-H, d, J 5 Hz.); 5.33 (—CH$_2$CCl$_3$, s); 6.16 (—CH$_2$CONH—, s); and 6.29 and 6.61 (C$_{(2)}$—CH$_2$, AB-q J 18 Hz.), together with the trans-isomer (10 to 15%) with signals at τ 3.88 and 1.96 (CH=CH, two d, J 16 Hz.) [Found: C, 53.4; H, 3.6; N, 3.8; S, 9.1; Cl, 15.25; C$_{31}$H$_{25}$Cl$_3$N$_2$O$_6$S$_2$ (692.0) requires C, 53.8; H, 3.6; N, 4.05; S, 9.3; Cl, 15.4%]. R$_f$ 0.54 (Merck GF$_{254+266}$ plates, with benzene: ethyl acetate = 5:1 for development).

EXAMPLE 23

Diphenylmethyl 7β-(2-Thienylacetamido)-3-(3-hydroxyprop-1-enyl)-ceph-3-em-4-carboxylate A stirred suspension of glycolaldehyde (300 mg., 5mmole) in dry chloroform (30 ml.) was treated with diphenylmethyl 3-(triphenylphosphoranylidenemethyl)-7β-(2-thienylacetamido) ceph-3-em-4-carboxylate (383 mg., 0.5 mmole); the mixture was heated to reflux for 1 hour, and the solvent removed in vacuo. A solution of the residue in ethyl acetate (25 ml.) was washed with water (2 × 25 ml.) and brine (25 ml.), and dried, and evaporated to an oily foam (393 mg.). This material was purified by chromatography on 0.05–0.2 mm. Kieselgel, with benzene: ethyl acetate = 2:1 as eluent. Combination of similar fractions (as judged by t.l.c. R$_f$ 0.45; Merck GF$_{254+366}$ plates, with benzene: ethyl acetate = 1:1 for development) gave the title compound (63 mg., 23%) as a white solid, m.p. 69° to 75° (decomp.), [α]$_D$ − 10.7° (CHCl$_3$), λ$_{max.}$ 290 nm. (ε 9,300), with an inflexion at 235 nm (ε 13,700), ν$_{max.}$ (CHBr$_3$) 3630 (OH), 3416 (NH), 1784 (β-lactam), 1722 (CO$_2$R), and 1682 and 1510 cm.$^{-1}$ (CONH); the p.m.r. spectrum indicated that this compound was mainly the cis-isomer, with signals at τ (CDCl$_3$) 3.32 (NH, d, J 9 Hz.), 3.86 (—CH=CHCH$_2$OH, d, J 12 Hz.), 4.20 (C$_{(7)}$-H, dd, J 5, 9 Hz.), 4.38 (=CHCH$_2$OH, complex m), 5.02 (C$_{(6)-H, d, J}$ 5 Hz.), 5.90 and 6.20 (two m, —CH$_2$OH), 6.19 (—CH$_2$CONH—, s), and 6.56 and 6.79 (C$_{(2)}$-CH$_2$, AB-q J$_{AB}$ 18 Hz.) [Found: C, 62.55; H, 4.85; N, 4.8; S, 11.4;

$C_{29}H_{26}N_2O_5S_2$ ½$H_2O$ (555.7) requires C, 62.7; H, 4.9; N, 5.0; S, 11.5%].

EXAMPLE 24

(a) DL-2-Amino-2-(2-naphthyl)acetic acid

A solution of 5-(2-naphthyl) hydantoin (10g., 44.5 mmole) in 10% sodium hydroxide solution (50 ml.) was heated under reflux for 18 hours. The solution was cooled, filtered, diluted and treated with concentrated hydrochloric acid to bring the pH to 5.0. The resulting solid was filtered off washed with water and added to 5N-hydrochloric acid (2 L.). Insoluble material was filtered off and the filtrate was taken to pH 5.0 with 40% sodium hydroxide solution. On standing, the amino-acid crystallised out as platelets (3.92 g.) m.p. 238°–240°, $\lambda\lambda_{max.}$ (pH 6.0 phosphate) 225 ($\epsilon$ 51,700), 276 ($\epsilon$ 3,520), 268 nm. ($\epsilon$ 3,420).

(b) DL-2-t-Butoxycarbonylamino-2-(2-naphthyl) acetic acid

2N-Sodium hydroxide (12.6 ml.) was added to suspension of DL-2-amino-2-(2-naphthyl) acetic acid (5.06 g., 25.2 mmole) in a solution of sodium carbonate (7.93 g., 75.6 mmole) in water (25 ml.). t-Butanol (36 ml.) was then added and the mixture heated under reflux to obtain a clear solution. t-Butyl p-nitro-phenylcarbonate (12.1 g., 50.4 mmole) was then added in portions during 3 hours and the mixture was heated for a further hour. t-Butanol was removed in vacuo and the yellow solid was filtered off. The filtrate was covered with isopropyl ether and the pH was adjusted to 5.0 by the addition of concentrated hydrochloric acid. The layers were separated and the aqueous layer extracted again with isopropyl ether. The combined ethereal extracts were extracted three times with saturated sodium bicarbonate solution and the combined aqueous extracts were acidified with concentrated hydrochloric acid and extracted with ethyl acetate. The organic extract was washed with water and brine, dried over magnesium sulphate, and concentrated in vacuo to give a solid that was triturated with petroleum (40°–60°) to afford the protected amino-acid as a pink solid (4.04 g.) m.p. 149° (decomp.), $\lambda\lambda_{max.}$ (ethanol) 226 ($\epsilon$ 69,500), 268 ($\epsilon$ 4,720), 275 nm. ($\epsilon$ 5,100).

(c) t-Butyl 7β-[DL-2-t-Butoxycarbonylamino-2-(2-naphthyl)-acetamido]-3-vinylceph-3-em-4-carboxylate A suspension of t-butyl 7β-amino-3-vinylceph-3-em-4-carboxylate hydrogen p-toluenesulphonate (1.14 g. 2.5 mmole) in methylene chloride was shaken with a solution of sodium hydrogen carbonate (206 mg., 1 equiv.) in water (20 ml.) until the organic layer cleared. The aqueous phase was reextracted with methylene chloride (20 ml.), and the combined organic phases were washed with water (20 ml.), and dried. The solution of t-butyl 7β-amino-3-vinylceph-3-em-4-carboxylate so obtained was stirred and treated with a solution of DL-dicyclohexylcarbodiimide (515 mg., 1 equiv.) in methylene chloride (20 ml.), followed by a solution of Dl-2-t-butoxycarbonylamino-2-(2-naphthyl) acetic acid (753 mg., 1.0 equiv.) in methylene chloride (20 ml.), previously warmed to achieve solution. The reaction mixture was stirred at 23° for 2½ hours, and the precipitated N,N'-dicyclohexylurea was filtered off. The filtrate was washed with 3%-sodium hydrogen carbonate solution (30 ml.), water (20 ml.), 2N-hydrochloric acid (20 ml.), and water (20 ml.), dried and evaporated to a pale-yellow solid. This solid was triturated with ethyl acetate (160 ml.), the insoluble dicyclohexylurea was removed by filtration, and the filtrate was evaporated to give the title ester as a crystalline solid (1.26 g, 80%), $\lambda_{max.}$ 288 nm ($E_{1cm}^{1\%}$ 283), $\gamma_{max.}$ (CHBr$_3$) 3426 (NH), 1780 (azetidin-2-one), 1720 (CO$_2$R), 1708 and 1500 (NH CO$_2$R), 1694 (CONH) and 908 cm$^{-1}$ (=CH$_2$). The pmr spectrum of the product in CDCl$_3$ showed it to be a 1:1-mixture of the two diastereoisomers (the new center of asymmetry is in the side-chain attached to the 7-position).

(d) 7β-[DL-2-Amino-2-(2-naphthyl)acetamido]-3-vinylceph-3-em-4-carboxylic Acid A solution of t-butyl 7β-(DL-2-t-butoxycarbonylamino-2-[2-naphthyl]acetamido)-3-vinylceph-3-em-4-carboxylate (1.24 g. 2.19 mmole) in trifluoroacetic acid (16 ml.) and anisole (5 ml.) was kept at 24° for 10 minutes. The solvents were removed in vacuo to give an orange solid which was triturated and then stirred for 30 minutes with a mixture of ether (20 ml.) and ethyl acetate (5 ml.). The supernatant liquors were decanted and the procedure was repeated with a similar ethyl acetate-ether mixture. The off-white crystalline solid so obtained was filtered off, washed with ethyl acetate-ether (1:4) and dried to give a ca. 1:1-mixture of the hydrated title amino-acid and its trifluoroacetate salt (0.82 g, 77.5%), m.p. 190° to 195°, [α]−55.4°, $\lambda_{max.}$ (dissolved in one drop of N,N-dimethylformamide and diluted with ethanol) 280.5 ($\epsilon$ 16,700) and 288 nm ($\epsilon$ 17,300), $\gamma_{max.}$3500 (H$_2$O), 2600 (NH$_3$ and CO$_2$H), 1770 (azetidin-2-one), 1680 (CF$_3$CO$_2$) and 900 cm$^{-1}$ (=CH$_2$) (Found: C, 54.6, 54.5; H, 4.4, 4.4; F, 5.8; N, 8.4, 8.1; S, 6.25. $C_{21}H_{19}N_3O_4S$. 0.5 CF$_3$CO$_2$H. H$_2$O (484.5) requires C, 54.6; H, 4.5; F, 5.9; N, 8.7; S, 6.6%), Rp (system A) 0.31. The pmr spectrum of the product in Me$_2$SO-d$_6$ showed it to be a 1:1 - mixture of the two diastereoisomers.

SECTION B

EXAMPLE 1

(a) Diphenylmethyl 3-formyl-7β-(2-thienylacetamido) ceph-3-em-4-carboxylate

Diphenylmethyl 3-hydroxymethyl-7β-(2-thienylacetamido)-ceph-3-em-4-carboxylate (520 mg; 1 m.mole) was dissolved at 0° in acetone [30 ml, purified by distillation from Jones reagent J. Chem. Soc., 1946, 39)]. Jones reagent (0.30 ml; 1.1 m.mole; 8N-CrO$_3$ in Ca. 25% sulphuric acid) was added during 2 minutes and the mixture stirred for a further 3 minutes before being poured into water (100 ml) and ethyl acetate (100 ml). The product was extracted into ethyl acetate. Drying and evaporation gave a gum which solidified (0.32 g) on trituration with ether; the ether solution gave a further amount of solid (0.13 g) on evaporation. Thin-layer chromatography showed these crops to be identical.

A sample crystallised from ethanol in fine needles m.p. 162°–164° [α]$_D$ − 1.12° (dioxan); $\lambda\lambda_{max.}$ 231 nm ($\epsilon$13,200), 293-5 nm. ($\epsilon$10,400) $\nu_{max.}$ (CHBr$_3$) 1675 cm$^{-1}$ (—CHO), $\tau$ (CDCl$_3$) 0.40 (1-proton s, CHO), 3.50 (1-proton d, J9Hz 1 NH), 4.08 (1-proton dd, J 5 and 9Hz C$_7$-H), 5.03 (1-proton d, J 5 Hz; C$_6$-H), 6.20 (2-proton s; CH$_2$ CONH), 6.04 and 6.81 (AB q, J 18 Hz; C$_{(2)}$CH$_2$). (Found: C, 62.4; H, 4.5; N, 4.9. $C_{27}H_{22}N_2O_5S_2$ requires C, 62.6; H, 4.3; N, 5.3%). R$_F$ 0.95 (Kieselgel G, ethyl acetate-benzene - 2:1), 0.6 (Kieselgel G, ethyl acetate-benzene - 1:4).

(b) Diphenylmethyl 3-(trans-2-ethoxycarbonylvinyl)-7β-(2-thienylacetamido)ceph-3-em-4-carboxylate A solution of ethoxycarbonylmethylenetriphenylphosphorane (4.86 g., 13.9 mmole) in dry methylene chloride (45 ml.) was added slowly (over ca. 20 minutes) to a solution of diphenylmethyl 3-formyl-7β-(2-thienylacetamido)ceph-3-em-4-carboxylate (7.2 g., 13.9 mmoles. After 40 minutes at room temperature, the solution was washed with N-hydrochloric acid (40 ml.) and water, and dried and evaporated in vacuo. The residue, in benzene-ethyl acetate (8:1), was chromatographed on Kieselgel (0.02 - 0.5 mm., 500 g.). Fractions containing material with similar mobilities on T.L.C. ($R_F$ ca. 0.7) were combined and evaporated in vacuo. The residue was dissolved in ethyl acetate and the solution run into petroleum ether to give the trans-vinyl compound (1.71 g., 21%) as an amorphous solid. A portion (200 mg.) of this material was crystallised from methanol to give a pure sample (142 mg.) as fine needles, m.p. 162.3° ]$\alpha]_D$ − 192.6° (CHXl$_3$), $\lambda_{max}$ 319 nm. ($\epsilon$22,100), $\nu_{max.}$ (CHBr$_3$) 3400 (NH), 1782 (β-lactam), 1720 (4-CO$_2$R), 1700 (CH=CHCO$_2$R), 1690 and 1520 cm.$^{-1}$ (CONH), $\tau$ (CDCl$_3$) 3.52 (NH, d, J 9Hz.); 4.04 and 2.15 (CH=CH, two d, J 16 Hz.), 4.15 (C$_{(7)}$-H, dd, J 4.5, 9 Hz.), 5.06 (C$_{(6)}$-H, d, J 4.5 Hz.). 5.83 and 8.76 (—OCH$_2$CH$_3$; q and t, J 7 Hz.,), 6.20 (—CH$_2$CONH, s) and 6.48 and 6.69 (C$_{(2)}$-CH$_2$, AB-q (nearly collapsed to a s), J 18 Hz.). (Found: C, 63.3; H, 4.8; N, 4.45; S, (10.7. C$_{31}$H$_{28}$N$_2$O$_6$S$_2$ requires C, 63.25; H, 4.8; N, 4.75; S,10.9%).

(c) 3-(trans-2-Ethoxycarbonylvinyl)-7β-(2-thienylacetamido) ceph-3-em-4-carboxylate Diphenylmethyl 3-(trans-2-ethoxycarbonylvinyl)-7β-(2-thienylacetamido)ceph-3-em-4-carboxylate (1.02 g.) was treated with anisole (1 ml.) and trifluoroacetic acid (4 ml.). After 4 minutes at room temperature the solvents were removed in vacuo. The residue was dissolved in ethyl acetate and the solution extracted with saturated sodium bicarbonate solution containing an equal volume of water. The alkaline solution was taken to pH 7 with N-hydrochloric acid and traces of organic solvent evaporated in vacuo. The aqueous solution was taken to pH 2 with N-hydrochloric acid and the precipitated solid collected by filtration and washed with water and dried to give the acid (600 mg., 82%). This material was crystallised from ethyl acetate-petroleum ether to give a purer sample (435 mg.) as fine needles, m.p. 245° (decomp.) [$\alpha]_D$ − 56.5° (MeOH), $\lambda_{max.}$ 227 nm. ($\epsilon$12,850) and 320 nm. ($\epsilon$24,500); $\lambda_{max.}$(0.1M-pH 6 phosphate buffer( 232 nm. ($\epsilon$12,160) and 318 nm. ($\epsilon$25,220), $\lambda_{max.}$ 3280 (NH), 1780 (β-lactam), 1728 (CO$_2$R) 1690 (CO$_2$H), 1660 and 1530 cm.$^{-1}$ (CONH), $\tau$ (CDCl$_3$ containing 1 drop dimethylsulphoxide( 2.2 (NH, d, J 9 Hz.), 2.08 and 4.02 (—CH=CH-, two d, J 16 Hz.), 4.19 (C$_{(7)}$-H, dd, J 9 and 4.5 Hz.), 5.0 (C$_{(6)}$-H, d, J 4.5 Hz.), 6.18 (CH$_2$CONHs, s) and 6.47 (C$_{(2)}$-CH$_2$), s), $R_F$0.52 (System B) and 0.64 (system C) (Found: C, 51.3; H, 4.3; N, 6.4; S, 15.2. C$_{18}$H$_{18}$N$_2$O$_6$S$_2$ requires C, 51.2; H, 4.3; N, 6.6; S, 15.2%).

EXAMPLE 2

(a) Diphenylmethyl 3-(trans-2-diphenylmethoxycarbonylvinyl)-7β-(2-thienylacetamido)ceph-3-em-4-carboxylate A solution of diphenylmethoxycarbonylmethylenetriphenylphosphorane (4.0 g., 8.24 mmoles) in dry methylene chloride (45 ml.) at −20° was added slowly (over ca. 20 minutes) to a solution of diphenylmethyl 3-formyl-7β-(2-thienylacetamido)ceph-3-em-4-carboxylate (4.28 g., 8.26 mmoles) at −20°. After 1 hour at −20° the solution was washed with N-hydrochloric acid (50 ml.) and water, and dried and evaporated in vacuo. The residue, in benzeneethyl acetate (8:1), was chromatographed on Kieselgel (0.02 -0.05 mm., 300 g.). Fractions containing material with similar mobilities on T.L.C. ($R_F$ ca. 0.7) were combined and evaporated in vacuo. A solution of the residue in ethyl acetate was run into petroleum ether to give the trans-vinyl compound (1.68 g., 28%) as an amorphous solid, m.p. ca. 94° [$\alpha]_D$ − 153.5° (CHCl$_3$), $\lambda_{max.}$ 321 nm ($\epsilon$20,650), $\nu_{max.}$ 3300 (NH), 1780 (β-lactam), 1715 (C=C—CO$_2$R) and 1680 cm.$^{-1}$ (CONH), $\tau$ (CDCl$_3$) 3.61 (NH, d, J 9 Hz.), 2.02 and 3.9 (CH=CH, two d, J 16 Hz.), 4.18 (C$_{(7)}$-H, dd, H 4.5 and 9 Hz.), 5.06 (C$_{(6)}$-H, D, J 4.5 Hz.), 6.2 (CH$_2$CONH), s), and 6.51 (C$_{(2)}$-CH$_2$, s) (Found: C, 68.5; H, 4.7; N, 3.7; S, 8.5. C$_{42}$H$_{34}$N$_2$O$_6$S$_2$ requires C, 69.4; H, 4.7; N, 3.85; N, 3.85; S, 8.8%).

(b) 3-(trans-2-Carboxyvinyl)-7β-(2-thienylacetamido)ceph-3-em-4-carboxylic acid Diphenylmethyl 3-(trans-2-diphenylmethoxycarbonylvinyl)-7β-(2-thienylacetamido)ceph-3-em-4-carboxylate (1.63 g.) was treated with anisole (3.4 ml.) and trifluoroacetic acid (12.8ml.). After 4 minutes at room temperature the solvents were removed in vacuo. The residue was dissolved in ethyl acetate and the solution extracted with saturated sodium bicarbonate containing an equal volume of water. Traces of ethyl acetate were removed from the alkaline solution in vacuo and it was taken to pH 1 with concentrated hydrochloric acid. The precipitated solid was collected by filtration and washed with water, dried and crystallised from ethyl acetate to give the acid (470 mg.) as fine needles, m.p. 146°-149° (decomp), [$\alpha]_D$ + 18.4° (1% - NaHCO$_3$), $\lambda_{max.}$ (0.1M-pH 6 phosphate buffer) 234 nm. ($\epsilon$7,965 ) and 308 nm. ($\epsilon$20,900), $\nu_{max.}$ 3270 (NH), 1780 (β-lactam), 1714 and 2570 (-CO$_2$H), and 1644 and 1540 (CONH), $\tau$ (D$_2$O - NaHCO$_3$) 2.70 and 3.98 (CH=CH, two d, j 16 Hz.), 4.39 (C$_{(7)}$-H, d, J 4.5 Hz.), 4.39 (C$_{(6)}$-H, d, H 4.5 Hz.), 6.11 (CH$_2$CONH, s), 6.39 (C$_{(2)}$-CH$_2$, s) and 7.94 and 8.77 (0.6 mole ethyl acetate), R$_F$0.14 (System B) and 0.05 (System C) (Found: C, 48.4; H, 4.1; N, 5.7; S, 13.3. C$_{16}$H$_{14}$N$_2$O$_6$S$_2$ (0.6 CH$_3$CO$_2$C$_2$H$_5$) requires C, 49.4; H, 4.25; N, 6.25; S, 14.3%).

EXAMPLE 3

(a) Diphenylmethyl 3-(cis-2-cyanovinyl)-7β-(2-thienylacetamido)ceph-3-em-4-carboxylate A solution of cyanomethylenetriphenylphosphorane (3.77 g., 12.5 mmoles) in dry methylene chloride (45 ml.) at −20° was added slowly (over ca. 20 minutes) to a solutin of diphenylmethyl 3-formyl-7β-(2-thienylacetamido) ceph-3-em-4-carboxylate (6.48 g., 12.5 mmoles) at −20°. After 40 minutes at −20° the solution was washed with N-hydrochloric acid (45 ml.) and water, and dried and evaporated in vacuo. The residue, in benzene-ethyl acetate (8:1), was chromatographed on Kieselgel (0.02 - 0.5 mm., 380 g.). Fractions containing material with similar mobilities on T.L.C. ($R_F$ ca. 0.6) were combined and evaporated in vacuo. The residue (2.76 g., 40%) was crystallised from acetone - light petroleum to give the cis- vinyl compound (2.26 g., 33%) as fine needles, m.p. 171.5°–172.5° (decomp), $[\alpha]_D$ − 258° ($CHCl_3$), $\lambda_{max.}$ 318 nm. ($\epsilon$17,700), $\nu_{max.}$($CHBr_3$) 3415 (NH), 2230 (C≡N), 1796 ($\beta$-lactam), 1728 ($CO_2R$) and 1690 and 1512 cm.$^{-1}$ (CONH), $\tau$ ($CDCl_3$) 2.9 and 4.8 (CH=CH, two d, J 12 Hz.), 3.44 (NH, d, J 9 Hz.), 4.1 ($C_{(7)}$-H, dd, J 4.5 and 9 Hz.), 5.02 ($C_{(6)}$-H, d, j 9 Hz.), 5.89 and 6.29 ($C_{(2)}$-$CH_2$, AB-q, J 18 Hz.), 6.19 ($CH_2CONH$), s), (Found: c, 64.2; H, 4.4; N, 7.5; S, 11.5. $C_{29}H_{23}N_3O_4S_2$ requires C, 64.3; H, 4.3; N, 7.75; S, 11.85%).

(b)
3-(cis-2-Cyanovinyl)-7$\beta$-(2-thienylacetamido)ceph-3-em-4-carboxylic acid.

Diphenylmethyl 3-(cis-2-cyanovinyl)-7$\beta$-(2-thienylacetamido)ceph-3-em-4-carboxylate (1 g.) was treated with anisole (1 ml.) and trifluoroacetic acid (4 ml.). After 4 minutes at room temperature the solvents were removed in vacuo. The residue was dissolved in ethyl acetate and the solution extracted with saturated sodium bicarbonate solution containing an equal volume of water. Traces of ethyl acetate were removed from the alkaline solution in vacuo, which was taken in pH 2 with N-hydrochloric acid. The precipitated solid was collected by filtration and washed with water, and dried and crystallised from ethyl acetate - light petroleum to give the acid (370 mg., 53%) as needles, m.p. 157°–158° (decomp.), $[\alpha]_D$ − 127° (c 0.9,1% - $NaHCO_3$), $\lambda_{max.}$ (0.1M-pH 6 phosphate buffer) 233 nm. ($\epsilon$11,450) and 317 nm. ($\epsilon$22,860), $\nu_{max}$ 3310 (NH), 2218 (C≡N), 1775 ($\beta$-lactam), 1713 and 2600 ($CO_2H$), and 1620and 1540 cm.$^{-1}$ (CONH), $\tau$ ($D_2O$ - $NaHCO_3$) 2.92 and 4.59 (CH=CH, two d, J 13), 4.36 ($C_{(7)}$-H, dd, J 4.5 and 9 Hz.), 4.89 ($C_{(6)}$-H, d, j 4.5 Hz.), 5.94 and 6.2 ($C_{(2)}$—$CH_2$; AB-q, J 17 Hz.), and 6.12 ($CH_2CONH$, s) (Found: C, 50.9; H, 3.6; N, 11.4; S, 16.95. $C_{16}H_{13}N_3O_4S$ requires C, 51.2; H, 3.5; N, 11.2; S, 17.1%) $R_F$ 0.45 (System C).

EXAMPLE 4

(s) Diphenylmethyl 3-(trans-2-cyanovinyl)-7$\beta$-l (2-thienylacetamido)ceph-3-em-4-carboxylate Fractions from the column described in Example B 3 (a) with $R_F$ca. 0.5 on T.L.C. were combined and evaporated in vacuo. The residue was crystallised from acetone - light petroleum to give the trans- vinyl compound (410 mg., 6%), as needles, m.p. 174°–175° (decomp.), $[\alpha]_D$ − 203.20 ($CHCl_3$), $\lambda_{max.}$($CHCl_3$) 321 nm. ($\epsilon$22,070), $\nu_{max.}$($CHBr_3$) 3350 (NH), 2210 (C≡N), 1778 ($\beta$-lactam), 1713 ($CO_2R$), and 1675 and 1500 cm.$^{-1}$ (CONH), $\tau$ ($CDCl_3$) 1.82 (NH, d, J 9 Hz.), 2.60 and 4.52 (CH=CH, two d, J 16 Hz.), 4.16 ($C_{(7)}$-H, dd, J 4.5 and 9 Hz.), 5.0 ($C_{(6)}$-H, d, J 4.5 Hz.), 6.2 ($CH_2CONH$, s) and 6.58 ($C_{(2)}$-$CH_2$,s). Found: C, 63.9; H, 4.2; N, 7.1; S, 11.75 $C_{29}H_{23}N_3C_4S_2$ requires C, 64.3; N, 4.3; N, 7.75; S, 11.85%).

(b)
3-(trans-2-Cyanovinyl)-7$\beta$-(2-thineylacetamido)ceph-3-em-4-carboxylic acid Diphenylmethyl 3-(trans-2-cyanovinyl)-7$\beta$-(2-thienylacetamido)ceph-3-em-4-carboxylate (340 mg.) was treated with anisole (0.4 ml.) and trifluoroacetic acid (1.6 ml.). After 4 minutes at room temperature the solvents were removed in vacuo. The residue was triturated with ether to give the acid (203 mg., 86%) as an amorphous solid. This material was dissolved in ethyl acetate and the solution run into petroleum ether to give a purer sample (185 mg.) as an amorphous solid, m.p. 158° to 166° (decomp.), $[\alpha]_D$ − 21.6° (1%-$NaHCO_3$), $\lambda_{max.}$(0.1M-pH6phosphate buffer) 232 nm. and ($\epsilon$17,680) and 317 nm. ($\epsilon$27,450), $\nu_{max.}$($CHBr_3$) 3540 (broad, $H_2O$), 3400 (NH), C≡N), 1790 ($\beta$-lactam), 1730 ($CO_2H$), and 1690 and 1520 (CONH), $\tau$ ($D_2O$, with $NaHCO_3$) 2.54 and 4.43 (CH=CH, two d, J 17 Hz.), 4.36 ($C_{(7)}$-H, d, J 4.5 Hz.), 4.86 ($C_{(6)}$-H, d, J 4.5 Hz.), 6.14 ($CH_2CONH$, s), and 6.50 ($C_{(2)}$-$CH_2$, s), $R_F$0.57 (System B) and 0.25 (System C) (Found: C, 48.8; H, 3.6; N, 10.6; S, 16.1. $C_{16}H_{13}N_3O_4S_2$. $1H_2O$ requires C, 48.8; H, 3.85; N, 10.7; S, 16.3%).

EXAMPLE 5

(a)
7$\beta$-(D-2-t-Butoxycarbonylamino-2-phenylacetamido)-3-hydroxymethylceph-3-em-4-carboxylic acid A suspension of 3-acetoxymethyl-7$\beta$-(D-2-t-butoxycarbonylamino-2-phenylacetamido)-ceph-3-em-4-carboxylic acid (50 g.) in water (2 l.) was treated with defatted wheat germ (250 g.) and the pH of the mixture adjusted to ca 6.8 with 2N-dosium hydroxide. The mixture was stirred at 37° for 24 hours and the pH kept at 6.5–6.9 by the addition of further amounts of 2N-sodium hydroxide. [A total of 100 ml. (ca 2 equivalents) of sodium hydroxide was used]. Paper chromatography (System C) indicated that hydrolysis was complete after this period. The mixture was poured into acetone (ca 3 l.) and treated with Kieselguhr; insoluble material was removed by filtration. The filtercake was washed with aqueous acetone and acetone removed from the combined filtrates in vacuo. The aqueous solution was extracted with ethyl acetate (2 × ca 500 ml.), cooled to 5°, and the pH adjusted to 2.5 with orthophosphoric acid. The mixture was extracted with ethyl acetate and the extracts dried and evaporated to low volume in vacuo (i.e. until crystallisation started). Filtration gave 7$\beta$-(D-2-t-butoxycarbonylamino-2-phenylacetamido)-3-hydroxymethylceph-3-em-4-carboxylic acid (23 g.) as small needles, m.p. 187°, $[\alpha]_D$ + 21° (dioxan), $\lambda_{max.}$ (0.1 M-pH6 phosphate buffer) 258 nm. ($\epsilon$ 7,000), $\nu_{max.}$ 1766 ($\beta$-lactam), 1715 ($CO_2R$), 1680 ($CO_2H$), and 1655 and 1515 cm.$^{-1}$ (—CONH—), $\tau$ ($CDCl_3$) 2.65 (Ph), ca 4.55 ($C_{(7)}$-H, ill-resolved 1-proton m), ca 5.1 ($C_{(6)}$-H and CH[$NHCO_2C(CH_3)_3$], ill-resolved 2-proton complex), 5.86 (CH[$NHCO_2C(CH_3)_3$], d, J 6 Hz), 8.6 (C($CH_3$)$_3$) (Found: C, 54.7; H, 5.8; N, 8.9; S, 6.0. $C_{21}H_{25}N_3O_7S$ requires C, 54.4; H, 5.4; N, 9.0; S, 6.9%), Rf 0.44 (System C).

(b) Diphenylmethyl 7$\beta$-(D-2-t-butoxycarbonylamino-2-phenylacetamido)-3-hydroxymethylceph-3-em-4-carboxylate The total crude product from the hydrolysis of 3-acetoxymethyl-7$\beta$-(D-2-t-butoxycarbonylamino-2- phenylacetamido)ceph-3-em-4-carboxylic acid (9 g.), with wheat germ (90 g.) (see Example B 5 (a) was dissolved in tetrahydrofuran (150 ml.) and treated with an excess of diphenyldiazomethane in petroleum ether (b.p. 40° to 60°) at 22° overnight. A few drops of acetic acid were added to the solution, which was evaporated in vacuo. The resulting foam was dissolved in ethyl acetate and the solution run into petroleum ether (b.p. 40° to 60°) to give the ester as an amorphous solid (10.3 g., 92%), $\lambda_{max.}$ (dioxan) 265 nm. ($\epsilon$ 5,540), $\nu_{max.}$ (CHBr$_3$) 3550 (OH), 3400 (NH), 1780 ($\beta$-lactam), 1710 (CO$_2$R) and 1690 and 1510 cm.$^{-1}$ (—CONH—). A portion (1 g.) of this material was crystallised from ethanol to give a purer sample (426 mg.) as fine needles, m.p. 151°-2°, $[\alpha]_D - 20.8°$ (dioxan), $\lambda_{max.}$ (dioxan) 264 nm. ($\epsilon$ 7,152), $\nu_{max.}$ (CHBr$_3$) 3670 (H$_2$O), 3550 (OH), 3400 (NH), 1780 ($\beta$-lactam), 1710 (CO$_2$R) and 1690 and 1510 cm.$^{-1}$ (—CONH—), $\tau$ (CDCl$_3$) 2.74 (Ph), 3.12 (CHPh$_2$), ca. 4.15 (C$_{(7)}$-H, part of a dd, J 4.5), 4.28 (CH[NHCO$_2$C(CH$_3$)$_3$], d, J 6 Hz.), 4.8 (CH[NHCO$_2$C(CH$_3$)$_3$], d, J 6 Hz.), 5.2 (C$_{(6)}$-H, d, J 4.5 Hz.), 5.61 and 6.1 (-CH$_2$OH, AB-q, J 12.5 Hz.), 6.65 (C$_{(2)}$-CH$_2$) and 8.62 (C(CH$_3$)$_3$) (Found: C, 64.0; H, 5.7; N, 6.3; S, 5.0. C$_{34}$H$_{35}$N$_3$O$_7$S, 0.5 H$_2$O requires C, 63.9; H, 5.7; N, 6.6; S, 5.0%).

(c) Diphenylmethyl 3-formyl-7$\beta$(D-2-t-butoxycarbonylamino-2-phenylacetamido)ceph-3-em-4-carboxylate A solution of diphenylmethyl 7$\beta$-(D-2-t-butoxycarbonylamino-2-phenylacetamido)-3-hydroxymethyl ceph-3-em-4-carboxylate (11.1 g.) in acetone (250 ml; purified by distillation from Jones' reagent) was treated with Jones' reagent (4.9 ml., 1.1 equivalents) at 22°. The mixture was stirred vigorously for five minutes, then poured into saturated brine (500 ml.) and ethyl acetate (500 ml.). The aqueous phase was extracted with ethyl acetate and the combined extracts washed with brine, and dried and evaporated in vacuo. The residue was crystallised from benzene to give the 3-formyl derivative (3.5 g., 32%) as fine needles, m.p. 183°-185°, $[\alpha]_D - 152.7°$ (tetrahydrofuran), $-174°$ (c 0.9, CHCl$_3$), $\lambda_{max.}$ 295 nm. ($\epsilon$ 11,150), $\nu_{max.}$ (CHBr$_3$) 3440 (NH), 1880 ($\beta$-lactam), 1728 (CO$_2$R), 1700 and 1500 (NHCO$_2$R), 1692 (CHO), 1674 and 1500 (CONH), and 760 cm.$^{-1}$ (phenyl), $\tau$ (CDCl$_3$) 0.42 (CHO), 2.69 (phenyl), 2.94 (CHPh$_2$), ca 3.0 (CONH), 4.1 (C$_{(7)}$-H, dd, J 4.9 and 9 Hz), 4.4 (CHNH, d, J 7 Hz.), 4.8 (CHNH, d, J 7 Hz), 5.1 (C$_{(6)}$-H, d, J 4.5 Hz), 6.14 and 6.89 (C$_{(2)}$-CH$_2$, AB-q, J 18 Hz) and 8.61 (C(CH$_3$)$_3$) (Found: C, 65.7; H, 5.65; N, 6.65; S, 5.2. C$_{34}$H$_{33}$N$_3$O$_7$S requires C, 65.1; H, 5.3; N, 5.1%).

The filtrate from the above crystallisation was run into petroleum ether (b.p. 40° to 60°) to give a further amount (5.22 g., 47%) of usable aldehyde, $\lambda_{max.}$ 294 nm. ($\epsilon$ 9,000), with an infrared spectrum identical to that of the crystalline sample.

(d) Diphenylmethyl 33-(trans-2-ethoxycarbonylvinyl)-7$\beta$-(D-2-t-butoxycarbonylamino-2-phenylacetamido)ceph-3-em-4-carboxylate A solution of ethoxycarbonylmethylenetriphenylphosphorane (3.83 g.) in dry methylene chloride (45 ml.) at −20° was added slowly (over ca. 20 minutes) to a solution of diphenylmethyl 3-formyl-7$\beta$-(D-2-t-butoxycarbonylamino-2-phenylacetamido)ceph-3-em-4-carboxylate (6.92 g.) in methylene chloride (45 ml.) at −20°. After 1½ hours at −20° the solution was washed with N-hydrochloric acid (100 ml.) and water and dried and evaporated in vacuo. The residue (10 g.), in benzene-ethyl acetate (8:1) was chromatographed on Kieselgel (0.02–0.5 mm., 400 g.). Fractions containing material with similar mobilities on T.L.C. (R$_F$ ca. 0.7) were combined and evaporated in vacuo. The residue was dissolved in ethyl acetate and the solution run into petroleum ether to give the trans vinyl compound (850 mg.) as an amorphous solid, m.p. ca. 105°, $[\alpha]_D - 144.6°$ (CHCl$_3$), $\lambda_{max.}$ 318 nm. ($\epsilon$ 18,300), $\nu_{max.}$ (CHBr$_3$) 3400 (NH), 1780 ($\beta$-lactam) and 1700 cm.$^{-1}$ (broad, CO$_2$R), $\tau$ (CDCl$_3$) 2.2 and 4.11 (CH=CH, two d, J 16 Hz.), 3.12 (C$_{(7)}$—NH-CO, d, J 9 Hz.), 4.20 (C$_{(7)}$-H, dd, J 4.5 and 9 Hz.), 4.36 (CH[NHCOOC(CH$_3$)$_3$], d, J 6 Hz), 4.81 (CH[NHCOOC(CH$_3$)$_3$], d, J 6Hz.), 5.17 (C$_{(6)}$-H, d, J 4.5 Hz.), 5.85 and 8.79 (CO$_2$C$_2$H$_5$, q and t, J 7 Hz.), 8.61 (C(CH$_3$)$_3$, s) (Found: C, 64.7; H, 5.65; N, 6.05; S, 4.7. C$_{38}$H$_{39}$N$_3$O$_8$S requires C, 65.4; H, 5.6; N, 6.0; S, 4.7%).

(e) 7$\beta$-(D-2-Aminophenylacetamido)-3-(trans-2-ethoxycarbonylvinyl)-ceph-3-em-4-carboxylic acid, trifluoroacetic acid salt Diphenylmethyl 3-(trans-2-ethoxycarbonylvinyl)-7$\beta$-(D-2-t-butoxycarbonylamino-2-phenylacetamido)ceph-3-em-4-carboxylate (900 mg.) was treated with anisole (0.9 ml.) and trifluoroacetic acid (3.6 ml.). After 5 minutes at room temperature the solvents were removed in vacuo and the residue partitioned between ethyl acetate and water containing trifluoroacetic acid (0.1 ml.). The aqueous solution was washed thoroughly with ethyl acetate, then freeze-dried to give the amine salt (470 mg.) as an amorphous solid, m.p. 142°-145° (decomp), $[\alpha]_D - 80.8°$ (tetrahydrofuran), $\lambda_{max.}$ 320 nm. ($\epsilon$ 17,800), $\nu_{max.}$ ca. 2600 (CO$_2$H), 1700 ($\beta$-lactam) and 1680 cm.$^{-1}$(C=C, CO$_2$R and CF$_3$CO$_2^-$), $\tau$ (DMSO-d$_6$) 0.41 (C$_{(7)}$-NHCO, d, J 9 Hz.), 2.33 and 3.86 (CH=CH, two d, J 16 Hz.), 4.2 (C$_{(7)}$-H, dd, J 4.5 and 9 Hz.), 4.91 (C$_{(6)}$-H, d, J 4.5 Hz.), 5.00 (CH-N$^+$H$_3$, s) 5.89 and 8.81 (CO$_2$C$_2$H$_5$, q and t, J 7 Hz.), and 6.19 and 6.57 (C$_{(2)}$-CH$_2$, AB-q, J 18 Hz.), R$_F$0.5 (System C) (Found: C, 46.85; H, 4.15; F, 10.9; N, 7.75; S, 6.0. C$_{22}$H$_{22}$F$_3$N$_3$O$_8$S. H$_2$O requires C, 46.9; H, 4.3; F, 10.5; N, 7.5; S, 5.7%).

EXAMPLE 6

(a) Diphenylmethyl 3-(trans-2-diphenylmethoxycarbonylvinyl)-7$\beta$-(D-2-t-butoxycarbonylamino-2-phenylacetamido)ceph-3-em-4-carboxylate A solution of diphenylmethoxycarbonylmethylenetriphenylphosphorane (4.05 g., 8.3 mmole) in dry methylene chloride (45 ml.) at −20° was added slowly (over ca. 30 minutes) to a solution of diphenylmethyl 7$\beta$-(D-2-t-butoxycarbonylamino-2-phenylacetamido)-3-formylceph-3-em-4-carboxylate (5.2 g., 8.3 mmole) in methylene chloride (45 ml.) at −20°. After 1 hour at −20° the solution was washed with N-hydrochloric acid (45 ml.) and water, and dried and evaporated in vacuo. The residue (9.6 g.), in benzene - ethyl acetate (8:1) was chromatographed on Kieselgel (0.02 - 0.5 mm., 350 g.). Fractions containing material with similar mobilities on T.L.C. (R$_F$ ca. 0.6) were combined and evaporated in vacuo. The residue was crystallised from acetone - methanol to give the trans-vinyl compound (600 mg.) as needles, m.p. 156°-158°, $[\alpha]_D - 163°$ (CHCl$_3$), $\lambda_{max.}$ 321 nm. ($\epsilon$ 23,100), $\nu_{max.}$ (CHBr$_3$) 3370

(NH), 1780 (β-lactam), 1710 (CO$_2$R), and 1690 and 1498 cm.$^{-1}$ (CONH), τ (CDCl$_3$) 2.07 and 3.97 (CH=CH, two d, J 16 Hz.), 3.15 (C$_{(7)}$-NHCO, d, J 9 Hz.), 4.22 (C$_{(7)}$-H, dd, J 4.5 and 9 Hz.), 4.42 (CHNH COOC(CH$_3$)$_3$, d, J 6 Hz.), 4.83 [CHNHCOOC(CH$_3$)$_3$, d, J 6 Hz.] 5.24 (C$_{(6)}$-H, d, J 4.5 Hz.), 6.54 and 6.74 (C$_{(3)}$-CH$_2$, AB-q, J 18 Hz.), 8.6 (C(CH$_3$)$_3$, s) (Found: C, 69.5; H, 5.4; N, 5.1; S, 3.9. C$_{49}$H$_{45}$N$_3$O$_8$S requires C, 70.5; H, 5.4; N, 5.0; S, 3.8%).

(b)
7β-(D-2-Aminophenylacetamido)-3-(trans-2-carboxyvinyl)ceph-3-em-4-carboxylic acid, trifluoroacetic acid salt Diphenylmethyl 3-(trans-2-diphenylacetylvinyl)-7β-(D-2-t-butoxycarbonylamino-2-phenylacetamido)ceph-3-em-4-carboxylate (685 mg.) was treated with anisole (0.7 ml.) and trifluoroacetic acid (2.8 ml.). After 5 minutes at room temperature the solvents were removed in vacuo and the residue partitioned between ethyl acetate and water containing a small amount of trifluoroacetic acid. The aqueous layer was separated and freeze-dried to give the diacid salt (372 mg.) as an amorphous solid, m.p. ca. 165° (decomp.), [α]$_D$ − 41.0° (1%-NaHCO$_3$), λ$_{max.}$ (0.1M-pH 6 phosphate buffer) 309 nm. (ε 20,700), ν$_{max.}$ (CHBr$_3$), 1780 (β-lactam), 1710 and 2620 (CO$_2$H), 1690 cm.$^{-1}$ (CF$_3$CO$_2^-$), τ (D$_2$O-NaHCO$_3$) 2.37 and 4.06 (CH=CH two d, J 16 Hz.), 4.27 (C$_{(7)}$-H, d, J 4.5 Hz.), 4.77 (CHCONH, s), 4.92 (C$_{(6)}$-H, d, J 4.5 Hz.), and 6.54 (C$_{(2)}$-CH$_2$, s), R$_F$ 0.05 (System B) (Found C, 45.75; H, 3.4; F, 11.25; N, 8.15; S, 6.2. C$_{20}$H$_{18}$F$_3$N$_3$O$_8$S ½ H$_2$O requires C, 45.6; H, 3.65; F, 10.85; N, 8.0; F, 11.0; S, 6.1%).

EXAMPLE 7

(a)
3-Acetoxymethyl-7β-(2-thienylacetamido)ceph-2-em-4-carboxylic acid

A solution of 3-acetoxymethyl-7β-(2-thienylacetamido)ceph-3-em-4-carboxylic acid (146.5 g.) in pyridine (600 ml.) was treated with acetic anhydride (45 ml.) and the mixture stirred vigorously at 22° for 45 minutes. The material which crystallised out was isolated by filtration washed with pyridine and ethyl acetate, and dried in vacuo to give the pyridinium salt of the title compound (95.15 g., 54.5%). This pyridinium salt was stirred with water (350 ml.) and ethyl acetate (700 ml.) and 2N-hydrochloric acid (ca 120 ml.) added until all the solid had dissolved. The organic phase was separated, washed with water, dried and evaporated in vacuo to give the title compound (77 g.) as a white solid, m.p. 151°–152.5°, [α]$_D$ + 480° 5% sodium carbonate), λ$_{max.}$ 235 nm. (ε 15,200), ν$_{max.}$ 3293 (NH), 1746 (β-lactam), 1722 and 2600 (CO$_2$H), 1722 and 1208 (CH$_2$OCOCH$_3$) and 1660 and 1528 cm.$^{-1}$ (CONH), τ (D$_2$O - sodium bicarbonate) 2.7 and 3.0 (thienyl, 1-proton t and 2-proton d), 3.62 (C$_{(2)}$-H, broad s), 4.58 (C$_{(7)}$-H, d, J 4.5 Hz), 4.69 (C$_{(6)}$-H, d, J 4.5 Hz), 5.18 (C$_{(4)}$-H, broad s), 6.15 (CH$_2$CONH, s) and 7.9 (-OCOCH$_3$, s) (CH$_2$OAc obscured by H$_2$O band). (Found: C, 48.3; H, 4.1; N, 7.0; S, 16.2. Calc. for C$_{16}$H$_{16}$N$_2$O$_6$S$_2$: C, 48.4; H, 4.05; N, 7.05; S, 16.15%).

(b)
3-Hydroxymethyl-7β-(2-thienylacetamido)ceph-2-em-4-carboxylic acid

A suspension of 3-acetoxymethyl-7β-(2-thienylacetamido)ceph-2-em-4-carboxylic acid (42 g.) in water (400 ml.) was flushed with nitrogen and potassium carbonate (43 g.) added. The mixture was treated with water (200 ml.) to effect complete solution and methanol (50 ml.) added. The solution was stored at 37° for 4.25 hours and then at 22° for 17 hours. The methanol was removed in vacuo and the mixture diluted with water (200 ml.) and stirred with ethyl acetate (800 ml.). The pH of the mixture was adjusted to 2.5 with orthophosphoric acid and the organic layer separated and washed with water and dried. The ethyl acetate was evaporated in vacuo until crystallisation of the product started, and the mixture cooled. Filtration gave the title compound (19.7 g., 52.5%) as fine needles, m.p. 151.5°–152° (decomp), [α]$_D$ + 465° (tetrahydrofuran), λ$_{max.}$ 234 nm. (ε 14,400), ν$_{max.}$ 3250 (NH and bonded OH), 2600 and 1725 (CO$_2$H), 1755 (β-lactam) and 1650 and 1520 cm$^{-1}$ (CONH), τ (D$_2$O-sodium bicarbonate) 2.65 and 3.0 (thienyl, 3-proton complex), 3.7 (C$_{(2)}$-H, broad s), 4.62 (C$_{(2)}$-H, d, J 4.5 Hz), 4.74 (C$_{(6)}$-H, d, J 4.5 Hz), 5.15 (C$_{(4)}$-H, broad s), 5.8 (CH$_2$OH, broad s) and 6.12(CH$_2$CONH, s). (Found: C, 47.4; H, 4.05; N, 7.65; s 18.0; Calc. for C$_{14}$H$_{14}$N$_2$O$_5$S$_2$: C, 47.5; H, 3.9; N, 7.9; S, 18.1%).

(c) Diphenylmethyl 3-hydroxymethyl-7β-(2-thienylacetamido) ceph-2-em-4-carboxylate A solution of 3-hydroxymethyl-7β-(2-thienylacetamido) ceph-2-em-4-carboxylic acid (19.3 g.) in dry, peroxidefree, tetrahydrofuran (400 ml.) was treated with an excess of a ca 10% solution of diphenyldiazomethane in petroleum ether. The mixture was stored at 22° for 18 hours, then treated with methanol (2.5 ml.) and glacial acetic acid (4 ml.), and the solvents removed in vacuo. The residual solid was washed with ether to give the title compound (25.84 g., 91%), m.p. 169°–170° (decomp), [α]$_D$ + 383° (tetrahydrofuran), λ$_{max.}$ 236 nm. (ε 14,100), ν$_{max.}$ (CHBr$_3$) 3610 (OH), 3420 (NH), 1780 (β-lactam), 1745 (CO$_2$R) and 1680 and 1515 cm$^{-1}$(CONH), τ (DMDO-d$_6$) 3.46 (C$_{(2)}$-H, broad s), 4.5 (C$_{(7)}$-H, dd, J 8.5 and 4.5 Hz), ca. 4.8 (C$_{(6)}$-H, and C$_{(4)}$-H, m) 5.95 (CH$_2$OH, broad s) and 6.16 (CH$_2$CONH, s). (Found: C, 62.4; H, 4.7; N, 5.3; S, 11.8. C$_{27}$H$_{24}$N$_2$O$_5$S$_2$ requires C, 62.5; H, 4.45; N, 5.4; S, 12.35%).

(d) Diphenylmethyl 3-formyl-7β-(2-thienylacetamido) ceph-2-cm-4-carboxylate

A solution of diphenylmethyl 3-hydroxymethyl-7β-(2-thienylacetamido)ceph-2-em-4-carboxylate (10.41 g.) in freshly distilled acetone (500 ml.) was stirred at 0° and treated with Jones' reagent (6.5 ml, 1.3 equiv). over a five-minute period. After 40 minutes a further amount (1 ml.) of Jones' Reagent was added, and after a further 10 minutes the reaction was judged complete on examination by T.L.C. (System E). The mixture was poured into saturated brine, 1500 ml, and extracted with ethyl acetate, (1000 ml). The extracts were washed with water, dried and evaporated in vacuo. The residue was taken up in ethyl acetate and the solvent evaporated in vacuo carefully until crystallisation started. The mixture was diluted with ether to complete crystallisation, and the solid collected to give the 3-formyl derivative (7.43 g., 71%) as fine needles, m.p. 141°–143° (decomp), [α]$_D$ + 472° (CHCl$_3$), λ$_{max.}$ 285.5 nm. (ε 17,800), ν$_{max.}$ (CHBr$_3$) 3460 (NH), 2760 (CHO), 1783 (β-lactam), 1744 (CO$_2$R), 1690 (—C=C—CO) and 1680 and 1510 cm.$^{-1}$ (CONH), τ (CDCl$_3$) 0.72 (CHO), 2.58 (C$_{(2)}$-H, broad s), 3.18 (CHPh$_2$), 4.50 (C$_{(4)}$-H), broad s), 4.56 (C$_{(7)}$-H, part of a dd J 4.5 Hz), 4.86 (C$_{(6)}$-H, d, J 4.5 Hz) and 6.20 (CH$_2$CONH). (Found: C, 62.8; H, 4.4; N, 5.4; S, 12.5. C$_{27}$H$_{22}$N$_2$O$_5$S$_2$ requires C, 62.5; H, 4.25; H, 5.4; S, 12.35%).

(e) Diphenylmethyl 3-(trans-2-ethoxycarbonylvinyl)-7β-(2-thienylacetamido)ceph-2-em-4-carboxylate A solution of diphenylmethyl 3-formyl-7β-(2-thienylacetamido)ceph-2-4-carboxylate (1.14 g.) in methylene dichloride (20 ml.) was treated with a solution of ethoxycarbonylmethylenetriphenylphosphorane (770 mg.) in methylene dichloride (25 ml.). The solution was stirred for 6½ hours at 20°, then left at −10° for 18 hours. The organic solution was washed with 2N-hydrochloric acid, and water, dried, and evaporated in vacuo. The resulting cream-coloured foam was crystallised from methanol to give the vinyl compound (790 mg., 61.5%) as needles, m.p. 154.5°–155°, [α]$_D$ + 480° (CHCl$_3$), λ$_{max}$. 308 nm. (ε 23,800), 84 $_{max.}$ (CHBr$_3$) 3450 (NH), 1777 (β-lactam), 1740 (CO$_2$R), 1700 and 1260 (C=C—CO$_2$R), 1690 and 1505 (CONH), 1620 (C=C) and 970 cm.$^{-1}$ (trans C=C), τ 2.86 and 4.11 (CH=CH, two d, J 16 Hz.), 3.31 (C$_{(2)}$-H, broad s), 4.49 (C$_{(7)}$-H, dd J 9 and 4.5 Hz), 4.71 (C$_{(4)}$-H, broad s), 4.75 (C$_{(6)}$-H, d, J 4.5 Hz), 6.17 (CH$_2$CONH) and 5.81 and 8.72 (OCH$_2$CH$_3$, q and t). (Found: C, 63.5; H, 4.8; N, 5.3; S, 10.95. C$_{31}$H$_{28}$N$_2$O$_6$S$_2$ requires C, 63.4; H, 4.8; N, 4.75; S, 10.9%).

EXAMPLE 8

Diphenylmethyl 3-(trans-2-methylcarbonylvinyl)-7β-(2-thienylacetamido)ceph-2-em-4-carboxylate A solution of diphenylmethyl 3-formyl-7β-(2-thienylacetamido)ceph-2-em-4-carboxylate (116 mg.) in benzene (3 ml.) was treated with a solution of methylcarbonylmethylenetriphenylphosphorane (150 mg.) in benzene (4 ml.) and the mixture refluxed for 5.75 hours. The organic solution was washed with 2-N-hydrochloric acid and water, dried and evaporated in vacuo. The residual gum (186 mg.) was purified by preparative T.L.C. (Kieselgel HF$_{254+366}$, developed five times with benzene-ethyl acetate = 8:1) to give the title compound (32 mg, 27%) as a gum, λ$_{max.}$ (CHCl$_3$) 318 nm. (qualitative, τ (CDCl$_3$) 3.00 and 3.86 (CH=CH, two d, J 16 Hz), 3.12 (CHPh$_2$), 3.27 (C$_{(2)}$-H, broad s), 4.47 (C$_{(7)}$-H), dd, J 8 and 4 Hz), 4.73 (C$_{(6)}$-H, d, J 4 Hz), 4.69 (C$_{(4)}$-H, broad s), 6.16 (CH$_2$CONH) and 7.91 (COCH$_3$).

EXAMPLE 9

Diphenylmethyl 3-(trans-2-ethoxycarbonylvinyl)-7β-(2-thienylacetamido)ceph-3-em-4-carboxylate A solution of diphenylmethyl 3-(trans-2-ethoxycarbonylvinyl)-7β-(2-thienylacetamido)ceph-2-em-4-carboxylate (234 mg.) in methylene dichloride (2 ml.) was cooled to 0° and treated with pure acetic anhydride (1 drop) and peracetic acid (0.075 ml.). After 20 minutes a further amount (0.02 ml.) of peracetic acid was added. After a total of 70 minutes the mixture was diluted with methylene chloride and the organic solution washed with saturated sodium bicarbonate, and water and dried and evaporated. The residue was dissolved in chloroform and the solution run into petroleum ether to give the Δ$^3$-sulphoxide (174 mg. 76%) as an amorphous solid, τ (DMSO-d$_6$) 1.41 (NH, d, J 9 Hz), 2.17 and 3.67 (CH=CH, two d, J 16 Hz), 3.95 (C$_{(7)}$-H, dd, J 9 and 4.5 Hz), 4.94 (C$_{(6)}$-H, d, J 4.5 Hz), 5.55 and 6.41 (C$_{(2)}$-CH$_2$, AB-q, J 18 Hz), 5.85 and 8.74 (OCH$_2$CH$_3$, q and t) and 6.09 (CH$_2$CONH). The p.m.r. spectrum showed the presence of ca 10% of a Δ$^2$-compound.

The sulphoxide (117 mg.) in methylene dichloride (2.5 ml.) was cooled to −20° and treated with a solution of PBr$_3$ (79 mg.) in methylene dichloride (0.7 ml.). After 22 minutes the mixture was diluted with more methylene dichloride and washed with aqueous sodium bicarbonate and water and dried and evaporated in vacuo. The residue (100 mg.) was triturated with methanol to give a pale yellow solid. This material had a p.m.r. spectrum very similar to that of authentic product, showing only trace amounts of a Δ$^2$- impurity.

Biological results of certain of the compounds prepared in the Examples are given in table V below.

Table V

| | | Tube Dilution Assay (γ/ml.) | | | | | | | |
|---|---|---|---|---|---|---|---|---|---|
| | | Gram Positive | | | | | Gram Negative | | |
| Compound | | Staph. aureus 604 | Staph. aureus 663 | Staph. aureus 3452 | Staph. aureus 11127 | Strep. faecalis 850 | E. coli 573 | S. typh 804 | Pr. mirab 431 |
| Aiii | 1b | 0.6 | 0.08 | <0.5 | <0.5 | 62 | 62 | 8 | 31 |
| " | 2b | 1.25 | 0.16 | 2 | 2 | 250 | 62 | 62 | 8 |
| " | 5b | 0.4 | 0.08 | 8.0 | 1 | 62 | 250 | 125 | 31 |
| " | 10c | 1.6 | 0.3 | 1.6 | 1.6 | 250 | 8 | 125 | 4 |
| " | 11b | 0.04 | 0.08 | 0.1 | 0.2 | | >250 | >250 | 62 |
| " | 13c1 | 0.16 | 0.02 | <0.5 | <0.5 | | >250 | >250 | >250 |
| " | 13c2 | 1.6 | 0.4 | 3.1 | 3.1 | | >250 | 250 | 31 |
| " | 13c3 | 1.25 | 0.1 | 4 | 4 | | 250 | 250 | 250 |
| " | 13c4 | 6.2 | 1.25 | 16 | 8 | | 250 | 250 | >250 |
| " | 13c5 | 0.16 | 0.04 | <0.5 | <0.5 | | >250 | 250 | 250 |
| " | 13c6 | 1.25 | 0.6 | 2 | 2 | | >250 | 250 | >250 |
| " | 13c7 | 1.6 | 0.2 | 1.6 | 6.2 | | 62 | 31 | 8 |
| " | 13c8 | 1.6 | 0.2 | 1.6 | 6.2 | | 31 | 31 | 16 |
| " | 13c9 | 0.8 | 0.2 | <0.5 | <0.5 | | >250 | >250 | 16 |
| " | 13bxi cont | 6.2 | 12.5 | 125 | 125 | | 125 | 31 | 125 |
| " | 24(d) | 2.5 | 0.6 | 2 | 2 | | >250 | 250 | 250 |
| B1c | | 3.1 | 0.1 | 8 | 31 | 4 | 8 | <4 | |
| B2b | | 25 | 12.5 | 16 | 16 | 16 | 31 | 4 | <0.5 |
| B3b | | 2.5 | 0.6 | 2 | 2 | 16 | 31 | 8 | 4 |
| B4b | | 2.5 | 2.5 | 2 | 2 | 2 | 4 | 4 | 8 |

Pharmaceutical Examples

A. Tablet (a) 7-(D-2-Amino-2-phenylacetamido)-3-vinylceph-3-em-4-carboxylic acid —250 mg.

(b) Mannitol —75 mg.
(c) Potato Starch —46 mg.
(d) Maize Starch —25 mg.
(e) Magnesium stearate —4 mg.

The dry ingredients (a), (b) and (c) were blended together and granulated with a 10% aqueous paste of (d). The granules were passed through a No. 12 mesh (B.S.) screen dried to constant weight and sieved through a No. 16 mesh (B.S.) screen. The granules were then lubricated by blending in (e) and compressed at 400 mg. per tablet on suitable punches. The tablets may be coated if required, for instance with a readily soluble conventional film coating.

B. Capsule 7-(D-2-Amino-2-phenylacetamido)-3-vinylceph-3-em-4-carboxylic acid —250 mg. *Aerosil composition —3 mg.

The dry powders were blended together homogeneously and distributed into well filled, hard gelatine capsules, so that each contained 250 mg. of the active ingredient.

"A silicon dioxide/starch blend available from Bush, Beach and Gent of Marlon House, Lloyd's Avenue, London, E.C.3"

We claim:

1. In a process for the preparation of a compound of the formula $$\text{R}^1\text{NH} \diagdown \text{S} \diagup \text{R}^3$$

I (structure with R¹NH, S, N, COOH, CH=C, R³, R⁴)

wherein $R^1$ is carboxylic acyl of from 1-20 carbon atoms and each of $R^3$ and $R^4$ is a member selected from the group consisting of a hydrogen atom; lower alkyl; cyclopentyl; cyclohexyl; phenyl; phenyl substituted by halogen, lower alkyl or nitro; lower alkoxycarbonyl; lower alkylcarbonyl; cyano; carboxy; phenylloweralkoxycarbonyl; diphenylloweralkoxycarbonyl; benzyl and phenylethyl, the steps of (A) reacting a cephalosporin of the formula

II (structure with R¹NH, Z, N, COOR⁶, CH₂Hal)

wherein $R^1$ has the above defined meaning, $R^6$ is hydrogen or a carboxyl-blocking group, Z is > S or > S → O, Hal is a chlorine, bromine or iodine atom, and the dotted line between positions 2, 3 and 4 represents a double bond at position 3, 4 or 2, 3 with a compound of the formula $PR_3$ or $P(OR)_3$ where R is lower alkyl, phenyl or benzyl or lower alkyl, phenyl or benzyl substituted by at least one of a halogen atom, nitro, cyano, or amino to produce a compound of the formula

III (structure with R¹NH, Z, N, COOR⁶, CH₂Y)

wherein $R^1$, $R^6$, Z and dotted line are as defined above and Y is a group $-P^+R_3$ or $-PO(OR)_2$ where R is as defined above, (B) reacting the compound obtained in Step (A) with a base selected from the group consisting of an alkali metal of an alkaline earth hydroxide, carbonate, or hydrogen carbonate; ethoxycarbonylmethylenediphenylphosphorane; the conjugate base of dimethylsulphoxide, dimethylacetamide or dimethylformamide; pyridine; triethylamine; a sodio or lithio derivative of hexamethyldisilazane; an alkali metal alkoxide; ethylene oxide and propylene oxide to abstract therefrom a proton to produce a compound of the formula

IV (structure with R¹NH, Z, N, COOR⁶, Q)

where $R^1$, $R^6$, Z and the dotted line are as defined above and Q is a group $-CH=PR_3$ or $-\ominus CH-PO(OR)_2$ where R has the above defined meaning, and (C) reacting the compound obtained in step (B) with a carbonyl compound of the formula $$R^3.CO.R^4$$

wherein $R^3$ and $R^4$ are as defined above to produce a compound of the formula

V (structure with R¹NH, Z, N, COOR⁶, CH=C, R³, R⁴)

wherein $R^1$, Z, $R^3$, $R^4$, $R^6$ and the dotted line are as defined above.

2. A process as claimed in claim 1 wherein R is n-butyl or phenyl.

3. A process as claimed in claim 1 wherein the base in step (B) is an alkali metal or an alkaline earth metal hydroxide, carbonate or hydrogen carbonate.

4. A process as claimed in claim 2 wherein the base in step (B) is ethoxycarbonylmethylenediphenylphosphorane; the conjugate base of dimethylsulphoxide, dimethylacetamide or dimethylformamide; pyridine; triethylamine; a sodio or lithio derivative of hexamethyldisilazane; an alkali metal alkoxide; ethylene oxide or propylene oxide.

5. In a process for the preparation of a compound of the formula

I (structure with R¹NH, S, N, COOH, CH=C, R³, R⁴)

wherein $R^1$ is carboxylic acyl of from 1-20 carbon atoms and each or $R^3$ and $R^4$ is a member selected from the group consisting of a hydrogen atom; lower alkyl; cyclopentyl; cyclohexyl; phenyl; phenyl substituted by halogen, lower alkyl or nitro; lower alkoxycarbonyl; lower alkylcarbonyl; cyano; carboxy; phenylloweralkoxycarbonyl; diphenylloweralkoxycarbonyl; benzyl and phenylethyl, the step of reacting a cephalosporin of the formula

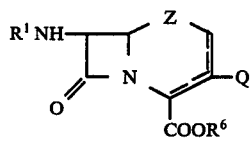

where $R^1$ is as defined above, $R^6$ is hydrogen or a carboxyl-blocking group, Z is $>$ S or $>$ S → O, the dotted line between positions 2, 3 and 4 represents a double bond at position 3, 4 or 2, 3 and Q is a group —CH=PR$_3$ or — ⊖ CH-PO(OR)$_2$ where R is lower alkyl, phenyl or benzyl or lower alkyl, phenyl or benzyl substituted by at least one of a halogen atom, nitro, cyano, or amino with a carbonyl compound of the formula $R^3.CO.R^4$ where $R^3$ and $R^4$ are as defined above to produce a compound of the formula

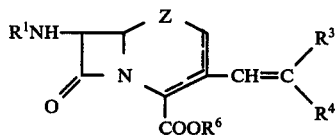

wherein $R^1$, Z, $R^3$, $R^4$, $R^6$ and the dotted line are as defined above.

6. A process as claimed in claim 5 wherein the reaction is carried out at from −30° to +100° C.

7. A process as claimed in claim 5 wherein the reaction is carried out in an inert solvent selected from the group consisting of methylene chloride, benzene, diethylether, tetrahydrofuran, dioxan, dimethylsulphoxide, dimethylformamide, dimethylacetamide and hexamethylphosphoramide.

8. A process as claimed in claim 7 wherein the inert solvent is methylene chloride.

9. A process as claimed in claim 7 wherein the inert solvent is benzene.

10. A process as claimed in claim 1 wherein the compound of formula I is 7β-(D-2-amino-2-phenylacetamido)-3-vinylceph-3-em-4-carboxylic acid; in step A, the compound of formula II is t-butyl 7β-(D-2-t-butoxycarbonylamino-2-phenylacetamido)-3-iodomethylceph-3-em-4-carboxylate, the compound of formula PR$_3$ is triphenylphosphine and the compound of formula III produced is [7β-(D-2-t- butoxycarbonylamino-2-phenylacetamido)-4-t-butoxycarbonyl-ceph-3-em-3-ylmethyl]triphenylphosphonium iodide; in step B, the base is sodium bicarbonate and the compound of formula IV produced is t-butyl 7β-(D-2-t-butoxycarbonylamino-2-phenylacetamido)-3-(triphenylphosphoranylidenemethyl)ceph -3-em-4-carboxylate; and in step C, the compound of formula $R^3.CO.R^4$ is formaldehyde and the compound of formula V produced is t-butyl 7β-(D-2-t-butoxycarbonylamino-2-phenylacetamido)-3-vinylceph-3-em-4-carboxylate.

* * * * *